US007745609B2

(12) United States Patent
Bennett et al.

(10) Patent No.: US 7,745,609 B2
(45) Date of Patent: *Jun. 29, 2010

(54) ANTISENSE MODULATION OF CD40 EXPRESSION

(75) Inventors: C. Frank Bennett, Carlsbad, CA (US); Lex M. Cowsert, Pittsburgh, PA (US); Andrew M. Siwkowski, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 11/466,369

(22) Filed: Aug. 22, 2006

(65) Prior Publication Data

US 2007/0161589 A1    Jul. 12, 2007

Related U.S. Application Data

(63) Continuation of application No. 10/698,689, filed on Oct. 31, 2003, now abandoned, and a continuation-in-part of application No. PCT/US03/31166, filed on Sep. 30, 2003, which is a continuation-in-part of application No. 10/261,382, filed on Sep. 30, 2002, now abandoned, and a continuation-in-part of application No. 09/067,638, filed on Apr. 28, 1998, now Pat. No. 7,321,828.

(60) Provisional application No. 60/081,483, filed on Apr. 13, 1998.

(51) Int. Cl.
C07H 21/04    (2006.01)
C07H 21/00    (2006.01)
A61K 31/70    (2006.01)

(52) U.S. Cl. ............... 536/24.5; 536/23.1; 536/25.3; 514/44

(58) Field of Classification Search ............... None
See application file for complete search history.

(56) References Cited

U.S. PATENT DOCUMENTS

| 3,687,808 | A | 8/1972 | Merigan |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,800,159 | A | 1/1989 | Mullis et al. |
| 4,806,463 | A | 2/1989 | Goodchild et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 4,981,957 | A | 1/1991 | Lebleu et al. |
| 5,013,830 | A | 5/1991 | Ohtsuka et al. |
| 5,023,243 | A | 6/1991 | Tullis |
| 5,034,506 | A | 7/1991 | Summerton et al. |
| 5,075,302 | A | 12/1991 | Neustadt |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,223,618 | A | 6/1993 | Cook et al. |
| 5,235,033 | A | 8/1993 | Summerton et al. |

(Continued)

FOREIGN PATENT DOCUMENTS

EP    0514927    11/1992

(Continued)

OTHER PUBLICATIONS

Opalinska et al. Nature Reviews Drug Discovery 2002, vol. 1, pp. 503-514.*

(Continued)

Primary Examiner—Tracy Vivlemore
(74) Attorney, Agent, or Firm—Isis Pharmaceuticals, Inc. Patent Dept.

(57) ABSTRACT

Antisense compounds, compositions and methods are provided for modulating the expression of CD40. The compositions comprise antisense compounds, particularly antisense oligonucleotides, targeted to nucleic acids encoding CD40. Methods of using these compounds for modulation of CD40 expression and for treatment of diseases associated with CD40 are provided.

46 Claims, No Drawings

U.S. PATENT DOCUMENTS

| | | | |
|---|---|---|---|
| 5,245,022 A | 9/1993 | Weis et al. | |
| 5,254,469 A | 10/1993 | Warren, III et al. | |
| 5,256,775 A | 10/1993 | Froehler | |
| 5,258,506 A | 11/1993 | Urdea et al. | |
| 5,262,536 A | 11/1993 | Hobbs, Jr. | |
| 5,264,423 A | 11/1993 | Cohen et al. | |
| 5,264,562 A * | 11/1993 | Matteucci | 536/23.1 |
| 5,264,564 A | 11/1993 | Matteucci | |
| 5,272,250 A | 12/1993 | Spielvogel et al. | |
| 5,276,019 A | 1/1994 | Cohen et al. | |
| 5,278,302 A | 1/1994 | Caruthers et al. | |
| 5,286,717 A | 2/1994 | Cohen et al. | |
| 5,292,873 A | 3/1994 | Rokita et al. | |
| 5,317,098 A | 5/1994 | Shizuya et al. | |
| 5,319,080 A | 6/1994 | Leumann | |
| 5,321,131 A | 6/1994 | Agrawal et al. | |
| 5,352,775 A | 10/1994 | Albertsen et al. | |
| 5,359,044 A | 10/1994 | Cook et al. | |
| 5,366,878 A | 11/1994 | Pederson et al. | |
| 5,367,066 A | 11/1994 | Urdea et al. | |
| 5,371,241 A | 12/1994 | Brush | |
| 5,378,825 A | 1/1995 | Cook et al. | |
| 5,386,023 A | 1/1995 | Sanghvi et al. | |
| 5,391,723 A | 2/1995 | Priest | |
| 5,393,878 A | 2/1995 | Leumann | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,407,794 A | 4/1995 | Cuting et al. | |
| 5,414,077 A | 5/1995 | Lin et al. | |
| 5,416,203 A | 5/1995 | Letsinger | |
| 5,432,272 A | 7/1995 | Benner | |
| 5,434,257 A | 7/1995 | Matteucci et al. | |
| 5,436,327 A | 7/1995 | Southern et al. | |
| 5,446,137 A | 8/1995 | Maag et al. | |
| 5,451,463 A | 9/1995 | Nelson et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,463,564 A | 10/1995 | Agrafiotis et al. | |
| 5,463,657 A | 10/1995 | Rice | |
| 5,466,677 A | 11/1995 | Baxter et al. | |
| 5,466,786 A | 11/1995 | Buhr et al. | |
| 5,470,967 A | 11/1995 | Huie et al. | |
| 5,472,672 A | 12/1995 | Brennan | |
| 5,476,925 A | 12/1995 | Letsinger et al. | |
| 5,484,908 A | 1/1996 | Froehler et al. | |
| 5,486,603 A | 1/1996 | Buhr | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,507,796 A | 4/1996 | Hasson | |
| 5,508,270 A | 4/1996 | Baxter et al. | |
| 5,510,475 A | 4/1996 | Agrawal et al. | |
| 5,512,439 A | 4/1996 | Hornes et al. | |
| 5,512,667 A | 4/1996 | Reed et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,523,389 A | 6/1996 | Ecker et al. | |
| 5,525,465 A | 6/1996 | Haralambidis et al. | |
| 5,525,711 A | 6/1996 | Hawkins et al. | |
| 5,529,756 A | 6/1996 | Brennan | |
| 5,536,821 A | 7/1996 | Agrawal et al. | |
| 5,539,082 A | 7/1996 | Nielsen et al. | |
| 5,539,083 A | 7/1996 | Cook et al. | |
| 5,541,306 A | 7/1996 | Agrawal et al. | |
| 5,541,307 A | 7/1996 | Cook et al. | |
| 5,541,313 A | 7/1996 | Ruth | |
| 5,543,508 A | 8/1996 | Haseloff et al. | |
| 5,545,730 A | 8/1996 | Urdea et al. | |
| 5,550,111 A | 8/1996 | Suhadolnik et al. | |
| 5,552,538 A | 9/1996 | Urdea et al. | |
| 5,552,540 A | 9/1996 | Haralambidis | |
| 5,554,613 A | 9/1996 | Mallion | |
| 5,561,225 A | 10/1996 | Maddry et al. | |
| 5,563,036 A | 10/1996 | Peterson et al. | |
| 5,563,253 A | 10/1996 | Agrawal et al. | |
| 5,565,350 A | 10/1996 | Kmiec | |
| 5,565,552 A | 10/1996 | Magda et al. | |
| 5,567,810 A | 10/1996 | Weis et al. | |
| 5,567,811 A | 10/1996 | Misiura et al. | |
| 5,571,799 A | 11/1996 | Tkachuk et al. | |
| 5,574,142 A | 11/1996 | Meyer, Jr. et al. | |
| 5,574,656 A | 11/1996 | Agrafiotis et al. | |
| 5,576,427 A | 11/1996 | Cook et al. | |
| 5,578,717 A | 11/1996 | Urdea et al. | |
| 5,578,718 A | 11/1996 | Cook et al. | |
| 5,580,731 A | 12/1996 | Chang et al. | |
| 5,585,481 A | 12/1996 | Arnold, Jr. et al. | |
| 5,587,361 A | 12/1996 | Cook et al. | |
| 5,587,371 A | 12/1996 | Sessler et al. | |
| 5,587,469 A | 12/1996 | Cook et al. | |
| 5,591,584 A | 1/1997 | Chang et al. | |
| 5,591,721 A | 1/1997 | Agrawal et al. | |
| 5,591,722 A | 1/1997 | Montgomery et al. | |
| 5,594,121 A | 1/1997 | Froehler et al. | |
| 5,595,726 A | 1/1997 | Magda et al. | |
| 5,596,086 A | 1/1997 | Matteucci et al. | |
| 5,596,091 A | 1/1997 | Switzer | |
| 5,597,696 A | 1/1997 | Linn et al. | |
| 5,597,909 A | 1/1997 | Urdea et al. | |
| 5,599,923 A | 2/1997 | Sessler et al. | |
| 5,599,928 A | 2/1997 | Hemmi et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,612,455 A | 3/1997 | Hoey | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,603 A | 6/1997 | Dower et al. | |
| 5,639,873 A | 6/1997 | Barascut et al. | |
| 5,641,625 A | 6/1997 | Ecker et al. | |
| 5,646,265 A | 7/1997 | McGee | |
| 5,650,122 A | 7/1997 | Harris et al. | |
| 5,652,355 A | 7/1997 | Metelev et al. | |
| 5,652,356 A | 7/1997 | Agrawal | |
| 5,720,923 A | 7/1997 | Harris et al. | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,677,437 A | 10/1997 | Teng et al. | |
| 5,677,439 A | 10/1997 | Weis et al. | |
| 5,681,941 A | 10/1997 | Cook et al. | |
| 5,684,711 A | 11/1997 | Agrafiotis et al. | |
| 5,688,941 A | 11/1997 | Cook et al. | |
| 5,693,463 A | 12/1997 | Edwards et al. | |
| 5,696,248 A | 12/1997 | Peyman et al. | |
| 5,697,248 A | 12/1997 | Brown et al. | |
| 5,700,637 A | 12/1997 | Southern | |
| 5,700,920 A | 12/1997 | Altmann et al. | |
| 5,700,922 A | 12/1997 | Cook | |
| 5,708,158 A | 1/1998 | Hoey | |
| 5,714,331 A | 2/1998 | Buchardt et al. | |
| 5,716,780 A | 2/1998 | Edwards et al. | |
| 5,719,262 A | 2/1998 | Buchardt et al. | |

| | | |
|---|---|---|
| 5,766,855 A | 6/1998 | Buchardt et al. |
| 5,773,571 A | 6/1998 | Nielsen et al. |
| 5,783,431 A | 7/1998 | Peterson et al. |
| 5,786,461 A | 7/1998 | Buchardt et al. |
| 5,789,573 A | 8/1998 | Baker et al. |
| 5,801,154 A | 9/1998 | Baracchini et al. |
| 5,824,485 A | 10/1998 | Thompson et al. |
| 5,831,014 A | 11/1998 | Cook et al. |
| 5,859,221 A | 1/1999 | Cook et al. |
| 5,864,010 A | 1/1999 | Cook et al. |
| 5,877,021 A | 3/1999 | Stinchcomb et al. |
| 5,901,069 A | 5/1999 | Agrafiotis et al. |
| 5,955,589 A | 9/1999 | Cook et al. |
| 5,969,116 A | 10/1999 | Martin |
| 5,986,053 A | 11/1999 | Ecker et al. |
| 6,016,348 A | 1/2000 | Blatter et al. |
| 6,025,339 A * | 2/2000 | Nyce ............................ 514/44 |
| 6,143,881 A | 11/2000 | Metelev et al. |
| 6,194,150 B1 * | 2/2001 | Stinchcomb et al. ........... 435/6 |
| 6,197,584 B1 | 3/2001 | Bennett et al. |
| 6,201,103 B1 | 3/2001 | Nielsen et al. |
| 6,204,326 B1 | 3/2001 | Cook et al. |
| 6,210,892 B1 | 4/2001 | Bennett et al. |
| 6,228,982 B1 | 5/2001 | Norden et al. |
| 6,295,514 B1 | 9/2001 | Agrafiotis et al. |
| 6,346,614 B1 | 2/2002 | Metelev et al. |
| 6,350,853 B1 | 2/2002 | Nielsen et al. |
| 6,395,474 B1 | 5/2002 | Buchardt et al. |
| 6,399,754 B1 | 6/2002 | Cook |
| 6,414,112 B1 | 7/2002 | Buchardt et al. |
| 6,421,612 B1 | 7/2002 | Agrafiotis et al. |
| 6,434,490 B1 | 8/2002 | Agrafiotis et al. |
| 6,441,130 B1 | 8/2002 | Egholm et al. |
| 6,451,968 B1 | 9/2002 | Egholm et al. |
| 6,453,246 B1 | 9/2002 | Agrafiotis et al. |
| 6,506,784 B1 | 1/2003 | Dhanoa et al. |
| 6,518,266 B1 | 2/2003 | Dhanoa et al. |
| 6,571,227 B1 | 5/2003 | Agrafiotis et al. |
| 6,582,908 B2 | 6/2003 | Fodor et al. |
| 6,593,292 B1 | 7/2003 | Rothbard et al. |
| 2001/0053519 A1 | 12/2001 | Fodor et al. |
| 2002/0049173 A1 | 4/2002 | Bennett et al. |
| 2003/0228597 A1 | 12/2003 | Cowsert et al. |
| 2005/0202531 A1 | 9/2005 | Toporik et al. |

FOREIGN PATENT DOCUMENTS

| | | |
|---|---|---|
| EP | 0650493 | 5/1995 |
| WO | WO 86/07363 | 12/1986 |
| WO | WO 89/10977 | 11/1989 |
| WO | WO 92/20702 | 11/1992 |
| WO | WO 93/04204 | 3/1993 |
| WO | WO 94/02498 | 2/1994 |
| WO | WO 94/02499 | 2/1994 |
| WO | WO 94/05333 | 3/1994 |
| WO | WO 94/17093 | 8/1994 |
| WO | WO 95/28640 | 10/1995 |
| WO | WO 96/11205 | 4/1996 |
| WO | WO 9611205 A1 * | 4/1996 |
| WO | WO 96/39415 | 12/1996 |
| WO | WO 9639415 A1 * | 12/1996 |
| WO | WO 97/22256 | 6/1997 |
| WO | WO 98/03533 | 1/1998 |
| WO | WO 98/37242 | 8/1998 |
| WO | WO 99/53101 | 10/1999 |
| WO | WO 99/57320 | 11/1999 |
| WO | WO 99/60010 | 11/1999 |
| WO | WO 01/27261 | 4/2001 |
| WO | WO 03/022222 | 3/2003 |

OTHER PUBLICATIONS

Buhlmann et al. Journal of Clinical Immunology 1996, vol. 16, pp. 83-89.*

Eliopoulos et al. Current Opinion in Pharmacology 2004, vol. 4, pp. 360-367.*

U.S. Appl. No. 08/465,880, filed Jun. 6, 1995, Cook.

U.S. Appl. No. 08/368,037, filed Jun. 6, 1995, Cook et al.

U.S. Appl. No. 08/762,488, filed Dec. 1, 1996, Cook et al.

Agrawal, "Antisense oligonucleotides: towards clinical trials" Tibtech (1996) 14:376-387.

Albelda et al., "Adhesion molecules and inflammatory injury" FASEB J. (1994) 8:504-512.

Albert et al., "Antisense knockouts: molecular scalpels for the dissection of signal transduction" TiPS (1994) 15:250-254.

Altschul et al., "Basic Local Alignment Search Tool" J. Mol. Biol. (1990) 215:403-410.

Altschul et al., "Gapped Blast and PSI-Blast: a new generation of protein database search programs" Nucl. Acids Res. (1997) 25(17):3389-3402.

Ausubel et al., "Short Protocols in Molecular Biology" 2nd Edition, Greene Publishing Associates and John Wiley & Sons, New York (1992) 4-1 to 4-29, 10-33 to 10-35, 10-57 to 10-63, 11-3 to 11-54.

Baker et al., "Cleavage of the 5'Cap Structure of mRNA by a Europium(III) Macrocyclic Complex with Pendant Alcohol Groups" J. Am. Chem. Soc. (1997) 119(38):8749-8755.

Beaucage et al., "Deoxynucleoside Phosphoramidites—A New Class of Key Intermediates for Deoxypolynucleotide Synthesis" TetrahedronLett. (1981) 22:1859-1862.

Boumpas et al., "A short course of BG9588 (anti-CD40 ligand antibody) improves serologic activity and decreases humaturia in patients with proliferative lupas glomerulonephritis" Arthritis Rheum (2003) 48:719-727.

Branch et al., "A good antisense molecule is hard to find," TIBS (1998) 23:45-50.

Brazma et al., "Gene expression data analysis" FEBS Lett. (2000) 480:17-24.

Buhlmann et al., "Therapeutic Potential for Blockade of the CD40 Ligand, gp39" J. Clin. Immunol. (1996) 16(2):83-89.

Carulli et al., "High Throughput Analysis of Differential Gene Expression" J. Cell Biochem. Suppl, (1998) 30/31:286-296.

Celis et al., "Gene expression profiling: monitoring transcription and translation products using DNA microarrays and proteomics" FEBS Lett. (2000) 480:2-16.

Chiang et al., "Antisense Oligonucleotides Inhibit Interceullular Adhesion Molecule 1 Expression by Two Distinct Mechanisms" J. Biol. Chem. (1991) 266:18162-18171.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Clement et al., "Protein tyrosine kinase activation and protein kinase C translocation are functional components of CD40 signal transduction in resting human B cells" Immunological Investigations (1994) 23(6-7):437-448.

Christensen et al., "Solid-Phase Synthesis of Peptide Nucleic Acids" J. Pept. Sci. (1995) 3(1):175-183.

Crooke et al., "Pharmacokinetic Properties of Several Novel Oligonucleotide Analogs in mice" J. Pharmacol. Exp. Therapeutics (1996) 277:923-937.

Crooke et al., "Basic Principles of Antisense Therapeutics" Antisense Research and Application (1998) Chapter 1:1-50.

Dahl et al., "A Highly Reactive, Odourless Substitute for Thiophenol/ Triethylamine as a Deprotection Reagent in the Synthesis of Oligonucleotides and their Analogues" Acta Chem. Scand. (1990) 44:639-641.

Decamp et al., "Site-directed drug design" Protein Engineering, Principles and Practice, Cleland, J.L., et al. (Ed.) 1996, Chapter 17, 467-472.

Demesmaeker et al., "Antisense Oligonucleotides" Acc. Chem. Res. (1995) 28(9):366-374.

Elbashir et al., "RNA interference is mediated by 21- and 22-nucleotide RNAs" Genes Dev. (2001) 15:188-200.

Elbashir et al., "Duplexes of 21-nucleotide RNAs mediate RNA interference in cultured mammalian cells" Nature (2001) 411:494-498.

Englisch et al., "Chemically Modified Oligonucleotides as Probes and Inhibitors" Angewandte Chemie, International Edition (1991) 30(6):613-629.

Eliopoulos et al., "The role of the CD40 pathway in the pathogenesis and treatment of cancer" Curren Opinion in Pharmacology (2004) 4:360-367.

Fire et al., "Potent and specific genetics interference by double-stranded RNA in Caenorhabditis elegans" Nature (1998) 391:806-811.

Forster et al., "External Guide Sequences for an RNA Enzyme" Science (1990) 249:783-786.

Freier et al., "The ups and downs of nucleic acid duplex stability: structure-stability studies on chemically-modified DNA:RNA duplexes" Nucl. Acids Res. (1997) 25:4429-4443.

Fuchs et al., "Identification of Differentially Expressed Genes by Mutually Subtracted RNA Fingerprinting" Anal. Biochem. (2000) 286:91-98.

Gewirtz et al., "Facilitating oligonucleotide delivery: Helping antisense deliver on its promise" PNAS USA (1996) 93:3161-3163.

Ghosh et al., "Evaluation of some properties of a phosphorodithioate oligodeoxyribonucleotide for antisense application" Nucl. Acid Res. (1993) 21(24):5761-5766.

Ghosh et al., "Phosphorothioate-phosphodiester oligonucleotide co-polymers: assessment for antisense application" Anti-Cancer Drug Design, XP-002110959, 1993, 8, 15-32.

Glasser, "ISIS Pharmaceuticals Demonstrates Efficacy in Crohn's Disease with its Antisense Drug" Genetic Engin. News (1997) 17:1.

Going et al., "Molecular Pathology and Future Developments" Eur. J. Cancer (1999) 35.

Griffin et al., "The Synthesis of Oligoribonucleotides-II: Methoxymethylidene Derivatives of Ribonucleosides and 5'-Ribonucleotides" Tetrahedron (1967) 23:2301-2313.

Gruss et al., "CD40/CD40 Ligand Interactions in Normal, Reactive and Malignant Lympho-Hematopoietic Tissues" Leuk. Lymphoma (1997) 24:393-422.

Guo et al., "par-1, a Gene Required for Establishing Polarity in C. elegans Embryos, Encodes a Putative Ser/Thr Kinase That is Asymmetrically Distributed" Cell (1995) 81:611-620.

Haseloff et al., "Simple RNA enzymes with new and highly specific endoribonuclease activities" Nature (1988) 334:585-591.

Hyndman et al., "Software to determine optimal oligonucleotide sequences based on hybridization simulation data" BioTechniques, XP002932984, Jun. 1996, 20, 1090-1097.

Hyrup et al., "Peptide Nucleic Acids (PNA): Synthesis, Properties and Potential Applications" Bioorg. Med. Chem. 1996, 4(1), 5-23.

Janeway, "How the Immune System Recognizes Invaders" Sci. Amer. (1993) 269, 73-79.

Jones et al., "A rapid method for recombination and site-specific mutagenesis by placing homologous ends on DNA using polymerase chain reaction" Biotechniques (1991) 10(1):62-66.

Jungblut et al., "Proteomics in human disease: Cancer, heart and infectious diseases" Electrophoresis (1999) 20:2100-2110.

Jurecic et al., "Long-distance DD-PCR and cDNA microarrays" Curr. Opin. Microbiol. (2000) 3:316-321.

Kabanov et al., "A new class of antivirals: antisense oligonucleotides combined with a hydrophobic substituent effectively inhibit influenza virus reproduction and synthesis of virus-specific proteins in MDCK cells" FEBS Letts. (1990) 259(2):327-330.

Kahn, "From Genome to Preteome: Looking at a Cell's Proteins" Science (1995) 270:369-370.

Karras et al., "Peptide Nucleic Acids are Potent Modulators of Endogenous Pre-mRNA Splicing of the Murine Interleukin-5 Receptor-a Chain" Biochemistry (2001) 40:7853-7859.

Kaiser et al., "Color test for detection of free terminal amino groups in the solid-phase synthesis of peptides" Anal. Biochem. (1970) 34(2):595-598.

Kluth et al., "Endothelial Expression of CD40 in Renal Cell Carcinoma" Cancer Res. (1997) 57:891-899.

Koppelhus et al., "Cell-dependent differential cellular uptake of PNA, peptides, and PNA-peptide conjugates" Antisense & Nucleic Acid Drug Develop. (2002) 12:51-63.

Kroschwitz (ed.), "Polynucleotides" Concise Encyclopedia of Polymer Science and Engineering, John Wiley & Sons (1990) 858-859.

Lacerra et al., "Restoration of hemoglobin a synthesis in erythroid cells from peripheral blood of thalassemic patients" PNAS (2000) 97(17):9591-9596.

Larson et al., "Rapid DNA Fingerprinting of Pathogens by Flow Cytometry" Cytometry (2000) 41:203-208.

Larsson et al., "High-throughput protein expression of cDNA products as a tool in functional genomies" J. Biotechnol. (2000) 80:143-157.

Letsinger et al., "Cholesteryl-conjugated oligonucleotides: Synthesis, properties and activity as inhibitors of replication of human immunodeficiency virus in cell culture" PNAS (1989) 86:6553-6556.

Lima et al., "Implication of RNA Structure on Antisense Oligonucleotide Hybridization Kinetics" Biochem (1992) 31:12055-12061.

Lomakin et al., "A theoretical analysis of specificity of nucleic acid interactions with oligonucleotides and peptide nucleic acids (PNAs)" J. Molecular Biology (1998) 276(1):1-24.

Lutgens et al., "Requirement for CD154 in the progression of atherosclerosis" Nat. Med. (1999) 5(11):1313-1316.

Mach et al., "Reduction of atherosclerosis in mice by inhibition of CD40 signalling" Nature (1998) 394(9):200-203.

Mach et al., "Functional CD40 ligand is expressed on human vascular endothelial cells, smooth muscle cells, and macrophages: Implications for CD40-CD40 ligand signaling in atherosclerosis" PNAS (1997) 94:1931-1936.

Madden et al., "Serial analysis of gene expression: from gene discovery to target identification" Drug Discov. Today (2000) 5(9):415-425.

Makgoba et al., "The CD2-LFA-3 and LFA-1-1CAM pathways: relevance to T-cell recognition" Immunol. Today (1989) 10(12):417-422.

Manoharan et al., "Cholic Acid-Oligonucleotide Conjugates for Antisense Applications" Bioorganic Med. Chem. Letts. (1994) 4(8):1053-1060.

Manoharan et al., "Chemical Modifications to Improve Uptake and Bioavailability of Antisense Oligonucleotides" Ann. N.Y. Acad. Sci (1992) 660:306-309.

Manoharan et al., "Introduction of a Lipophilic Thioether Tether in the Minor Groove of Nucleic Acids for Antisense Applications" Bioorg. Med. Chem. Letts. (1993) 3(12):2765-2770.

Manoharan et al., "Lipidic Nucleic Acids" Tetrahedron Letts. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Martin et al., "Ein neuer Zugang zu 2'-O-Alkylribonucleosiden und Eigenschaften deren Oligonucleotide" Helv. Chim. Acta (1995) 78:486-504 (English summary included).

Matteucci et al., "Synthesis of Deoxyoligonucleoties on a Polymer Support" J. Am. Chem. Soc. (1981) 103:3185-3191.

Mercatante et al., "Modification of alternative splicing pathways as a potential approach to chemotherapy" Pharmacol. & Ther. (2000) 85:237-243.

Milligan et al., "Current Concepts in Antisense Drug Design" Journal of Medicinal Chemistry (1993) 36(14):1923-1937.

Milner et al., "Selecting Effective Antisense Reagents on Combinatorial Oligonucleotide Arrays" Nature Biotechnology (1997) 15:537-541.

Mirabelli et al., "In vitro and in vivo pharmacologic activities of antisense oligonucleotides" Anti-Cancer Drug Des. (1991) 6:647-661.

Mishra et al., "Improved leishmanicidal effect of phosphorothioate antisense oligonucleotides by LDL-medicated delivery" Biochim. Biophys. Acta. (1995) 1264:229-237.

Mitsuhashi, "Strategy for designing specific antisense oligonucleotide sequences" J. Gastroenterology (1997) 32:282-287.

Miura et al., "Fluorometric determination of total mRNA with oligo(dT) immobized on microtiter plates" Clin. Chem. (1996) 42(11) 1758-1764.

Montgomery et al., "RNA as a target of double-stranded RNA-mediated genetic interference in Caenorhabditis elegans" PNAS USA (1998) 95:15502-15507.

New England Biolabs 1998/99 Catalog (cover page and pp. 121 and 284).

Nickerson et al., "Automated DNA diagnostics using an ELISA-based oligonucleotide ligation assay" PNAS (1990) 87:8923-8927.

Nielsen et al., "Sequence-Selective Recognition of DNA by Strand Displacement with a Thymine-Substituted Polyamide" Science (1991)254:1497-1500.

Nowak, "Entering the Postgenome Era" Science (1995)270:368-371.

Oberhauser et al., "Effective incorporation of 2'-O-methyl-oligonucleotides into liposomes and enhanced cell association through modification with thiocholesterol" Nucl. Acids Res. (1992) 20(3):533-538.

Opalinska et al., "Nucleic-Acid Therapeutics: Basic Principles and Recent Applications" Nature Reviews Drug Discovery (2002) 1:503-514.

Patzel et al., "Theoretical design of antisense RNA structures substantially improves annealingkinetics and efficacy in human cells" Nat. Biotechnol (1998) 16(1):64-68.

Prashar et al., "Reads: A Method for Display of 3'-End Fragments of Restriction Enzyme-Digested cDNAs for Analysis of Differential Gene Expression" Methods Enzymol. (1999) 303:258-272.

Rao et al., "elk tissue-specific ets-related genes on chromosomes X and 14 near translocation breakpoints" Science (1989) 244:66-70.

Reddy et al., "Fast Cleavage and Deprotection of Oligonucleotides" Tetrahedron Lett. (1994) 35(25):4311-4314.

Reynolds et al., "Rational siRNA design for RNA interference" Nature Biotechnology (2004) 22(3):326-330.

Rojanasakul, "Antisense oligonucleotide therapeutics: drug delivery and targeting" Advanced Drug Delivery Reviews (1996) 18:115-131.

Saison-Behmoaras et al, "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and their Applications in Antisense Oligonucleotides" Antisense Research and Applications, CRC Press, Boca Raton, Chapter 15 (1993) 273-288.

Santalucia et al., "Improved Nearest-Neighbor Parameters for Predicting DNA Duplex Stability" Biochem. (1996) 35:3555-3562.

Sazani et al., "Systemically delivered antisense oligomers upregulate gene expression in mouse tissues" Nature Biotech (2002) 20:1228-1233.

Sazani et al., "Nuclear antisense effects of neutral, anionic and cationic oligonucleotide analogs" Nucleic Acids Research (2001) 29(19):3965-3974.

Scaringe, "Design and Development of New Protecting Groups for RNA Synthesis" PhD. Thesis, University of Colorado, 1996.

Scaringe et al., "Novel RNA Synthesis Method Using 5'-O-Silyl-2'-O-orthoester Protecting Groups" J. Am. Chem. Soc. (1998) 120:11820-22821.

Schmajuk et al., "Antisense oligonucleotides with different backbones" J. Biol. Chem. (1999) 274(31):21783-21789.

Sczakiel et al., "Computer-aided search for effective antisense RNA target sequences of the human immunodeficiency virus type 1" Antisense Res. & Dev. (1993) 3:45-52.

Serra et al., "Predicting Thermodynamic Properties of RNA" Meth. Enzymol. (1995) 259:242-261.

Sharrocks et al., "The ETS-domain transcription factor family" Int. J. Biochem, Cell Biol. (1997) 29(12):1371-1387.

Shea et al., "Synthesis, hybridization properties and antiviral activity of lipid-oligodeoxynucleotide conjugates" Nucl. Acids Res. (1990) 18(13):3777-3783.

Sierakowska et al., "Repair of thalassemic human B-globin mRNA in mammalian cells by antisense oligonucleotides" PNAS (1996) 93:128401-12844.

Siwkowski et al., "Identification and functional validation of PNAs that inhibit murine CD40 expression by redirection of splicing" Nucleic Acids Research (2004) 32(9):2698.

Smith et al., "Comparison of Biosequences" Adv. Appl. Math (1981) 2:482-489.

Stamenkovic et al., "A B-lymphocyte activation molecule related to the nerve growth factor receptor and induced by cytokines in carcinomas" the EMBO Journal (1989) 8(5):1403-1410.

Stirchak et al., "Uncharged stereoregular nucleic acid analogues: 2. Morpholino nucleoside oligomers with carbamate internucleoside linkages" Nucleic Acid Research (1989) 17(15):6129-6141.

Stull et al., "Predicting antisense oligonucleotide inhibitory efficacy: a computational approach using histograms and thermodynamic indices" Nucleic Acids Res. (1992) 20(13):3501-3508.

Sugimoto et al., "Thermodynamic Parameters to Predict Stability of RNA/DNA Hybrid Duplexes" Biochem. (1995) 34:11211-11216.

Sutcliffe et al., "TOGA: An automated parsing technology for analyzing expression of nearly all genes" PNAS USA (2000) 97:1976-1981.

Svinarchuk et al., "Inhibition of HIV proliferation in MT-4 cells by antisense oligonucleotide conjugated to lipophilic groups" Biochimie (1993) 75:49-54.

Szoka, "Many are probed, but few are chosen" Nature Biotech (1997) 15:509.

Tabara et al., "RNAi in *C. elegans*: Soaking in the Genome Sequence" Science (1998) 282:430-431.

Tijsterman et al., "RNA Helicase MUT-14-Dependent Gene Silencing Triggered in *C. elegans* by Short Antisense RNAs" Science (2002) 295:694-697.

Timmons et al., "Specfic interference by ingested dsRNA" Nature (1998) 395:854.

Timmons et al., "Ingestion of bacterially expressed dsRNAs can produce specific potent genetic interference in *Caenorhabditis elegans*" Gene (2001) 263:103-112.

To, "Identification of Differential Gene Expression by High Throughput Analysis" Comb. Chem. High Throughput Screen. (2000) 3:235-241.

Tone et al., "Regulation of CD40 function by its isoforms generated through alternative splicing" PNAS (2001) 98:1751-1756.

Tuschl et al., "Targeted mRNA degradation by double-stranded RNA in vitro" Genes. Dev. (1999) 13:3191-3197.

Uhlmann et al., "Antisense Oligonucleotides: A New Therapeutic Principle" Chem. Reviews (1990) 90(4):544-584.

Wang et al., "Construction of CD40 antisense RNA and its apoptotic effect on Balm cell" Zhongguo Mian Yi Xue Zazhi (1999) 15: 100. (Abstract).

Wincott et al., "Synthesis, deprotection, analysis and purification of RNA and ribozymes" Nucleic Acids Res. (1995) 23(14):2677-2684.

Xia et al., "Thermodynamic parameters for an expanded nearest-neighbor model for formation of RNA duplexes with Watson-crick base pairs" Biochem (1998) 37:14719-14735.

Zhang et al., "PowerBLAST: A New Network Blast Application for Interactive or Automated Sequence Analysis and Annotation" Genome Res. (1997) 7:649-656.

International Search Report for Application No. PCT/US2008/012998 dated Jun. 8, 2009.

International Search Report for Application No. PCT/US99/08765 dated Oct. 22, 1999.

Partial European Search Report for Application No. 99918757 dated Jul. 13, 2002.

"Analyzing DNA" Genome Analysis—A Laboratory Manuel, Green Ed. (1997) vol. 1, 574-578.

* cited by examiner

SEQUENCE LISTING

```
<160> NUMBER OF SEQ ID NOS: 248

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
ccaggcggca ggaccact                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
gaccaggcgg caggacca                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
aggtgagacc aggcggca                                                 18

<210> SEQ ID NO 4
<211> LENGTH: 18
<212> TYPE: DNA
<213> ORGANISM: Artificial Sequence
<220> FEATURE:
```

-continued

```
<223> OTHER INFORMATION: Synthetic Construct

<400> SEQUENCE: 4
cagaggcaga cgaaccat                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
gcagaggcag acgaacca                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6
gcaagcagcc ccagagga                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
ggtcagcaag cagcccca                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
gacagcggtc agcaagca                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
gatggacagc ggtcagca                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
tctggatgga cagcggtc                                                 18
```

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
ggtggttctg gatggaca                                          18

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
gtgggtggtt ctggatgg                                          18

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
gcagtgggtg gttctgga                                          18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
cacaaagaac agcactga                                          18

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
ctggcacaaa gaacagca                                          18

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
tcctggctgg cacaaaga                                          18

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct

```
<400> SEQUENCE: 17
ctgtcctggc tggcacaa                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
ctcaccagtt tctgtcct                                                 18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
tcactcacca gtttctgt                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
gtgcagtcac tcaccagt                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
actctgtgca gtcactca                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct

<400> SEQUENCE: 22
cagtgaactc tgtgcagt                                                 18

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct

<400> SEQUENCE: 23
attccgtttc agtgaact                                                 18

<210> SEQ ID NO 24
<211> LENGTH: 18
```

-continued

<212> TYPE: DNA
<213> ORGANISM: Artificial Sequence
<220> FEATURE:
<223> OTHER INFORMATION: Synthetic Construct

<400> SEQUENCE: 24
gaaggcattc cgtttcag                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic Construct

<400> SEQUENCE: 25
ttcaccgcaa ggaaggca                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct

<400> SEQUENCE: 26
ctctgttcca ggtgtcta                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic Construct

<400> SEQUENCE: 27
ctggtggcag tgtgtctc                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Construct

<400> SEQUENCE: 28
tggggtcgca gtatttgt                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Construct

<400> SEQUENCE: 29
ggttggggtc gcagtatt                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic Construct

<400> SEQUENCE: 30
ctaggttggg gtcgcagt                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic Construct

<400> SEQUENCE: 31
ggtgcccttc tgctggac                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Construct

<400> SEQUENCE: 32
ctgaggtgcc cttctgct                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic Construct

<400> SEQUENCE: 33
gtgtctgttt ctgaggtg                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetic Construct

<400> SEQUENCE: 34
tggtgtctgt ttctgagg                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthetic Construct

<400> SEQUENCE: 35
acaggtgcag atggtgtc                                                 18

<210> SEQ ID NO 36
<211> LENGTH: 18
<212> TYPE: DNA
<213> ORGANISM: Artificial Sequence
<220> FEATURE:
<223> OTHER INFORMATION: Synthetic Construct

<400> SEQUENCE: 36
ttcacaggtg cagatggt                                                 18

<210> SEQ ID NO 37
<211> LENGTH: 18
<212> TYPE: DNA
<213> ORGANISM: Artificial Sequence

```
<220> FEATURE:
<223> OTHER INFORMATION: Synthetic Construct

<400> SEQUENCE: 37
gtgccagcct tcttcaca                                                 18

<210> SEQ ID NO 38
<211> LENGTH: 18
<212> TYPE: DNA
<213> ORGANISM: Artificial Sequence
<220> FEATURE:
<223> OTHER INFORMATION: Synthetic Construct

<400> SEQUENCE: 38
tacagtgcca gccttctt                                                 18

<210> SEQ ID NO 39
<211> LENGTH: 18
<212> TYPE: DNA
<213> ORGANISM: Artificial Sequence
<220> FEATURE:
<223> OTHER INFORMATION: Synthetic Construct

<400> SEQUENCE: 39
ggacacagct ctcacagg                                                 18

<210> SEQ ID NO 40
<211> LENGTH: 18
<212> TYPE: DNA
<213> ORGANISM: Artificial Sequence
<220> FEATURE:
<223> OTHER INFORMATION: Synthetic Construct

<400> SEQUENCE: 40
tgcaggacac agctctca                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic Construct

<400> SEQUENCE: 41
gagcggtgca ggacacag                                                 18

<210> SEQ ID NO 42
<211> LENGTH: 18
<212> TYPE: DNA
<213> ORGANISM: Artificial Sequence
<220> FEATURE:
<223> OTHER INFORMATION: Synthetic Construct

<400> SEQUENCE: 42
aagccgggcg agcatgag                                                 18

<210> SEQ ID NO 43
<211> LENGTH: 18
<212> TYPE: DNA
<213> ORGANISM: Artificial Sequence
<220> FEATURE:
<223> OTHER INFORMATION: Synthetic Construct

<400> SEQUENCE: 43
aatctgcttg accccaaa                                                 18
```

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct

<400> SEQUENCE: 44
gaaacccctg tagcaatc                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetic Construct

<400> SEQUENCE: 45
gtatcagaaa cccctgta                                                 18

<210> SEQ ID NO 46
<211> LENGTH: 18
<212> TYPE: DNA
<213> ORGANISM: Artificial Sequence
<220> FEATURE:
<223> OTHER INFORMATION: Synthetic Construct

<400> SEQUENCE: 46
gctcgcagat ggtatcag                                                 18

<210> SEQ ID NO 47
<211> LENGTH: 18
<212> TYPE: DNA
<213> ORGANISM: Artificial Sequence
<220> FEATURE:
<223> OTHER INFORMATION: Synthetic Construct

<400> SEQUENCE: 47
gcagggctcg cagatggt                                                 18

<210> SEQ ID NO 48
<211> LENGTH: 18
<212> TYPE: DNA
<213> ORGANISM: Artificial Sequence
<220> FEATURE:
<223> OTHER INFORMATION: Synthetic Construct

<400> SEQUENCE: 48
tgggcagggc tcgcagat                                                 18

<210> SEQ ID NO 49
<211> LENGTH: 18
<212> TYPE: DNA
<213> ORGANISM: Artificial Sequence
<220> FEATURE:
<223> OTHER INFORMATION: Synthetic Construct

<400> SEQUENCE: 49
gactgggcag ggctcgca                                                 18

<210> SEQ ID NO 50
<211> LENGTH: 18
<212> TYPE: DNA
<213> ORGANISM: Artificial Sequence
<220> FEATURE:
<223> OTHER INFORMATION: Synthetic Construct

<400> SEQUENCE: 50
cattggagaa gaagccga                                              18

<210> SEQ ID NO 51
<211> LENGTH: 18
<212> TYPE: DNA
<213> ORGANISM: Artificial Sequence
<220> FEATURE:
<223> OTHER INFORMATION: Synthetic Construct

<400> SEQUENCE: 51
gatgacacat tggagaag                                              18

<210> SEQ ID NO 52
<211> LENGTH: 18
<212> TYPE: DNA
<213> ORGANISM: Artificial Sequence
<220> FEATURE:
<223> OTHER INFORMATION: Synthetic Construct

<400> SEQUENCE: 52
gcagatgaca cattggag                                              18

<210> SEQ ID NO 53
<211> LENGTH: 18
<212> TYPE: DNA
<213> ORGANISM: Artificial Sequence
<220> FEATURE:
<223> OTHER INFORMATION: Synthetic Construct

<400> SEQUENCE: 53
tcgaaagcag atgacaca                                              18

<210> SEQ ID NO 54
<211> LENGTH: 18
<212> TYPE: DNA
<213> ORGANISM: Artificial Sequence
<220> FEATURE:
<223> OTHER INFORMATION: Synthetic Construct

<400> SEQUENCE: 54
gtccaagggt gacatttt                                              18

<210> SEQ ID NO 55
<211> LENGTH: 18
<212> TYPE: DNA
<213> ORGANISM: Artificial Sequence
<220> FEATURE:
<223> OTHER INFORMATION: Synthetic Construct

<400> SEQUENCE: 55
cacagcttgt ccaagggt                                              18

<210> SEQ ID NO 56
<211> LENGTH: 18
<212> TYPE: DNA
<213> ORGANISM: Artificial Sequence
<220> FEATURE:
<223> OTHER INFORMATION: Synthetic Construct

<400> SEQUENCE: 56
ttggtctcac agcttgtc                                              18

<210> SEQ ID NO 57

```
<211> LENGTH: 18
<212> TYPE: DNA
<213> ORGANISM: Artificial Sequence
<220> FEATURE:
<223> OTHER INFORMATION: Synthetic Construct

<400> SEQUENCE: 57
caggtctttg gtctcaca                                                 18

<210> SEQ ID NO 58
<211> LENGTH: 18
<212> TYPE: DNA
<213> ORGANISM: Artificial Sequence
<220> FEATURE:
<223> OTHER INFORMATION: Synthetic Construct

<400> SEQUENCE: 58
ctgttgcaca accaggtc                                                 18

<210> SEQ ID NO 59
<211> LENGTH: 18
<212> TYPE: DNA
<213> ORGANISM: Artificial Sequence
<220> FEATURE:
<223> OTHER INFORMATION: Synthetic Construct

<400> SEQUENCE: 59
gtttgtgcct gcctgttg                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic Construct

<400> SEQUENCE: 60
gtcttgtttg tgcctgcc                                                 18

<210> SEQ ID NO 61
<211> LENGTH: 18
<212> TYPE: DNA
<213> ORGANISM: Artificial Sequence
<220> FEATURE:
<223> OTHER INFORMATION: Synthetic Construct

<400> SEQUENCE: 61
ccacagacaa catcagtc                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic Construct

<400> SEQUENCE: 62
ctggggacca cagacaac                                                 18

<210> SEQ ID NO 63
<211> LENGTH: 18
<212> TYPE: DNA
<213> ORGANISM: Artificial Sequence
<220> FEATURE:
<223> OTHER INFORMATION: Synthetic Construct

<400> SEQUENCE: 63
```
tcagccgatc ctggggac                     18

<210> SEQ ID NO 64
<211> LENGTH: 18
<212> TYPE: DNA
<213> ORGANISM: Artificial Sequence
<220> FEATURE:
<223> OTHER INFORMATION: Synthetic Construct

<400> SEQUENCE: 64
caccaccagg gctctcag                     18

<210> SEQ ID NO 65
<211> LENGTH: 18
<212> TYPE: DNA
<213> ORGANISM: Artificial Sequence
<220> FEATURE:
<223> OTHER INFORMATION: Synthetic Construct

<400> SEQUENCE: 65
gggatcacca ccagggct                     18

<210> SEQ ID NO 66
<211> LENGTH: 18
<212> TYPE: DNA
<213> ORGANISM: Artificial Sequence
<220> FEATURE:
<223> OTHER INFORMATION: Synthetic Construct

<400> SEQUENCE: 66
gaggatggca aacaggat                     18

<210> SEQ ID NO 67
<211> LENGTH: 18
<212> TYPE: DNA
<213> ORGANISM: Artificial Sequence
<220> FEATURE:
<223> OTHER INFORMATION: Synthetic Construct

<400> SEQUENCE: 67
accagcacca agaggatg                     18

<210> SEQ ID NO 68
<211> LENGTH: 18
<212> TYPE: DNA
<213> ORGANISM: Artificial Sequence
<220> FEATURE:
<223> OTHER INFORMATION: Synthetic Construct

<400> SEQUENCE: 68
ttttgataaa gaccagca                     18

<210> SEQ ID NO 69
<211> LENGTH: 18
<212> TYPE: DNA
<213> ORGANISM: Artificial Sequence
<220> FEATURE:
<223> OTHER INFORMATION: Synthetic Construct

<400> SEQUENCE: 69
tattggttgg cttcttgg                     18

<210> SEQ ID NO 70
<211> LENGTH: 18
<212> TYPE: DNA

```
<213> ORGANISM: Artificial Sequence
<220> FEATURE:
<223> OTHER INFORMATION: Synthetic Construct

<400> SEQUENCE: 70
gggttcctgc ttggggtg                                               18

<210> SEQ ID NO 71
<211> LENGTH: 18
<212> TYPE: DNA
<213> ORGANISM: Artificial Sequence
<220> FEATURE:
<223> OTHER INFORMATION: Synthetic Construct

<400> SEQUENCE: 71
gtcgggaaaa ttgatctc                                               18

<210> SEQ ID NO 72
<211> LENGTH: 18
<212> TYPE: DNA
<213> ORGANISM: Artificial Sequence
<220> FEATURE:
<223> OTHER INFORMATION: Synthetic Construct

<400> SEQUENCE: 72
gatcgtcggg aaaattga                                               18

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct

<400> SEQUENCE: 73
ggagccagga agatcgtc                                               18

<210> SEQ ID NO 74
<211> LENGTH: 18
<212> TYPE: DNA
<213> ORGANISM: Artificial Sequence
<220> FEATURE:
<223> OTHER INFORMATION: Synthetic Construct

<400> SEQUENCE: 74
tggagccagg aagatcgt                                               18

<210> SEQ ID NO 75
<211> LENGTH: 18
<212> TYPE: DNA
<213> ORGANISM: Artificial Sequence
<220> FEATURE:
<223> OTHER INFORMATION: Synthetic Construct

<400> SEQUENCE: 75
tggagcagca gtgttgga                                               18

<210> SEQ ID NO 76
<211> LENGTH: 18
<212> TYPE: DNA
<213> ORGANISM: Artificial Sequence
<220> FEATURE:
<223> OTHER INFORMATION: Synthetic Construct

<400> SEQUENCE: 76
gtaaagtctc ctgcactg                                               18
```

<210> SEQ ID NO 77
<211> LENGTH: 18
<212> TYPE: DNA
<213> ORGANISM: Artificial Sequence
<220> FEATURE:
<223> OTHER INFORMATION: Synthetic Construct

<400> SEQUENCE: 77
tggcatccat gtaaagtc                                          18

<210> SEQ ID NO 78
<211> LENGTH: 18
<212> TYPE: DNA
<213> ORGANISM: Artificial Sequence
<220> FEATURE:
<223> OTHER INFORMATION: Synthetic Construct

<400> SEQUENCE: 78
cggttggcat ccatgtaa                                          18

<210> SEQ ID NO 79
<211> LENGTH: 18
<212> TYPE: DNA
<213> ORGANISM: Artificial Sequence
<220> FEATURE:
<223> OTHER INFORMATION: Synthetic Construct

<400> SEQUENCE: 79
ctctttgcca tcctcctg                                          18

<210> SEQ ID NO 80
<211> LENGTH: 18
<212> TYPE: DNA
<213> ORGANISM: Artificial Sequence
<220> FEATURE:
<223> OTHER INFORMATION: Synthetic Construct

<400> SEQUENCE: 80
ctgtctctcc tgcactga                                          18

<210> SEQ ID NO 81
<211> LENGTH: 18
<212> TYPE: DNA
<213> ORGANISM: Artificial Sequence
<220> FEATURE:
<223> OTHER INFORMATION: Synthetic Construct

<400> SEQUENCE: 81
ggtgcagcct cactgtct                                          18

<210> SEQ ID NO 82
<211> LENGTH: 18
<212> TYPE: DNA
<213> ORGANISM: Artificial Sequence
<220> FEATURE:
<223> OTHER INFORMATION: Synthetic Construct

<400> SEQUENCE: 82
aactgcctgt ttgcccac                                          18

<210> SEQ ID NO 83
<211> LENGTH: 18
<212> TYPE: DNA
<213> ORGANISM: Artificial Sequence
<220> FEATURE:

<223> OTHER INFORMATION: Synthetic Construct

<400> SEQUENCE: 83
cttctgcctg cacccctg                                                18

<210> SEQ ID NO 84
<211> LENGTH: 18
<212> TYPE: DNA
<213> ORGANISM: Artificial Sequence
<220> FEATURE:
<223> OTHER INFORMATION: Synthetic Construct

<400> SEQUENCE: 84
actgactggg catagctc                                                18

<210> SEQ ID NO 85
<211> LENGTH: 1004
<212> TYPE: DNA
<213> ORGANISM: Homo sapiens
<300> PUBLICATION INFORMATION:
<301> AUTHORS: Stamenkovic et al.
<302> TITLE: A B-lymphocyte activation molecule related to the nerve
      growth factor receptor and induced by cytokines in carcinomas
<303> JOURNAL: EMBO J.
<304> VOLUME: 8
<305> ISSUE: 5
<306> PAGES: 1403-1410
<307> DATE: 1989
<308> DATABASE ACCESSION NUMBER: X60592
<309> DATABASE ENTRY DATE: 1997-11-14
<313> RELEVANT RESIDUES: (1)..(1004)

<400> SEQUENCE: 85
gcctcgctcg ggcgcccagt ggtcctgccg cctggtctca cctcgccatg gttcgtctgc    60
ctctgcagtg cgtcctctgg ggctgcttgc tgaccgctgt ccatccagaa ccacccactg   120
catgcagaga aaaacagtac ctaataaaca gtcagtgctg ttctttgtgc agccaggac    180
agaaactggt gagtgactgc acagagttca ctgaaacgga atgccttcct tgcggtgaaa   240
gcgaattcct agacacctgg aacagagaga cacactgcca ccagcacaaa tactgcgacc   300
ccaacctagg gcttcgggtc cagcagaagg gcacctcaga aacagacacc atctgcacct   360
gtgaagaagg ctggcactgt acgagtgagg cctgtgagag ctgtgtcctg caccgctcat   420
gctcgcccgg cttttggggtc aagcagattg ctacaggggt ttctgatacc atctgcgagc   480
cctgcccagt cggcttcttc tccaatgtgt catctgcttt cgaaaaatgt caccttgga   540
caagctgtga gaccaaagac ctggttgtgc aacaggcagg cacaaacaag actgatgttg   600
tctgtggtcc ccaggatcgg ctgagagccc tggtggtgat ccccatcatc ttcgggatcc   660
tgtttgccat cctcttggtg ctggtcttta tcaaaaaggt ggccaagaag ccaaccaata   720
aggccccca ccccaagcag gaaccccagg agatcaattt tcccgacgat cttcctggct   780
ccaacactgc tgctccagtg caggagactt tacatggatg ccaaccggtc acccaggagg   840
atggcaaaga gagtcgcatc tcagtgcagg agagacagtg aggctgcacc cacccaggag   900
tgtggccacg tgggcaaaca ggcagttggc cagagagcct ggtgctgctg ctgcaggggt   960
gcaggcagaa gcggggagct atgcccagtc agtgccagcc cctc                   1004

<210> SEQ ID NO 86
<211> LENGTH: 23
<212> TYPE: DNA
<213> ORGANISM: Artificial Sequence
<220> FEATURE:
<223> OTHER INFORMATION: PCR Primer

<400> SEQUENCE: 86
cagagttcac tgaaacggaa tgc						23

<210> SEQ ID NO 87
<211> LENGTH: 23
<212> TYPE: DNA
<213> ORGANISM: Artificial Sequence
<220> FEATURE:
<223> OTHER INFORMATION: PCR Primer

<400> SEQUENCE: 87
ggtggcagtg tgtctctctg ttc						23

<210> SEQ ID NO 88
<211> LENGTH: 25
<212> TYPE: DNA
<213> ORGANISM: Artificial Sequence
<220> FEATURE:
<223> OTHER INFORMATION: PCR Primer

<400> SEQUENCE: 88
ttccttgcgg tgaaagcgaa ttcct						25

<210> SEQ ID NO 89
<211> LENGTH: 19
<212> TYPE: DNA
<213> ORGANISM: Artificial Sequence
<220> FEATURE:
<223> OTHER INFORMATION: PCR Primer

<400> SEQUENCE: 89
gaaggtgaag gtcggagtc						19

<210> SEQ ID NO 90
<211> LENGTH: 20
<212> TYPE: DNA
<213> ORGANISM: Artificial Sequence
<220> FEATURE:
<223> OTHER INFORMATION: PCR Primer

<400> SEQUENCE: 90
gaagatggtg atgggatttc						20

<210> SEQ ID NO 91
<211> LENGTH: 20
<212> TYPE: DNA
<213> ORGANISM: Artificial Sequence
<220> FEATURE:
<223> OTHER INFORMATION: PCR Primer

<400> SEQUENCE: 91
caagcttccc gttctcagcc						20

<210> SEQ ID NO 92
<211> LENGTH: 1579
<212> TYPE: DNA
<213> ORGANISM: Mus musculus

<400> SEQUENCE: 92
tgccctgcat ggtgtctttg cctcggctgt gcgcgctatg gggctgcttg ttgacagcgg      60
tccatctagg gcagtgtgtt acgtgcagtg acaaacagta cctccacgat ggccagtgct     120
gtgatttgtg ccagccagga agccgactga caagccactg cacagctctt gagaagaccc     180

```
aatgccaccc atgtgactca ggcgaattct cagcccagtg gaacagggag attcgctgtc    240
accagcacag acactgtgaa cccaatcaag ggcttcgggt taagaaggag ggcaccgcag    300
aatcagacac tgtctgtacc tgtaaggaag acaacactg caccagcaag gattgcgagg    360
catgtgctca gcacacgccc tgtatccctg gctttggagt tatggagatg gccactgaga    420
ccactgatac cgtctgtcat ccctgcccag tcggcttctt ctccaatcag tcatcacttt    480
tcgaaaagtg ttatccctgg acaagctgtg aggataagaa cttggaggtc ctacagaaag    540
gaacgagtca gactaatgtc atctgtggtt taaagtcccg gatgcgagcc ctgctggtca    600
ttcctgtcgt gatgggcatc ctcatcacca ttttcgtggt gttctctat atcaaaaagg    660 tggtcaagaa accaaaggat aatgagatgt taccccctgc ggctcgacgg caagatcccc    720
aggagatgga agattatccc ggtcataaca ccgctgctcc agtgcaggag acactgcacg    780
ggtgtcagcc tgtcacacag gaggatggta aagagagtcg catctcagtg caggagcggc    840
aggtgacaga cagcatagcc ttgaggcccc tggtctgaac cctggaactg ctttggaggc    900
gatggctgct tgctgacctt tgaagtttga gatgagccaa gacagagccc agtgcagcta    960
actctcatgc ctgcccctg tcatttctca acttgctttt taaggatgga gggaaagctc   1020
gggcatcggg aggtccacag tgatatctac caagtgcagc agtgcaggac ccagagttgt   1080
cttgctgcgg cgttcactgt aaggagtcgt ggctacagga gtccgtggcc cgcagcttgt   1140
gctcgtagag ggcacctggt tgccatcagc agggtactgg ctaaataaat ctgtaattat   1200
ttatacaatg gcatctcaga aactctagca gtgggggcag aaaacaggta gtggaatgat   1260
gggtagagaa acagctttta aaacacattc caaggcaggt aagatggctt ttgtgggtaa   1320
aggagcttgc tgcccaaacc cggttacctg atttttgatcc ctgggacttc atggtaaaag   1380
ggagagaacc aaatccagag ggttgtcatt tgacctccat gtgtgctctg tggtaatgta   1440 cccgtgtgt gcacatgtgc acatatccta aatggatgt ggtggtgtat tgtagaaatt   1500
atttaatccg ccctgggttt ctacctgtgt gttaccattt agttcttgaa taaagacaca   1560
ctcaaccttt atatttaca                                                 1579
```

<210> SEQ ID NO 93
<211> LENGTH: 27
<212> TYPE: DNA
<213> ORGANISM: Artificial Sequence
<220> FEATURE:
<223> OTHER INFORMATION: PCR Primer

<400> SEQUENCE: 93
tgatatagag aaacacccccg aaaatgg                            27

<210> SEQ ID NO 94
<211> LENGTH: 27
<212> TYPE: DNA
<213> ORGANISM: Artificial Sequence
<220> FEATURE:
<223> OTHER INFORMATION: PCR Primer

<400> SEQUENCE: 94
gccactgaga ccactgatac cgtctgt                            27

<210> SEQ ID NO 95
<211> LENGTH: 20
<212> TYPE: DNA
<213> ORGANISM: Artificial Sequence
<220> FEATURE:
<223> OTHER INFORMATION: PCR Primer

```
<400> SEQUENCE: 95
gccagtacac ctgccacaaa                                              20

<210> SEQ ID NO 96
<211> LENGTH: 24
<212> TYPE: DNA
<213> ORGANISM: Artificial Sequence
<220> FEATURE:
<223> OTHER INFORMATION: PCR Primer

<400> SEQUENCE: 96
gaccaaattc cattttcctt cttg                                         24

<210> SEQ ID NO 97
<211> LENGTH: 28
<212> TYPE: DNA
<213> ORGANISM: Artificial Sequence
<220> FEATURE:
<223> OTHER INFORMATION: PCR Primer

<400> SEQUENCE: 97
aggcgagact ctgagccact cacatctg                                     28

<210> SEQ ID NO 98
<211> LENGTH: 20
<212> TYPE: DNA
<213> ORGANISM: Artificial Sequence
<220> FEATURE:
<223> OTHER INFORMATION: PCR Primer

<400> SEQUENCE: 98
ctgcatgtcc ggaggaaatt                                              20

<210> SEQ ID NO 99
<211> LENGTH: 19
<212> TYPE: DNA
<213> ORGANISM: Artificial Sequence
<220> FEATURE:
<223> OTHER INFORMATION: PCR Primer

<400> SEQUENCE: 99
agccatcgtc tgtggcaaa                                               19

<210> SEQ ID NO 100
<211> LENGTH: 22
<212> TYPE: DNA
<213> ORGANISM: Artificial Sequence
<220> FEATURE:
<223> OTHER INFORMATION: PCR Primer

<400> SEQUENCE: 100
ctggcgcaat gtcacgaggc tg                                           22

<210> SEQ ID NO 101
<211> LENGTH: 23
<212> TYPE: DNA
<213> ORGANISM: Artificial Sequence
<220> FEATURE:
<223> OTHER INFORMATION: PCR Primer

<400> SEQUENCE: 101
cactgatacc gtctgtcatc cct                                          23

<210> SEQ ID NO 102
```

```
<211> LENGTH: 25
<212> TYPE: DNA
<213> ORGANISM: Artificial Sequence
<220> FEATURE:
<223> OTHER INFORMATION: PCR Primer

<400> SEQUENCE: 102
agttcttatc ctcacagctt gtcca                                            25

<210> SEQ ID NO 103
<211> LENGTH: 31
<212> TYPE: DNA
<213> ORGANISM: Artificial Sequence
<220> FEATURE:
<223> OTHER INFORMATION: PCR Primer

<400> SEQUENCE: 103
agtcggcttc ttctccaatc agtcatcact t                                     31

<210> SEQ ID NO 104
<211> LENGTH: 23
<212> TYPE: DNA
<213> ORGANISM: Artificial Sequence
<220> FEATURE:
<223> OTHER INFORMATION: PCR Primer

<400> SEQUENCE: 104
cactgatacc gtctgtcatc cct                                              23

<210> SEQ ID NO 105
<211> LENGTH: 25
<212> TYPE: DNA
<213> ORGANISM: Artificial Sequence
<220> FEATURE:
<223> OTHER INFORMATION: PCR Primer

<400> SEQUENCE: 105
ccacatccgg gactttaaac cttgt                                            25

<210> SEQ ID NO 106
<211> LENGTH: 27
<212> TYPE: DNA
<213> ORGANISM: Artificial Sequence
<220> FEATURE:
<223> OTHER INFORMATION: PCR Primer

<400> SEQUENCE: 106
ccagtcggct tcttctccaa tcagtca                                          27

<210> SEQ ID NO 107
<211> LENGTH: 24
<212> TYPE: DNA
<213> ORGANISM: Artificial Sequence
<220> FEATURE:
<223> OTHER INFORMATION: PCR Primer

<400> SEQUENCE: 107
tgtgttacgt gcagtgacaa acag                                             24

<210> SEQ ID NO 108
<211> LENGTH: 18
<212> TYPE: DNA
<213> ORGANISM: Artificial Sequence
<220> FEATURE:
<223> OTHER INFORMATION: PCR Primer

<400> SEQUENCE: 108
```
gcttcctggc tggcacaa                                                     18

<210> SEQ ID NO 109
<211> LENGTH: 23
<212> TYPE: DNA
<213> ORGANISM: Artificial Sequence
<220> FEATURE:
<223> OTHER INFORMATION: PCR Primer

<400> SEQUENCE: 109
cctccacgat cgccagtgct gtg                                               23

<210> SEQ ID NO 110
<211> LENGTH: 15
<212> TYPE: DNA
<213> ORGANISM: Artificial Sequence
<220> FEATURE:
<223> OTHER INFORMATION: PCR Primer

<400> SEQUENCE: 110
tcgccgcttg ctgca                                                        15

<210> SEQ ID NO 111
<211> LENGTH: 17
<212> TYPE: DNA
<213> ORGANISM: Artificial Sequence
<220> FEATURE:
<223> OTHER INFORMATION: PCR Primer

<400> SEQUENCE: 111
atcggccgtg atgtcga                                                      17

<210> SEQ ID NO 112
<211> LENGTH: 23
<212> TYPE: DNA
<213> ORGANISM: Artificial Sequence
<220> FEATURE:
<223> OTHER INFORMATION: PCR Primer

<400> SEQUENCE: 112
ccatggtcaa ccccaccgtg ttc                                               23

<210> SEQ ID NO 113
<211> LENGTH: 15
<212> TYPE: DNA
<213> ORGANISM: Artificial Sequence
<220> FEATURE:
<223> OTHER INFORMATION: Synthetic Construct

<400> SEQUENCE: 113
gctagtcact gagca                                                        15

<210> SEQ ID NO 114
<211> LENGTH: 15
<212> TYPE: DNA
<213> ORGANISM: Artificial Sequence
<220> FEATURE:
<223> OTHER INFORMATION: Synthetic Construct

<400> SEQUENCE: 114
caaagtccct gctag                                                        15

<210> SEQ ID NO 115
<211> LENGTH: 15
<212> TYPE: DNA

```
<213> ORGANISM: Artificial Sequence
<220> FEATURE:
<223> OTHER INFORMATION: Synthetic Construct

<400> SEQUENCE: 115
agccacaagt cactc                                                      15

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
agacaccatc gcag                                                       14

<210> SEQ ID NO 117
<211> LENGTH: 15
<212> TYPE: DNA
<213> ORGANISM: Artificial Sequence
<220> FEATURE:
<223> OTHER INFORMATION: Synthetic Construct

<400> SEQUENCE: 117
gcgagatcag aagag                                                      15

<210> SEQ ID NO 118
<211> LENGTH: 15
<212> TYPE: DNA
<213> ORGANISM: Artificial Sequence
<220> FEATURE:
<223> OTHER INFORMATION: Synthetic Construct

<400> SEQUENCE: 118
cgctgtcaac aagca                                                      15

<210> SEQ ID NO 119
<211> LENGTH: 15
<212> TYPE: DNA
<213> ORGANISM: Artificial Sequence
<220> FEATURE:
<223> OTHER INFORMATION: Synthetic Construct

<400> SEQUENCE: 119
ctgccctaga tggac                                                      15

<210> SEQ ID NO 120
<211> LENGTH: 15
<212> TYPE: DNA
<213> ORGANISM: Artificial Sequence
<220> FEATURE:
<223> OTHER INFORMATION: Synthetic Construct

<400> SEQUENCE: 120
ctggctggca caaat                                                      15

<210> SEQ ID NO 121
<211> LENGTH: 15
<212> TYPE: DNA
<213> ORGANISM: Artificial Sequence
<220> FEATURE:
<223> OTHER INFORMATION: Synthetic Construct

<400> SEQUENCE: 121
tgggttcaca gtgtc                                                      15
```

```
<210> SEQ ID NO 122
<211> LENGTH: 15
<212> TYPE: DNA
<213> ORGANISM: Artificial Sequence
<220> FEATURE:
<223> OTHER INFORMATION: Synthetic Construct

<400> SEQUENCE: 122
catctccata actcc                                                    15

<210> SEQ ID NO 123
<211> LENGTH: 15
<212> TYPE: DNA
<213> ORGANISM: Artificial Sequence
<220> FEATURE:
<223> OTHER INFORMATION: Synthetic Construct

<400> SEQUENCE: 123
cttgtccagg gataa                                                    15

<210> SEQ ID NO 124
<211> LENGTH: 15
<212> TYPE: DNA
<213> ORGANISM: Artificial Sequence
<220> FEATURE:
<223> OTHER INFORMATION: PNA Oligomer

<400> SEQUENCE: 124
cacagatgac attag                                                    15

<210> SEQ ID NO 125
<211> LENGTH: 15
<212> TYPE: DNA
<213> ORGANISM: Artificial Sequence
<220> FEATURE:
<223> OTHER INFORMATION: Synthetic Construct

<400> SEQUENCE: 125
tgatatagag aaaca                                                    15

<210> SEQ ID NO 126
<211> LENGTH: 15
<212> TYPE: DNA
<213> ORGANISM: Artificial Sequence
<220> FEATURE:
<223> OTHER INFORMATION: Synthetic Construct

<400> SEQUENCE: 126
tcttgaccac ctttt                                                    15

<210> SEQ ID NO 127
<211> LENGTH: 15
<212> TYPE: DNA
<213> ORGANISM: Artificial Sequence
<220> FEATURE:
<223> OTHER INFORMATION: Synthetic Construct

<400> SEQUENCE: 127
ctcattatcc tttgg                                                    15

<210> SEQ ID NO 128
<211> LENGTH: 13
<212> TYPE: DNA
<213> ORGANISM: Artificial Sequence
<220> FEATURE:
```

<223> OTHER INFORMATION: Synthetic Construct

<400> SEQUENCE: 128
ggttcagacc agg                                                          13

<210> SEQ ID NO 129
<211> LENGTH: 15
<212> TYPE: DNA
<213> ORGANISM: Artificial Sequence
<220> FEATURE:
<223> OTHER INFORMATION: Synthetic Construct

<400> SEQUENCE: 129
aaacttcaaa ggtca                                                        15

<210> SEQ ID NO 130
<211> LENGTH: 15
<212> TYPE: DNA
<213> ORGANISM: Artificial Sequence
<220> FEATURE:
<223> OTHER INFORMATION: Synthetic Construct

<400> SEQUENCE: 130
tttatttagc cagta                                                        15

<210> SEQ ID NO 131
<211> LENGTH: 15
<212> TYPE: DNA
<213> ORGANISM: Artificial Sequence
<220> FEATURE:
<223> OTHER INFORMATION: Synthetic Construct

<400> SEQUENCE: 131
agccccacgc actgg                                                        15

<210> SEQ ID NO 132
<211> LENGTH: 938
<212> TYPE: DNA
<213> ORGANISM: Mus musculus

<400> SEQUENCE: 132
gcctcctggc ccttcagctg tggtctttcc cgttttctga ctttgcggtg acactgggga      60
cttccttaga cctctctgga gacgctttcg gttctgcaga gattcccagg ggtattgtgg     120
gtggggtggg gtaacaatag tgtccctgtg gcgctcccag tccctatagt aatccttcac     180
ccctctgcta tcttgcaatc aggagagtcc ttagccctgc tataggtggc ttttgaggtc     240
ctggatgcga ggaggggggac tggggggtgg gtcgggtaat gtaagaaaag ggctcctttt     300
gggaccctgg ctcctccagc caccttggtg cccatccctt aaactcttgg ggacaatcag     360
actcctggga aggtcctggg gaaatccctg ctcagtgact agccataggc ccaccgcgat     420
tggtgcccga agacccgcc ctcttcctgg gcgggactcc tagcagggac tttggagtga     480
cttgtggctt cagcaggagc cctgtgattt ggctcttctg atctcgccct gcgatggtgt     540
cttgccctcg gctgtgcgcg ctatgggct gcttgttgac agcggtgagt ggcttgtgtt     600
ctaacctcca agggagttag ggcttagaga gtgagagatg gaaagaggaa agaggagaca     660
agactttgga gatgagagat cttcctactg gaagcggcgg ttagtaggat gggcaagatc     720
tctcgcgtct tgacacacac acacacacac acaaatgagg tgggctgctc ctctttcctt     780
ccagaaggtc ggggttctgt tccacgaagc ccacagggaa ccttagggag ggcattcctc     840
cacagcggtg cctggacagc tttgtctgac ccaagccttg ctccggagct gactgcagag     900
actggaaagg gttagcagac aggaagcctg gctggggg                          938

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(20)
<223> OTHER INFORMATION: n is a, c, g, or t

<400> SEQUENCE: 133
nnnnnnnnnn nnnnnnnnnn                                              20

<210> SEQ ID NO 134
<211> LENGTH: 18
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(4)
<223> OTHER INFORMATION: 2'-O-methoxyethyl gapmer with phosphorothioate
      backbone
<220> FEATURE:
<221> NAME/KEY: misc_feature
<222> LOCATION: (15)..(18)
<223> OTHER INFORMATION: 2'-O-methoxyethyl gapmer with phosphorothioate
      backbone

<400> SEQUENCE: 134
tctcactcct atcccagt                                                18

<210> SEQ ID NO 135
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 135
cactgatcag ataag                                                   15

<210> SEQ ID NO 136
<211> LENGTH: 15
<212> TYPE: DNA
<213> ORGANISM: Artificial Sequence
<220> FEATURE:
<223> OTHER INFORMATION: PNA Oligomer

<400> SEQUENCE: 136
actagtgcta gcgtc                                                   15

<210> SEQ ID NO 137
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 137
cgtcatgata ccgat                                                   15

<210> SEQ ID NO 138

```
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine-NH2

<400> SEQUENCE: 138
attagtctga ctcgt                                                15

<210> SEQ ID NO 139
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine-NH2

<400> SEQUENCE: 139
acattagtct gactc                                                15

<210> SEQ ID NO 140
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 140
tgacattagt ctgac                                                15

<210> SEQ ID NO 141
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 141
gatgacatta gtctg                                                15
```

```
<210> SEQ ID NO 142
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 142
cagatgacat tagtc                                                    15

<210> SEQ ID NO 143
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 143
ctggactcac cacag                                                    15

<210> SEQ ID NO 144
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 144
ggactcacca cagat                                                    15

<210> SEQ ID NO 145
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 145
actcaccaca gatga                                                    15
```

```
<210> SEQ ID NO 146
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 146
tcaccacaga tgaca                                                    15

<210> SEQ ID NO 147
<211> LENGTH: 15
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (15)..(15)
<223> OTHER INFORMATION: Lysine

<400> SEQUENCE: 147
accacagatg acatt                                                    15

<210> SEQ ID NO 148
<211> LENGTH: 7
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (7)..(7)
<223> OTHER INFORMATION: Lysine

<400> SEQUENCE: 148 acattag                                                              7

<210> SEQ ID NO 149
<211> LENGTH: 8
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (8)..(8)
<223> OTHER INFORMATION: Lysine

<400> SEQUENCE: 149 gacattag                                                             8
```

```
<210> SEQ ID NO 150
<211> LENGTH: 9
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (9)..(9)
<223> OTHER INFORMATION: Lysine

<400> SEQUENCE: 150 tgacattag                                                                     9

<210> SEQ ID NO 151
<211> LENGTH: 10
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (10)..(10)
<223> OTHER INFORMATION: Lysine

<400> SEQUENCE: 151
atgacattag                                                                    10

<210> SEQ ID NO 152
<211> LENGTH: 11
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (11)..(11)
<223> OTHER INFORMATION: Lysine

<400> SEQUENCE: 152
gatgacatta g                                                                  11

<210> SEQ ID NO 153
<211> LENGTH: 12
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (12)..(12)
<223> OTHER INFORMATION: Lysine

<400> SEQUENCE: 153
```
agatgacatt ag  12

<210> SEQ ID NO 154
<211> LENGTH: 13
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (13)..(13)
<223> OTHER INFORMATION: Lysine

<400> SEQUENCE: 154
cagatgacat tag  13

<210> SEQ ID NO 155
<211> LENGTH: 14
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (14)..(14)
<223> OTHER INFORMATION: Lysine

<400> SEQUENCE: 155
acagatgaca ttag  14

<210> SEQ ID NO 156
<211> LENGTH: 16
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (16)..(16)
<223> OTHER INFORMATION: Lysine

<400> SEQUENCE: 156
ccacagatga cattag  16

<210> SEQ ID NO 157
<211> LENGTH: 17
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (17)..(17)
<223> OTHER INFORMATION: Lysine

<400> SEQUENCE: 157

```
accacagatg acattag                                                    17

<210> SEQ ID NO 158
<211> LENGTH: 18
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (18)..(18)
<223> OTHER INFORMATION: Lysine

<400> SEQUENCE: 158
caccacagat gacattag                                                   18

<210> SEQ ID NO 159
<211> LENGTH: 19
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (19)..(19)
<223> OTHER INFORMATION: Lysine

<400> SEQUENCE: 159
tcaccacaga tgacattag                                                  19

<210> SEQ ID NO 160
<211> LENGTH: 20
<212> TYPE: DNA
<213> ORGANISM: Artificial Sequence
<220> FEATURE:
<223> OTHER INFORMATION: PNA Oligomer
<220> FEATURE:
<221> NAME/KEY: misc_feature
<222> LOCATION: (1)..(1)
<223> OTHER INFORMATION: L-histidine
<220> FEATURE:
<221> NAME/KEY: misc_feature
<222> LOCATION: (20)..(20)
<223> OTHER INFORMATION: Lysine

<400> SEQUENCE: 160
ctcaccacag atgacattag                                                 20

<210> SEQ ID NO 161
<211> LENGTH: 19
<212> TYPE: DNA
<213> ORGANISM: Artificial Sequence
<220> FEATURE:
<223> OTHER INFORMATION: Synthetic Construct

<400> SEQUENCE: 161
cgagaggcgg acgggaccg                                                  19

<210> SEQ ID NO 162
<211> LENGTH: 21
<212> TYPE: DNA
```

<210> SEQ ID NO 162
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: two-nucleobase overhang of deoxythymidine (dT)

<400> SEQUENCE: 162
cgagaggcgg acgggaccgt t                                      21

<210> SEQ ID NO 163
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: two-nucleobase ovrhang of deoxythymidine (dT)

<400> SEQUENCE: 163
cggtcccgtc cgcctctcgt t                                      21

<210> SEQ ID NO 164
<211> LENGTH: 19
<212> TYPE: DNA
<213> ORGANISM: Artificial Sequence
<220> FEATURE:
<223> OTHER INFORMATION: Synthetic Construct

<400> SEQUENCE: 164
cggtcccgtc cgcctctcg                                         19

<210> SEQ ID NO 165
<211> LENGTH: 18
<212> TYPE: DNA
<213> ORGANISM: Artificial Sequence
<220> FEATURE:
<223> OTHER INFORMATION: Synthetic Construct

<400> SEQUENCE: 165
agtggtcctg ccgcctgg                                          18

<210> SEQ ID NO 166
<211> LENGTH: 18
<212> TYPE: DNA
<213> ORGANISM: Artificial Sequence
<220> FEATURE:
<223> OTHER INFORMATION: Synthetic Construct

<400> SEQUENCE: 166
tggtcctgcc gcctggtc                                          18

<210> SEQ ID NO 167
<211> LENGTH: 18
<212> TYPE: DNA
<213> ORGANISM: Artificial Sequence
<220> FEATURE:
<223> OTHER INFORMATION: Synthetic Construct

<400> SEQUENCE: 167
tgccgcctgg tctcacct                                          18

<210> SEQ ID NO 168
<211> LENGTH: 18

```
<212> TYPE: DNA
<213> ORGANISM: Artificial Sequence
<220> FEATURE:
<223> OTHER INFORMATION: Synthetic Construct

<400> SEQUENCE: 168
atggttcgtc tgcctctg                                                    18

<210> SEQ ID NO 169
<211> LENGTH: 17
<212> TYPE: DNA
<213> ORGANISM: Artificial Sequence
<220> FEATURE:
<223> OTHER INFORMATION: Synthetic Construct

<400> SEQUENCE: 169
tggttcgtct gctctgc                                                     17

<210> SEQ ID NO 170
<211> LENGTH: 18
<212> TYPE: DNA
<213> ORGANISM: Artificial Sequence
<220> FEATURE:
<223> OTHER INFORMATION: Synthetic Construct

<400> SEQUENCE: 170
tcctctgggg ctgcttgc                                                    18

<210> SEQ ID NO 171
<211> LENGTH: 18
<212> TYPE: DNA
<213> ORGANISM: Artificial Sequence
<220> FEATURE:
<223> OTHER INFORMATION: Synthetic Construct

<400> SEQUENCE: 171
tggggctgct tgctgacc                                                    18

<210> SEQ ID NO 172
<211> LENGTH: 18
<212> TYPE: DNA
<213> ORGANISM: Artificial Sequence
<220> FEATURE:
<223> OTHER INFORMATION: Synthetic Construct

<400> SEQUENCE: 172
tgcttgctga ccgctgtc                                                    18

<210> SEQ ID NO 173
<211> LENGTH: 18
<212> TYPE: DNA
<213> ORGANISM: Artificial Sequence
<220> FEATURE:
<223> OTHER INFORMATION: Synthetic Construct

<400> SEQUENCE: 173
tgctgaccgc tgtccatc                                                    18

<210> SEQ ID NO 174
<211> LENGTH: 19
<212> TYPE: DNA
<213> ORGANISM: Artificial Sequence
<220> FEATURE:
<223> OTHER INFORMATION: Synthetic Construct

<400> SEQUENCE: 174
```

-continued

| | |
|---|---|
| gaccgctgtc cactccaga | 19 |

<210> SEQ ID NO 175
<211> LENGTH: 18
<212> TYPE: DNA
<213> ORGANISM: Artificial Sequence
<220> FEATURE:
<223> OTHER INFORMATION: Synthetic Construct

<400> SEQUENCE: 175

| | |
|---|---|
| tgtccatcca gaaccacc | 18 |

<210> SEQ ID NO 176
<211> LENGTH: 18
<212> TYPE: DNA
<213> ORGANISM: Artificial Sequence
<220> FEATURE:
<223> OTHER INFORMATION: Synthetic Construct

<400> SEQUENCE: 176

| | |
|---|---|
| ccatccagaa ccacccac | 18 |

<210> SEQ ID NO 177
<211> LENGTH: 18
<212> TYPE: DNA
<213> ORGANISM: Artificial Sequence
<220> FEATURE:
<223> OTHER INFORMATION: Synthetic Construct

<400> SEQUENCE: 177

| | |
|---|---|
| tccagaacca cccactgc | 18 |

<210> SEQ ID NO 178
<211> LENGTH: 18
<212> TYPE: DNA
<213> ORGANISM: Artificial Sequence
<220> FEATURE:
<223> OTHER INFORMATION: Synthetic Construct

<400> SEQUENCE: 178

| | |
|---|---|
| tcagtgctgt tctttgtg | 18 |

<210> SEQ ID NO 179
<211> LENGTH: 18
<212> TYPE: DNA
<213> ORGANISM: Artificial Sequence
<220> FEATURE:
<223> OTHER INFORMATION: Synthetic Construct

<400> SEQUENCE: 179

| | |
|---|---|
| tgctgttctt tgtgccag | 18 |

<210> SEQ ID NO 180
<211> LENGTH: 18
<212> TYPE: DNA
<213> ORGANISM: Artificial Sequence
<220> FEATURE:
<223> OTHER INFORMATION: Synthetic Construct

<400> SEQUENCE: 180

| | |
|---|---|
| tctttgtgcc agccagga | 18 |

<210> SEQ ID NO 181
<211> LENGTH: 18
<212> TYPE: DNA
<213> ORGANISM: Artificial Sequence

```
<220> FEATURE:
<223> OTHER INFORMATION: Synthetic Construct

<400> SEQUENCE: 181
ttgtgccagc caggacag                                                18

<210> SEQ ID NO 182
<211> LENGTH: 18
<212> TYPE: DNA
<213> ORGANISM: Artificial Sequence
<220> FEATURE:
<223> OTHER INFORMATION: Synthetic Construct

<400> SEQUENCE: 182
aggacagaaa ctggtgag                                                18

<210> SEQ ID NO 183
<211> LENGTH: 18
<212> TYPE: DNA
<213> ORGANISM: Artificial Sequence
<220> FEATURE:
<223> OTHER INFORMATION: Synthetic Construct

<400> SEQUENCE: 183
acagaaactg gtgagtga                                                18

<210> SEQ ID NO 184
<211> LENGTH: 18
<212> TYPE: DNA
<213> ORGANISM: Artificial Sequence
<220> FEATURE:
<223> OTHER INFORMATION: Synthetic Construct

<400> SEQUENCE: 184
actggtgagt gactgcac                                                18

<210> SEQ ID NO 185
<211> LENGTH: 18
<212> TYPE: DNA
<213> ORGANISM: Artificial Sequence
<220> FEATURE:
<223> OTHER INFORMATION: Synthetic Construct

<400> SEQUENCE: 185
tgagtgactg cacagagt                                                18

<210> SEQ ID NO 186
<211> LENGTH: 18
<212> TYPE: DNA
<213> ORGANISM: Artificial Sequence
<220> FEATURE:
<223> OTHER INFORMATION: Synthetic Construct

<400> SEQUENCE: 186
actgcacaga gttcactg                                                18

<210> SEQ ID NO 187
<211> LENGTH: 18
<212> TYPE: DNA
<213> ORGANISM: Artificial Sequence
<220> FEATURE:
<223> OTHER INFORMATION: Synthetic Construct

<400> SEQUENCE: 187
agttcactga aacggaat                                                18
```

```
<210> SEQ ID NO 188
<211> LENGTH: 18
<212> TYPE: DNA
<213> ORGANISM: Artificial Sequence
<220> FEATURE:
<223> OTHER INFORMATION: Synthetic Construct

<400> SEQUENCE: 188
ctgaaacgga atgccttc                                                       18

<210> SEQ ID NO 189
<211> LENGTH: 18
<212> TYPE: DNA
<213> ORGANISM: Artificial Sequence
<220> FEATURE:
<223> OTHER INFORMATION: Synthetic Construct

<400> SEQUENCE: 189
tgccttcctt gcggtgaa                                                       18

<210> SEQ ID NO 190
<211> LENGTH: 18
<212> TYPE: DNA
<213> ORGANISM: Artificial Sequence
<220> FEATURE:
<223> OTHER INFORMATION: Synthetic Construct

<400> SEQUENCE: 190
tagacacctg gaacagag                                                       18

<210> SEQ ID NO 191
<211> LENGTH: 18
<212> TYPE: DNA
<213> ORGANISM: Artificial Sequence
<220> FEATURE:
<223> OTHER INFORMATION: Synthetic Construct

<400> SEQUENCE: 191
gagacacact gccaccag                                                       18

<210> SEQ ID NO 192
<211> LENGTH: 18
<212> TYPE: DNA
<213> ORGANISM: Artificial Sequence
<220> FEATURE:
<223> OTHER INFORMATION: Synthetic Construct

<400> SEQUENCE: 192
acaaatactg cgacccca                                                       18

<210> SEQ ID NO 193
<211> LENGTH: 18
<212> TYPE: DNA
<213> ORGANISM: Artificial Sequence
<220> FEATURE:
<223> OTHER INFORMATION: Synthetic Construct

<400> SEQUENCE: 193
aatactgcga ccccaacc                                                       18

<210> SEQ ID NO 194
<211> LENGTH: 18
<212> TYPE: DNA
<213> ORGANISM: Artificial Sequence
<220> FEATURE:
<223> OTHER INFORMATION: Synthetic Construct
```

<400> SEQUENCE: 194
actgcgaccc caacctag                    18

<210> SEQ ID NO 195
<211> LENGTH: 18
<212> TYPE: DNA
<213> ORGANISM: Artificial Sequence
<220> FEATURE:
<223> OTHER INFORMATION: Synthetic Construct

<400> SEQUENCE: 195
gtccagcaga agggcacc                    18

<210> SEQ ID NO 196
<211> LENGTH: 18
<212> TYPE: DNA
<213> ORGANISM: Artificial Sequence
<220> FEATURE:
<223> OTHER INFORMATION: Synthetic Construct

<400> SEQUENCE: 196
agcagaaggg cacctcag                    18

<210> SEQ ID NO 197
<211> LENGTH: 18
<212> TYPE: DNA
<213> ORGANISM: Artificial Sequence
<220> FEATURE:
<223> OTHER INFORMATION: Synthetic Construct

<400> SEQUENCE: 197
cacctcagaa acagacac                    18

<210> SEQ ID NO 198
<211> LENGTH: 18
<212> TYPE: DNA
<213> ORGANISM: Artificial Sequence
<220> FEATURE:
<223> OTHER INFORMATION: Synthetic Construct

<400> SEQUENCE: 198
cctcagaaac agacacca                    18

<210> SEQ ID NO 199
<211> LENGTH: 18
<212> TYPE: DNA
<213> ORGANISM: Artificial Sequence
<220> FEATURE:
<223> OTHER INFORMATION: Synthetic Construct

<400> SEQUENCE: 199
gacaccatct gcacctgt                    18

<210> SEQ ID NO 200
<211> LENGTH: 18
<212> TYPE: DNA
<213> ORGANISM: Artificial Sequence
<220> FEATURE:
<223> OTHER INFORMATION: Synthetic Construct

<400> SEQUENCE: 200
accatctgca cctgtgaa                    18

<210> SEQ ID NO 201

```
<211> LENGTH: 18
<212> TYPE: DNA
<213> ORGANISM: Artificial Sequence
<220> FEATURE:
<223> OTHER INFORMATION: Synthetic Construct

<400> SEQUENCE: 201
tgtgaagaag gctggcac                                                 18

<210> SEQ ID NO 202
<211> LENGTH: 18
<212> TYPE: DNA
<213> ORGANISM: Artificial Sequence
<220> FEATURE:
<223> OTHER INFORMATION: Synthetic Construct

<400> SEQUENCE: 202
aagaaggctg gcactgta                                                 18

<210> SEQ ID NO 203
<211> LENGTH: 18
<212> TYPE: DNA
<213> ORGANISM: Artificial Sequence
<220> FEATURE:
<223> OTHER INFORMATION: Synthetic Construct

<400> SEQUENCE: 203
cctgtgagag ctgtgtcc                                                 18

<210> SEQ ID NO 204
<211> LENGTH: 18
<212> TYPE: DNA
<213> ORGANISM: Artificial Sequence
<220> FEATURE:
<223> OTHER INFORMATION: Synthetic Construct

<400> SEQUENCE: 204
tgagagctgt gtcctgca                                                 18

<210> SEQ ID NO 205
<211> LENGTH: 18
<212> TYPE: DNA
<213> ORGANISM: Artificial Sequence
<220> FEATURE:
<223> OTHER INFORMATION: Synthetic Construct

<400> SEQUENCE: 205
ctgtgtcctg caccgctc                                                 18

<210> SEQ ID NO 206
<211> LENGTH: 18
<212> TYPE: DNA
<213> ORGANISM: Artificial Sequence
<220> FEATURE:
<223> OTHER INFORMATION: Synthetic Construct

<400> SEQUENCE: 206
ctcatgctcg cccggctt                                                 18

<210> SEQ ID NO 207
<211> LENGTH: 18
<212> TYPE: DNA
<213> ORGANISM: Artificial Sequence
<220> FEATURE:
<223> OTHER INFORMATION: Synthetic Construct

<400> SEQUENCE: 207
```

```
tttggggtca agcagatt                                          18
```

<210> SEQ ID NO 208
<211> LENGTH: 18
<212> TYPE: DNA
<213> ORGANISM: Artificial Sequence
<220> FEATURE:
<223> OTHER INFORMATION: Synthetic Construct

<400> SEQUENCE: 208

```
gattgctaca ggggtttc                                          18
```

<210> SEQ ID NO 209
<211> LENGTH: 18
<212> TYPE: DNA
<213> ORGANISM: Artificial Sequence
<220> FEATURE:
<223> OTHER INFORMATION: Synthetic Construct

<400> SEQUENCE: 209

```
tacaggggtt tctgatac                                          18
```

<210> SEQ ID NO 210
<211> LENGTH: 18
<212> TYPE: DNA
<213> ORGANISM: Artificial Sequence
<220> FEATURE:
<223> OTHER INFORMATION: Synthetic Construct

<400> SEQUENCE: 210

```
ctgataccat ctgcgagc                                          18
```

<210> SEQ ID NO 211
<211> LENGTH: 18
<212> TYPE: DNA
<213> ORGANISM: Artificial Sequence
<220> FEATURE:
<223> OTHER INFORMATION: Synthetic Construct

<400> SEQUENCE: 211

```
accatctgcg agccctgc                                          18
```

<210> SEQ ID NO 212
<211> LENGTH: 18
<212> TYPE: DNA
<213> ORGANISM: Artificial Sequence
<220> FEATURE:
<223> OTHER INFORMATION: Synthetic Construct

<400> SEQUENCE: 212

```
atctgcgagc cctgccca                                          18
```

<210> SEQ ID NO 213
<211> LENGTH: 18
<212> TYPE: DNA
<213> ORGANISM: Artificial Sequence
<220> FEATURE:
<223> OTHER INFORMATION: Synthetic Construct

<400> SEQUENCE: 213

```
tgcgagccct gcccagtc                                          18
```

<210> SEQ ID NO 214
<211> LENGTH: 18
<212> TYPE: DNA

```
<213> ORGANISM: Artificial Sequence
<220> FEATURE:
<223> OTHER INFORMATION: Synthetic Construct

<400> SEQUENCE: 214
tcggcttctt ctccaatg                                                 18

<210> SEQ ID NO 215
<211> LENGTH: 18
<212> TYPE: DNA
<213> ORGANISM: Artificial Sequence
<220> FEATURE:
<223> OTHER INFORMATION: Synthetic Construct

<400> SEQUENCE: 215
cttctccaat gtgtcatc                                                 18

<210> SEQ ID NO 216
<211> LENGTH: 18
<212> TYPE: DNA
<213> ORGANISM: Artificial Sequence
<220> FEATURE:
<223> OTHER INFORMATION: Synthetic Construct

<400> SEQUENCE: 216
ctccaatgtg tcatctgc                                                 18

<210> SEQ ID NO 217
<211> LENGTH: 18
<212> TYPE: DNA
<213> ORGANISM: Artificial Sequence
<220> FEATURE:
<223> OTHER INFORMATION: Synthetic Construct

<400> SEQUENCE: 217
tgtgtcatct gctttcga                                                 18

<210> SEQ ID NO 218
<211> LENGTH: 18
<212> TYPE: DNA
<213> ORGANISM: Artificial Sequence
<220> FEATURE:
<223> OTHER INFORMATION: Synthetic Construct

<400> SEQUENCE: 218
aaaatgtcac ccttggac                                                 18

<210> SEQ ID NO 219
<211> LENGTH: 18
<212> TYPE: DNA
<213> ORGANISM: Artificial Sequence
<220> FEATURE:
<223> OTHER INFORMATION: Synthetic Construct

<400> SEQUENCE: 219
acccttggac aagctgtg                                                 18

<210> SEQ ID NO 220
<211> LENGTH: 18
<212> TYPE: DNA
<213> ORGANISM: Artificial Sequence
<220> FEATURE:
<223> OTHER INFORMATION: Synthetic Construct

<400> SEQUENCE: 220
gacaagctgt gagaccaa                                                 18
```

<210> SEQ ID NO 221
<211> LENGTH: 18
<212> TYPE: DNA
<213> ORGANISM: Artificial Sequence
<220> FEATURE:
<223> OTHER INFORMATION: Synthetic Construct

<400> SEQUENCE: 221
tgtgagacca aagacctg                                                 18

<210> SEQ ID NO 222
<211> LENGTH: 18
<212> TYPE: DNA
<213> ORGANISM: Artificial Sequence
<220> FEATURE:
<223> OTHER INFORMATION: Synthetic Construct

<400> SEQUENCE: 222
gacctggttg tgcaacag                                                 18

<210> SEQ ID NO 223
<211> LENGTH: 18
<212> TYPE: DNA
<213> ORGANISM: Artificial Sequence
<220> FEATURE:
<223> OTHER INFORMATION: Synthetic Construct

<400> SEQUENCE: 223
caacaggcag gcacaaac                                                 18

<210> SEQ ID NO 224
<211> LENGTH: 18
<212> TYPE: DNA
<213> ORGANISM: Artificial Sequence
<220> FEATURE:
<223> OTHER INFORMATION: Synthetic Construct

<400> SEQUENCE: 224
ggcaggcaca aacaagac                                                 18

<210> SEQ ID NO 225
<211> LENGTH: 18
<212> TYPE: DNA
<213> ORGANISM: Artificial Sequence
<220> FEATURE:
<223> OTHER INFORMATION: Synthetic Construct

<400> SEQUENCE: 225
gactgatgtt gtctgtgg                                                 18

<210> SEQ ID NO 226
<211> LENGTH: 18
<212> TYPE: DNA
<213> ORGANISM: Artificial Sequence
<220> FEATURE:
<223> OTHER INFORMATION: Synthetic Construct

<400> SEQUENCE: 226
gttgtctgtg gtccccag                                                 18

<210> SEQ ID NO 227
<211> LENGTH: 18
<212> TYPE: DNA
<213> ORGANISM: Artificial Sequence
<220> FEATURE:

<223> OTHER INFORMATION: Synthetic Construct

<400> SEQUENCE: 227
gtccccagga tcggctga                                                          18

<210> SEQ ID NO 228
<211> LENGTH: 18
<212> TYPE: DNA
<213> ORGANISM: Artificial Sequence
<220> FEATURE:
<223> OTHER INFORMATION: Synthetic Construct

<400> SEQUENCE: 228
ctgagagccc tggtggtg                                                          18

<210> SEQ ID NO 229
<211> LENGTH: 18
<212> TYPE: DNA
<213> ORGANISM: Artificial Sequence
<220> FEATURE:
<223> OTHER INFORMATION: Synthetic Construct

<400> SEQUENCE: 229
agccctggtg gtgatccc                                                          18

<210> SEQ ID NO 230
<211> LENGTH: 18
<212> TYPE: DNA
<213> ORGANISM: Artificial Sequence
<220> FEATURE:
<223> OTHER INFORMATION: Synthetic Construct

<400> SEQUENCE: 230
atcctgtttg ccatcctc                                                          18

<210> SEQ ID NO 231
<211> LENGTH: 18
<212> TYPE: DNA
<213> ORGANISM: Artificial Sequence
<220> FEATURE:
<223> OTHER INFORMATION: Synthetic Construct

<400> SEQUENCE: 231
catcctcttg gtgctggt                                                          18

<210> SEQ ID NO 232
<211> LENGTH: 18
<212> TYPE: DNA
<213> ORGANISM: Artificial Sequence
<220> FEATURE:
<223> OTHER INFORMATION: Synthetic Construct

<400> SEQUENCE: 232
tgctggtctt tatcaaaa                                                          18

<210> SEQ ID NO 233
<211> LENGTH: 18
<212> TYPE: DNA
<213> ORGANISM: Artificial Sequence
<220> FEATURE:
<223> OTHER INFORMATION: Synthetic Construct

<400> SEQUENCE: 233
ccaagaagcc aaccaata                                                          18

```
<210> SEQ ID NO 234
<211> LENGTH: 18
<212> TYPE: DNA
<213> ORGANISM: Artificial Sequence
<220> FEATURE:
<223> OTHER INFORMATION: Synthetic Construct

<400> SEQUENCE: 234
caccccaagc aggaaccc                                                 18

<210> SEQ ID NO 235
<211> LENGTH: 18
<212> TYPE: DNA
<213> ORGANISM: Artificial Sequence
<220> FEATURE:
<223> OTHER INFORMATION: Synthetic Construct

<400> SEQUENCE: 235
gagatcaatt ttcccgac                                                 18

<210> SEQ ID NO 236
<211> LENGTH: 18
<212> TYPE: DNA
<213> ORGANISM: Artificial Sequence
<220> FEATURE:
<223> OTHER INFORMATION: Synthetic Construct

<400> SEQUENCE: 236
tcaattttcc cgacgatc                                                 18

<210> SEQ ID NO 237
<211> LENGTH: 18
<212> TYPE: DNA
<213> ORGANISM: Artificial Sequence
<220> FEATURE:
<223> OTHER INFORMATION: Synthetic Construct

<400> SEQUENCE: 237
gacgatcttc ctggctcc                                                 18

<210> SEQ ID NO 238
<211> LENGTH: 18
<212> TYPE: DNA
<213> ORGANISM: Artificial Sequence
<220> FEATURE:
<223> OTHER INFORMATION: Synthetic Construct

<400> SEQUENCE: 238
acgatcttcc tggctcca                                                 18

<210> SEQ ID NO 239
<211> LENGTH: 18
<212> TYPE: DNA
<213> ORGANISM: Artificial Sequence
<220> FEATURE:
<223> OTHER INFORMATION: Synthetic Construct

<400> SEQUENCE: 239
tccaacactg ctgctcca                                                 18

<210> SEQ ID NO 240
<211> LENGTH: 18
<212> TYPE: DNA
<213> ORGANISM: Artificial Sequence
<220> FEATURE:
<223> OTHER INFORMATION: Synthetic Construct
```

-continued

```
<400> SEQUENCE: 240
cagtgcagga gactttac                                                18

<210> SEQ ID NO 241
<211> LENGTH: 18
<212> TYPE: DNA
<213> ORGANISM: Artificial Sequence
<220> FEATURE:
<223> OTHER INFORMATION: Synthetic Construct

<400> SEQUENCE: 241
gactttacat ggatgcca                                                18

<210> SEQ ID NO 242
<211> LENGTH: 18
<212> TYPE: DNA
<213> ORGANISM: Artificial Sequence
<220> FEATURE:
<223> OTHER INFORMATION: Synthetic Construct

<400> SEQUENCE: 242
ttacatggat gccaaccg                                                18

<210> SEQ ID NO 243
<211> LENGTH: 18
<212> TYPE: DNA
<213> ORGANISM: Artificial Sequence
<220> FEATURE:
<223> OTHER INFORMATION: Synthetic Construct

<400> SEQUENCE: 243
caggaggatg gcaaagag                                                18

<210> SEQ ID NO 244
<211> LENGTH: 18
<212> TYPE: DNA
<213> ORGANISM: Artificial Sequence
<220> FEATURE:
<223> OTHER INFORMATION: Synthetic Construct

<400> SEQUENCE: 244
tcagtgcagg agagacag                                                18

<210> SEQ ID NO 245
<211> LENGTH: 18
<212> TYPE: DNA
<213> ORGANISM: Artificial Sequence
<220> FEATURE:
<223> OTHER INFORMATION: Synthetic Construct

<400> SEQUENCE: 245
agacagtgag gctgcacc                                                18

<210> SEQ ID NO 246
<211> LENGTH: 18
<212> TYPE: DNA
<213> ORGANISM: Artificial Sequence
<220> FEATURE:
<223> OTHER INFORMATION: Synthetic Construct

<400> SEQUENCE: 246
gtgggcaaac aggcagtt                                                18

<210> SEQ ID NO 247
<211> LENGTH: 18
```

```
<212> TYPE: DNA
<213> ORGANISM: Artificial Sequence
<220> FEATURE:
<223> OTHER INFORMATION: Synthetic Construct

<400> SEQUENCE: 247
caggggtgca ggcagaag                                                   18

<210> SEQ ID NO 248
<211> LENGTH: 18
<212> TYPE: DNA
<213> ORGANISM: Artificial Sequence
<220> FEATURE:
<223> OTHER INFORMATION: Synthetic Construct

<400> SEQUENCE: 248
gagctatgcc cagtcagt                                                   18
```

ANTISENSE MODULATION OF CD40 EXPRESSION

This application is a continuation of U.S. application Ser. No. 10/698,689 filed Oct. 31, 2003, now abandoned which is a continuation-in-part of U.S. application Ser. No. 10/261,382 filed Sep. 30, 2002 now abandoned and International Patent Application No. PCT/US03/31166 filed Sep. 30, 2003. U.S. application Ser. No. 10/698,689 is also a continuation-in-part of U.S. application Ser. No. 09/067,638, filed on Apr. 28, 1998, now U.S. Pat. No. 7,321,828 which claims priority to U.S. application Ser. No. 60/081,483, filed on Apr. 13, 1998. All of the foregoing are incorporated by reference herein in their entirety.

FIELD OF THE INVENTION

The present invention provides compositions and methods of modulating the expression of CD40. In particular, this invention relates to antisense compounds, particularly oligonucleotides, that are specifically hybridizable with nucleic acids encoding human CD40. Such oligonucleotides have been shown to modulate the expression of CD40.

BACKGROUND OF THE INVENTION

The immune system serves a vital role in protecting the body against infectious agents. It is well established, however, that a number of disease states and/or disorders are a result of either abnormal or undesirable activation of immune responses. Common examples include graft versus host disease (GVHD), graft rejection, inflammation, and autoimmune linked diseases such as multiple sclerosis (MS), systemic lupus erythematosus (SLE), and certain forms of arthritis.

In general, an immune response is activated as a result of either tissue injury or infection. Both cases involve the recruitment and activation of a number of immune system effector cells (i.e. B- and T-lymphocytes, macrophages, eosinophils, neutrophils) in a process coordinated through a series of complex cell-cell interactions. A typical scenario by which an immune response is mounted against a foreign protein is as follows: Foreign proteins captured by antigen presenting cells (APC's) such as macrophages or dendritic cells are processed and displayed on the cell surface of the APC. Circulating T-helper cells which express an immunoglobulin that recognizes (i.e. binds) the displayed antigen undergo activation by the APC. These activated T-helpers in turn activate appropriate B-cell clones to proliferate and differentiate into plasma cells that produce and secrete humoral antibodies targeted against the foreign antigen. The secreted humoral antibodies are free to circulate and bind to any cells expressing the foreign protein on their cell surface, in effect marking the cell for destruction by other immune effector cells. In each of the stages described above, direct cell-cell contact between the involved cell types is required in order for activation to occur [Gruss et al., Leuk. Lymphoma, 24, 393 (1997)]. In recent years, a number of cell surface receptors that mediate these cell-cell contact dependent activation events have been identified. Among these cell surface receptors is CD40 and its physiological ligand, CD40 Ligand (CD40L).

CD40 was first characterized as a receptor expressed on B-lymphocytes. It was later found that engagement of B-cell CD40 with CD40L expressed on activated T-cells is essential for T-cell dependent B-cell activation (i.e. proliferation, immunoglobulin secretion, and class switching. It was subsequently revealed that functional CD40 is expressed on a variety of cell types other than B-cells, including macrophages, dendritic cells, thymic epithelial cells, Langerhans cells, and endothelial cells. These studies have led to the current belief that CD40 plays a broad role in immune regulation by mediating interactions of T-cells with B-cells as well as other cell types. In support of this notion, it has been shown that stimulation of CD40 in macrophages and dendritic results is required for T-cell activation during antigen presentation [Gruss et al., Leuk. Lymphoma, 24, 393 (1997)]. Recent evidence points to a role for CD40 in tissue inflammation as well. Production of the inflammatory mediators IL-12 and nitric oxide by macrophages have been shown to be CD40 dependent [Buhlmann and Noelle, J. Clin. Immunol., 16, 83 (1996)]. In endothelial cells, stimulation of CD40 by CD40L has been found to induce surface expression of E-selectin, ICAM-1, and VCAM-1, promoting adhesion of leukocytes to sites of inflammation [Buhlmann and Noelle, J. Clin. Immunol., 16, 83 (1996); Gruss et al., Leuk. Lymphoma, 24, 393 (1997)]. Finally, a number of reports have documented overexpression of CD40 in epithelial and hematopoietic tumors as well as tumor infiltrating endothelial cells, indicating that CD40 may play a role in tumor growth and/or angiogenesis as well [Gruss et al., Leuk. Lymphoma, 24, 393 (1997); Kluth et al., Cancer Res., 57, 891 (1997)].

Due to the pivotal role that CD40 plays in humoral immunity, the potential exists that therapeutic strategies aimed at downregulating CD40 or interfering with CD40 signaling may provide a novel class of agents useful in treating a number of immune associated disorders, including but not limited to graft-versus-host disease (GVHD), graft rejection, and autoimmune diseases such as multiple sclerosis (MS), systemic lupus erythematosus (SLE), and certain forms of arthritis. Inhibitors of CD40 may also prove useful as anti-inflammatory compounds, and could therefore be useful as treatment for a variety of inflammatory and allergic conditions such as asthma, rheumatoid arthritis, allograft rejections, inflammatory bowel disease, autoimmune encephalomyelitis, thyroiditis, various dermatological conditions, and psoriasis. Recently, both CD40 and CD154 have been shown to be expressed on vascular endothelial cells, vascular smooth muscle cells and macrophages present in atherosclerotic plaques, suggesting that inflammation and immunity contribute to the atherogenic process. That this process involves CD40 signaling is suggested by several studies in mouse models in which disruption of CD154 (by knockout or by monoclonal antibody) reduced the progression or size of atherosclerotic lesions. Mach et al., 1998, Nature, 394, 200-3, Lutgens et al., 1999, Nat. Med. 5, 1313-6.

Finally, as more is learned of the association between CD40 overexpression and tumor growth, inhibitors of CD40 may prove useful as anti-tumor agents and inhibitors of other hyperproliferative conditions as well.

Currently, there are no known therapeutic agents which effectively inhibit the synthesis of CD40. To date, strategies aimed at inhibiting CD40 function have involved the use of a variety of agents that disrupt CD40/CD40L binding. These include monoclonal antibodies directed against either CD40 or CD40L, soluble forms of CD40, and synthetic peptides derived from a second CD40 binding protein, A20. The use of neutralizing antibodies against CD40 and/or CD40L in animal models has provided evidence that inhibition of CD40 signaling would have therapeutic benefit for GVHD, allograft rejection, rheumatoid arthritis, SLE, MS, and B-cell lymphoma [Buhlmann and Noelle, J. Clin. Immunol., 16, 83 (1996)]. Clinical investigations were initiated using CD154 monoclonal antibody in patients with lupus nephritis. However, studies were terminated due to the development of thrombotic events. Boumpas et al., 2003, Arthritis Rheum. March; 48, 719-27.

Due to the problems associated with the use of large proteins as therapeutic agents, there is a long-felt need for additional agents capable of effectively inhibiting CD40 function. Antisense oligonucleotides avoid many of the pitfalls of current agents used to block CD40/CD40L interactions and may therefore prove to be uniquely useful in a number of therapeutic, diagnostic and research applications. U.S. Pat. No. 6,197,584 (Bennett and Cowsert) discloses antisense compounds targeted to CD40.

Peptide nucleic acids, alternately referenced as PNAs, are known to be useful as oligonucleotide mimetics. In PNAs, both the sugar and the internucleoside linkage, i.e., the backbone, of the nucleotide units of oligonucleotides are replaced with novel groups. The sugar-backbone of an oligonucleotide is replaced with an amide containing backbone, in particular an aminoethylglycine backbone. The nucleobases are retained and are bound directly or indirectly to aza nitrogen atoms of the amide portion of the backbone. The base units, i.e., nucleobases, are maintained for hybridization with an appropriate nucleic acid target compound.

PNAs have been shown to have excellent hybridization properties as well as other properties useful for diagnostics, therapeutics and as research reagents. They are particularly useful as antisense reagents. Other uses include monitoring telomere length, screening for genetic mutations and for affinity capture of nucleic acids. As antisense reagents they can be used for transcriptional and translational blocking of genes and to effect alternate splicing. Further they can be used to bind to double stranded nucleic acids. Each of these uses are known and have been published in either the scientific or patent literature.

The synthesis of and use of PNAs has been extensively described. Representative United States patents that teach the preparation of and use of PNA compounds include, but are not limited to, U.S. Pat. Nos. 5,539,082; 5,5539,083; 5,641,625; 5,714,331; 5,719,262; 5,766,855; 5,773,571; 5,786,461; 5,831,014; 5,864,010; 5,986,053; 6,201,103; 6,204,326; 6,210,892; 6,228,982; 6,350,853; 6,414,112; 6,441,130; and 6,451,968, each of which is herein incorporated by reference. Additionally PNA compounds are described in numerous published PCT patent applications including WO 92/20702. Further teaching of PNA compounds can be found in scientific publications. The first such publication was Nielsen et al., *Science,* 1991, 254, 1497-1500.

Depending on sequence, the solubility of PNAs can differ and, as such, some PNA sequences are not soluble as might be desirable for a particular use. It was suggested in Karras, et al., Biochemistry, 2001, 40, 7853-7859, that PNAs could mediate splicing activity in cells. They compared a PNA 15mer (a PNA having 15 monomeric units) to the same PNA having a single lysine amino acid jointed to its C terminus. They suggested that the attached, i.e., conjugated, lysine residue might improve the cellular uptake. However, they concluded that their present data "do not show a clear difference in activity between the PNA 15mer with and without a C-terminal lysine."

In published application US-2002-0049173-A1, published Apr. 25, 2002, it was suggested that antisense compounds might have one or more cationic tails, preferable positively charged amino acids such as lysine or arginine, conjugated thereto. It was further suggested that one or more lysine or arginine residues might be conjugated to the C-terminal end of a PNA compound. No discrimination was made between the effects resulting from the conjugation of one lysine or arginine versus more than one of these lysine or arginine residues.

U.S. Pat. No. 6,593,292 suggests using guanidine or amidine moieties for uptake of various compounds including macromolecules. PNA is a suggested macromolecule. In one instance this patent suggests that the guanidine or amidine moieties comprise non-peptide backbones but in a further instance it suggested that the guanidine moiety will exist as a polyarginine molecule. However, no data is shown wherein any of these moieties are actually conjugated to a macromolecule and uptake is achieved.

In a transgenic mouse model, a 4-lysine conjugated PNA targeted to β-globin was demonstrated to provide efficacy in a range of tissues (Sazani et al., 2002, Nature Biotech. 20, 1228-1233).

SUMMARY OF THE INVENTION

The present invention is directed to antisense compounds, particularly oligonucleotides, that are targeted to a nucleic acid encoding CD40, and that modulate the expression of CD40. Pharmaceutical and other compositions comprising the antisense compounds of the invention are also provided. Further provided are methods of modulating the expression of CD40 in cells or tissues comprising contacting said cells or tissues with one or more of the antisense compounds or compositions of the invention. Further provided are methods of treating an animal, particularly a human, suspected of having or being prone to a disease or condition associated with expression of CD40 by administering a therapeutically or prophylactically effective amount of one or more of the antisense compounds or compositions of the invention.

DETAILED DESCRIPTION OF THE INVENTION

A. Overview of the Invention

The present invention employs antisense compounds, preferably oligonucleotides and similar species for use in modulating the function or effect of nucleic acid molecules encoding CD40. This is accomplished by providing oligonucleotides which specifically hybridize with one or more nucleic acid molecules encoding CD40. As used herein, the terms "target nucleic acid" and "nucleic acid molecule encoding CD40" have been used for convenience to encompass DNA encoding CD40, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of CD40. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. The first evidence that dsRNA could lead to gene silencing in animals came in 1995 from work in the nematode, *Caenorhabditis elegans* (Guo and Kempheus, *Cell,* 1995, 81, 611-620). Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, it has been shown that it is, in fact, the single-stranded RNA oligomers of antisense polarity of the dsRNAs which are the potent inducers of RNAi (Tijsterman et al., *Science,* 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes CD40.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding CD40, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the target nucleobase sequence (e.g., such as those disclosed in Example 9) comprising nucleobases 1-80, 81-160, 161-240, 241-320, 321-400, 401-480, 481-560, 561-640, 641-720, 721-800, 801-880, 881-960, 961-1004, or any combination thereof.

D. Screening and Target Validation

In a further embodiment, the "preferred target segments" identified herein may be employed in a screen for additional compounds that modulate the expression of CD40. "Modulators" are those compounds that decrease or increase the expression of a nucleic acid molecule encoding CD40 and which comprise at least an 8-nucleobase portion which is complementary to a preferred target segment. The screening method comprises the steps of contacting a preferred target segment of a nucleic acid molecule encoding CD40 with one or more candidate modulators, and selecting for one or more candidate modulators which decrease or increase the expression of a nucleic acid molecule encoding CD40. Once it is shown that the candidate modulator or modulators are capable of modulating (e.g. either decreasing or increasing) the expression of a nucleic acid molecule encoding CD40, the modulator may then be employed in further investigative studies of the function of CD40, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between CD40 and a disease state, phenotype, or condition. These methods include detecting or modulating CD40 comprising contacting a sample, tissue, cell, or organism with the compounds of the present invention, measuring the nucleic acid or protein level of CD40 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding CD40. For example, oligonucleotides that are shown to hybridize with such efficiency and under such conditions as disclosed herein as to be effective CD40 inhibitors will also be effective primers or probes under conditions favoring gene amplification or detection, respectively. These primers and probes are useful in methods requiring the specific detection of nucleic acid molecules encoding CD40 and in the amplification of said nucleic acid molecules for detection or for use in further studies of CD40. Hybridization of the antisense oligonucleotides, particularly the primers and probes, of the invention with a nucleic acid encoding CD40 can be detected by means known in the art. Such means may include conjugation of an enzyme to the oligonucleotide, radiolabelling of the oligonucleotide or any other suitable detection means. Kits using such detection means for detecting the level of CD40 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of CD40 is treated by administering antisense compounds in accordance with this invention. For example, in one non-limiting embodiment, the methods comprise the step of administering to the animal in need of treatment, a therapeutically effective amount of a CD40 inhibitor. The CD40 inhibitors of the present invention effectively inhibit the activity of the CD40 protein or inhibit the expression of the CD40 protein. In one embodiment, the activity or expression of CD40 in an animal is inhibited by about 10%. Preferably, the activity or expression of CD40 in an animal is inhibited by about 30%. More preferably, the activity or expression of CD40 in an animal is inhibited by 50% or more. Thus, the oligomeric antisense compounds modulate expression of CD40 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of CD40 may be measured in serum, adipose tissue, liver or any other body fluid, tissue or organ of the animal. Preferably, the cells contained within said fluids, tissues or organs being analyzed contain a nucleic acid molecule encoding CD40 protein and/or the CD40 protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkyl-phosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy(2'-OC$H_2$C$H_2$C$H_2$N$H_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methyl-cytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), Ser. No. 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published as WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dc amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy(2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378, 825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

present invention and their complements can be designed to target CD40. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID No.___161) and having a two-nucleobase overhang of deoxythymidine(dT) would have the following structure:

```
cgagaggcggacgggaccgTT  Antisense Strand  (SEQ ID No. 162)
|||||||||||||||||||
         TTgctctccgcctgccctggc  Complement  (SEQ ID No. 163)
```

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester]Chimeric Oligonucleotides

[2'-O-(2-methoxyethyl phosphodiester]-[2'-deoxy phosphorothioate]-[2'-O-(methoxyethyl) phosphodiester]chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting CD40

In accordance with the present invention, a series of nucleic acid duplexes comprising the antisense compounds of the In another embodiment, a duplex comprising an antisense strand having the same sequence CGAGAGGCGGACGG-GACCG may be prepared with blunt ends (no single stranded overhang) as shown:

```
cgagaggcggacgggaccg  Antisense Strand  (SEQ ID No. 161)
|||||||||||||||||||
gctctccgcctgccctggc  Complement  (SEQ ID No. 164)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate CD40 expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH₄OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH₄OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Antisense Sequences Targeted to Human CD40

In accordance with the present invention, a series of antisense sequences were designed to target different regions of the human CD40 mRNA, using published sequences [Stamenkovic et al., *EMBO J.*, 8, 1403 (1989); GenBank accession number X60592, (SEQ ID No. 85)]. The sequences are shown in Table 1.

TABLE 1

Antisense se|uences targeted to human CD40 mRNA

| ISIS# | TARGET REGION | TARGET SITE[1] | SEQUENCE | SEQ ID NO. |
|---|---|---|---|---|
| 18623 | 5' UTR | 18 | CCAGGCGGCAGGACCACT | 1 |
| 18624 | 5' UTR | 20 | GACCAGGCGGCAGGACCA | 2 |
| 18625 | 5' UTR | 26 | AGGTGAGACCAGGCGGCA | 3 |
| 18626 | AUG | 48 | CAGAGGCAGACGAACCAT | 4 |
| 18627 | Coding | 49 | GCAGAGGCAGACGAACCA | 5 |
| 18628 | Coding | 73 | GCAAGCAGCCCCAGAGGA | 6 |
| 18629 | Coding | 78 | GGTCAGCAAGCAGCCCCA | 7 |
| 18630 | Coding | 84 | GACAGCGGTCAGCAAGCA | 8 |
| 18631 | Coding | 88 | GATGGACAGCGGTCAGCA | 9 |
| 18632 | Coding | 92 | TCTGGATGGACAGCGGTC | 10 |
| 18633 | Coding | 98 | GGTGGTTCTGGATGGACA | 11 |
| 18634 | Coding | 101 | GTGGGTGGTTCTGGATGG | 12 |
| 18635 | Coding | 104 | GCAGTGGGTGGTTCTGGA | 13 |
| 18636 | Coding | 152 | CACAAAGAACAGCACTGA | 14 |
| 18637 | Coding | 156 | CTGGCACAAAGAACAGCA | 15 |
| 18638 | Coding | 162 | TCCTGGCTGGCACAAAGA | 16 |
| 18639 | Coding | 165 | CTGTCCTGGCTGGCACAA | 17 |
| 18640 | Coding | 176 | CTCACCAGTTTCTGTCCT | 18 |
| 18641 | Coding | 179 | TCACTCACCAGTTTCTGT | 19 |
| 18642 | Coding | 185 | GTGCAGTCACTCACCAGT | 20 |
| 18643 | Coding | 190 | ACTCTGTGCAGTCACTCA | 21 |
| 18644 | Coding | 196 | CAGTGAACTCTGTGCAGT | 22 |
| 18645 | Coding | 205 | ATTCCGTTTCAGTGAACT | 23 |
| 18646 | Coding | 211 | GAAGGCATTCCGTTTCAG | 24 |
| 18647 | Coding | 222 | TTCACCGCAAGGAAGGCA | 25 |
| 18648 | Coding | 250 | CTCTGTTCCAGGTGTCTA | 26 |
| 18649 | Coding | 267 | CTGGTGGCAGTGTGTCTC | 27 |
| 18650 | Coding | 286 | TGGGGTCGCAGTATTTGT | 28 |

TABLE 1-continued

Antisense sequences targeted to human CD40 mRNA

| ISIS# | TARGET REGION | TARGET SITE[1] | SEQUENCE | SEQ ID NO. |
|---|---|---|---|---|
| 18651 | Coding | 289 | GGTTGGGGTCGCAGTATT | 29 |
| 18652 | Coding | 292 | CTAGGTTGGGGTCGCAGT | 30 |
| 18653 | Coding | 318 | GGTGCCCTTCTGCTGGAC | 31 |
| 18654 | Coding | 322 | CTGAGGTGCCCTTCTGCT | 32 |
| 18655 | Coding | 332 | GTGTCTGTTTCTGAGGTG | 33 |
| 18656 | Coding | 334 | TGGTGTCTGTTTCTGAGG | 34 |
| 18657 | Coding | 345 | ACAGGTGCAGATGGTGTC | 35 |
| 18658 | Coding | 348 | TTCACAGGTGCAGATGGT | 36 |
| 18659 | Coding | 360 | GTGCCAGCCTTCTTCACA | 37 |
| 18660 | Coding | 364 | TACAGTGCCAGCCTTCTT | 38 |
| 18661 | Coding | 391 | GGACACAGCTCTCACAGG | 39 |
| 18662 | Coding | 395 | TGCAGGACACAGCTCTCA | 40 |
| 18663 | Coding | 401 | GAGCGGTGCAGGACACAG | 41 |
| 18664 | Coding | 416 | AAGCCGGGCGAGCATGAG | 42 |
| 18665 | Coding | 432 | AATCTGCTTGACCCCAAA | 43 |
| 18666 | Coding | 446 | GAAACCCTGTAGCAATC | 44 |
| 18667 | Coding | 452 | GTATCAGAAACCCTGTA | 45 |
| 18668 | Coding | 463 | GCTCGCAGATGGTATCAG | 46 |
| 18669 | Coding | 468 | GCAGGGCTCGCAGATGGT | 47 |
| 18670 | Coding | 471 | TGGGCAGGGCTCGCAGAT | 48 |
| 18671 | Coding | 474 | GACTGGGCAGGGCTCGCA | 49 |
| 18672 | Coding | 490 | CATTGGAGAAGAAGCCGA | 50 |
| 18673 | Coding | 497 | GATGACACATTGGAGAAG | 51 |
| 18674 | Coding | 500 | GCAGATGACACATTGGAG | 52 |
| 18675 | Coding | 506 | TCGAAAGCAGATGACACA | 53 |
| 18676 | Coding | 524 | GTCCAAGGGTGACATTTT | 54 |
| 18677 | Coding | 532 | CACAGCTTGTCCAAGGGT | 55 |
| 18678 | Coding | 539 | TTGGTCTCACAGCTTGTC | 56 |
| 18679 | Coding | 546 | CAGGTCTTTGGTCTCACA | 57 |
| 18680 | Coding | 558 | CTGTTGCACAACCAGGTC | 58 |
| 18681 | Coding | 570 | GTTTGTGCCTGCCTGTTG | 59 |
| 18682 | Coding | 575 | GTCTTGTTTGTGCCTGCC | 60 |
| 18683 | Coding | 590 | CCACAGACAACATCAGTC | 61 |
| 18684 | Coding | 597 | CTGGGGACCACAGACAAC | 62 |
| 18685 | Coding | 607 | TCAGCCGATCCTGGGGAC | 63 |
| 18686 | Coding | 621 | CACCACCAGGGCTCTCAG | 64 |
| 18687 | Coding | 626 | GGGATCACCACCAGGGCT | 65 |
| 18688 | Coding | 657 | GAGGATGGCAAACAGGAT | 66 |
| 18689 | Coding | 668 | ACCAGCACCAAGAGGATG | 67 |
| 18690 | Coding | 679 | TTTTGATAAAGACCAGCA | 68 |
| 18691 | Coding | 703 | TATTGGTTGGCTTCTTGG | 69 |
| 18692 | Coding | 729 | GGGTTCCTGCTTGGGGTG | 70 |
| 18693 | Coding | 750 | GTCGGGAAAATTGATCTC | 71 |
| 18694 | Coding | 754 | GATCGTCGGGAAAATTGA | 72 |
| 18695 | Coding | 765 | GGAGCCAGGAAGATCGTC | 73 |
| 18696 | Coding | 766 | TGGAGCCAGGAAGATCGT | 74 |
| 18697 | Coding | 780 | TGGAGCAGCAGTGTTGGA | 75 |
| 18698 | Coding | 796 | GTAAAGTCTCCTGCACTG | 76 |
| 18699 | Coding | 806 | TGGCATCCATGTAAAGTC | 77 |
| 18700 | Coding | 810 | CGGTTGGCATCCATGTAA | 78 |
| 18701 | Coding | 834 | CTCTTTGCCATCCTCCTG | 79 |
| 18702 | Coding | 861 | CTGTCTCTCCTGCACTGA | 80 |
| 18703 | Stop | 873 | GGTGCAGCCTCACTGTCT | 81 |
| 18704 | 3' UTR | 910 | AACTGCCTGTTTGCCCAC | 82 |
| 18705 | 3' UTR | 954 | CTTCTGCCTGCACCCCTG | 83 |
| 18706 | 3' UTR | 976 | ACTGACTGGGCATAGCTC | 84 |

[1]Target sites are indicated by the 5' most nucleotide to which the oligonucleotide hybridizes on the CD40 mRNA sequence. Nucleotide numbers are as given in the sequence source reference (Genbank accession no. X60592, incorporated herein as SEQ ID NO: 85). Target regions on the CD40 mRNA are also indicated.

Example 10

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following four cell types are provided for illustrative purposes, but other cell types can be routinely used.

T-24 Cells:

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in real-time quantitative polymerase chain reaction (PCR).

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 μg/mL (Gibco/Life Technologies, Gaithersburg, Md.). Cells were routinely passaged by trysinization and dilution when they reached 90% confluence.

NHDF Cells:

Human neonatal dermal fibroblast (NHDF) cells were obtained from the Clonetics Corporation (Walkersville, Md.). NHDFs were routinely maintained in Fibroblast Growth Medium (Clonetics Corporation, Walkersville, Md.) as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 μl Opti-MEM™-1 reduced-serum medium (Gibco BRL) and then treated with 130 μl of Opti-MEM™-1 containing 3.75 μg/mL LIPOFECTIN™ (Gibco BRL) and the desired oligonucleotide at a final concentration of 150 nM. After 4 hours of treatment, the medium was replaced with fresh medium. Cells were harvested 16 hours after oligonucleotide treatment.

Example 11

Analysis of Oligonucleotide Inhibition of CD40 Expression

Antisense modulation of CD40 expression can be assayed in a variety of ways known in the art. For example, CD40 mRNA levels can be quantitated by, e.g., Northern blot analysis, competitive PCR, or real-time PCR. Real-time quantitative PCR is presently preferred. RNA analysis can be performed on total cellular RNA or poly(A)+ mRNA. For real-time quantitative PCR, poly(A)+ mRNA is preferred. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., (1993). Northern blot analysis is routine in the art and is taught in, for example, Ausubel, F. M. et al., Current Protocols in Molecular Biology, Volume 1, pp. 4.2.1-4.2.9, John Wiley & Sons, Inc., (1996). Real-time quantitative polymerase chain reaction (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

CD40 protein levels can be quantitated in a variety of ways well known in the art, such as immunoprecipitation, Western blot analysis (immunoblotting), ELISA or fluorescence-activated cell sorting (FACS). Antibodies directed to CD40 can be identified and obtained from a variety of sources, such as those identified in the MSRS catalog of antibodies, (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., (1997). Preparation of monoclonal antibodies is taught in, for example, Ausubel, F. M. et al., Current Protocols in Molecular Biology, Volume 2, pp. 11.4.1-11.11.5, John Wiley & Sons, Inc., (1997)

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., (1998). Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., (1997). Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., (1991).

Example 12

Poly(A)+ mRNA Isolation

Poly(A)+ mRNA was isolated according to Miura et al., Clin. Chem., 42, 1758 (1996). Other methods for poly(A)+ mRNA isolation are taught in, for example, Ausubel, F. M. et al., Current Protocols in Molecular Biology, Volume 1, pp. 4.5.1-4.5.3, John Wiley & Sons, Inc., (1993). Briefly, for cells grown on 96-well plates, growth medium was removed from the cells and each well was washed with 200 μl cold PBS. 60 μl lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μl of lysate was transferred to Oligo d(T) coated 96-well plates (AGCT Inc., Irvine Calif.). Plates were incubated for 60 minutes at room temperature, washed 3 times with 200 μl of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μl of elution buffer (5 mM Tris-HCl pH 7.6), preheated to 70° C. was added to each well, the plate was incubated on a 90° hot plate for 5 minutes, and the eluate was then transferred to a fresh 96-well plate.

Cells grown on 100 mm or other standard plates may be treated similarly, using appropriate volumes of all solutions.

Example 13

Northern Blot Analysis of CD40 mRNA Levels

Eighteen hours after oligonucleotide treatment monolayers were washed twice with cold PBS and lysed in 0.5 mL RNAzol™ (TEL-TEST "B" Inc., Friendswood, Tex.). Total RNA was prepared following manufacturer's recommended protocols. Approximately ten μg of total RNA was fractionated by electrophoresis through 1.2% agarose gels containing 1.1% formaldehyde using a MOPS buffer system (Life Technologies, Inc., Rockville, Md.). RNA was transferred from the gel to Hybond™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a Stratalinker™ UV Crosslinker 2400 (Stratagene, Inc, La Jolla, Calif.).

Membranes were probed using QuickHyb™ hybridization solution (Stratagene, La Jolla, Calif.) using manufacturer's recommendations for stringent conditions with a CD40 specific probe prepared by PCR using the forward primer CAGAGTTCACTGAAACGGAATGC (SEQ ID No. 86) and the reverse primer GGTGGCAGTGTGTCTCTCTGTTC (SEQ ID No. 87). To normalize for variations in loading and transfer efficiency membranes were stripped and probed for glyceraldehyde-3-phosphate dehydrogenase (G3PDH) RNA (Clontech, Palo Alto, Calif.). Hybridized membranes were visualized and quantitated using a PhosphorImager™ and ImageQuant Software V3.3 (Molecular Dynamics, Sunnyvale, Calif.). Data was normalized to G3PDH levels in untreated controls.

Example 14

Real-Time Quantitative PCR Analysis of CD40 mRNA Levels

Quantitation of CD40 mRNA levels was conducted by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. Reverse transcriptase PCR reactions were carried out by adding 25 µl PCR cocktail (1× Taqman™ buffer A, 5.5 mM MgCl$_2$, 300 µM each of DATP, dCTP and dGTP, 600 µM of dUTP, 100 nM each of forward primer, reverse primer, and probe, 20 units RNAse inhibitor, 1.25 units AmpliTaq Gold™, and 12.5 units Moloney Murine Leukemia Virus (MuLV) Reverse Transcriptase to 96 well plates containing 25 µl poly(A) mRNA solution. The RT reaction was carried out by incubation for 30 minutes at 48° C. following a 10 minute incubation at 95° C. to activate the AmpliTaq Gold™, 40 cycles of a two-step PCR protocol were carried out: 95° C. for 15 seconds (denaturation) followed by 60° C. for one minute (annealing/extension).

For CD40, the PCR primers were: forward primer: CAGAGTTCACTGAAACGGAATGC (SEQ ID No. 86) reverse primer: GGTGGCAGTGTGTCTCTCTGTTC (SEQ ID No. 87) and the PCR probe was: FAM-TTCCTTGCGGT-GAAAGCGAATTCCT-TAMRA (SEQ ID No. 88) where FAM (PE-Applied Biosystems, Foster City, Calif.) is the fluorescent reporter dye) and TAMRA (PE-Applied Biosystems, Foster City, Calif.) is the quencher dye.

For GAPDH the PCR primers were:

forward primer: GAAGGTGAAGGTCGGAGTC (SEQ ID No. 89)

reverse primer: GAAGATGGTGATGGGATTTC (SEQ ID No. 90) and the

PCR probe was: 5' JOE-CAAGCTTCCCGTTCTCAGCC-TAMRA 3' (SEQ ID No. 91) where JOE (PE-Applied Biosystems, Foster City, Calif.) is the fluorescent reporter dye) and TAMRA (PE-Applied Biosystems, Foster City, Calif.) is the quencher dye.

Example 15

Western Blot Analysis of CD40 Protein Levels

Western blot analysis (immunoblot analysis) is carried out using standard methods. Cells are harvested 16-20 hr after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to CD40 is used, with a radiolabelled or fluorescently labeled secondary antibody directed against the primary antibody species. Bands are visualized using a PhosphorImager™ (Molecular Dynamics, Sunnyvale Calif.).

Example 16

Antisense Inhibition of CD40 Expression by Phosphorothioate Oligodeoxynucleotides In accordance with the present invention, a series of oligonucleotides were designed to target different regions of the human CD40 mRNA, using published sequences [Stamenkovic et al., *EMBO J.*, 8, 1403 (1989); GenBank accession number X60592, incorporated herein as SEQ ID NO: 85]. The oligonucleotides are shown in Table 2. Target sites are indicated by the 5' most nucleotide to which the oligonucleotide hybridizes on the CD40 mRNA sequence. Nucleotide numbers are as given in the sequence source reference (Genbank accession no. X60592, incorporated herein as SEQ ID NO: 85). All compounds in Table 2 are oligodeoxynucleotides with phosphorothioate backbones (internucleoside linkages) throughout. The compounds were analyzed for effect on CD40 mRNA levels by real-time PCR quantitation of RNA as described in Example 14. Data are averages from three experiments.

TABLE 2

Inhibition of CD40 mRNA levels by phosphorothioate oligodeoxynucleotides

| ISIS# | TARGET REGION | TARGET SITE | SEQUENCE | % INHIB. | SEQ ID NO. |
|---|---|---|---|---|---|
| 18623 | 5' UTR | 18 | CCAGGCGGCAGGACCACT | 30.71 | 1 |
| 18624 | 5' UTR | 20 | GACCAGGCGGCAGGACCA | 28.09 | 2 |
| 18625 | 5' UTR | 26 | AGGTGAGACCAGGCGGCA | 21.89 | 3 |
| 18626 | AUG | 48 | CAGAGGCAGACGAACCAT | 0.00 | 4 |
| 18627 | Coding | 49 | GCAGAGGCAGACGAACCA | 0.00 | 5 |
| 18628 | Coding | 73 | GCAAGCAGCCCCAGAGGA | 0.00 | 6 |
| 18629 | Coding | 78 | GGTCAGCAAGCAGCCCCA | 29.96 | 7 |
| 18630 | Coding | 84 | GACAGCGGTCAGCAAGCA | 0.00 | 8 |
| 18631 | Coding | 88 | GATGGACAGCGGTCAGCA | 0.00 | 9 |
| 18632 | Coding | 92 | TCTGGATGGACAGCGGTC | 0.00 | 10 |
| 18633 | Coding | 98 | GGTGGTTCTGGATGGACA | 0.00 | 11 |
| 18634 | Coding | 101 | GTGGGTGGTTCTGGATGG | 0.00 | 12 |
| 18635 | Coding | 104 | GCAGTGGGTGGTTCTGGA | 0.00 | 13 |
| 18636 | Coding | 152 | CACAAAGAACAGCACTGA | 0.00 | 14 |
| 18637 | Coding | 156 | CTGGCACAAAGAACAGCA | 0.00 | 15 |
| 18638 | Coding | 162 | TCCTGGCTGGCACAAAGA | 0.00 | 16 |
| 18639 | Coding | 165 | CTGTCCTGGCTGGCACAA | 4.99 | 17 |
| 18640 | Coding | 176 | CTCACCAGTTTCTGTCCT | 0.00 | 18 |
| 18641 | Coding | 179 | TCACTCACCAGTTTCTGT | 0.00 | 19 |
| 18642 | Coding | 185 | GTGCAGTCACTCACCAGT | 0.00 | 20 |
| 18643 | Coding | 190 | ACTCTGTGCAGTCACTCA | 0.00 | 21 |
| 18644 | Coding | 196 | CAGTGAACTCTGTGCAGT | 5.30 | 22 |
| 18645 | Coding | 205 | ATTCCGTTTCAGTGAACT | 0.00 | 23 |
| 18646 | Coding | 211 | GAAGGCATTCCGTTTCAG | 9.00 | 24 |
| 18647 | Coding | 222 | TTCACCGCAAGGAAGGCA | 0.00 | 25 |
| 18648 | Coding | 250 | CTCTGTTCCAGGTGTCTA | 0.00 | 26 |
| 18649 | Coding | 267 | CTGGTGGCAGTGTGTCTC | 0.00 | 27 |
| 18650 | Coding | 286 | TGGGGTCGCAGTATTTGT | 0.00 | 28 |
| 18651 | Coding | 289 | GGTTGGGGTCGCAGTATT | 0.00 | 29 |
| 18652 | Coding | 292 | CTAGGTTGGGGTCGCAGT | 0.00 | 30 |
| 18653 | Coding | 318 | GGTGCCCTTCTGCTGGAC | 19.67 | 31 |
| 18654 | Coding | 322 | CTGAGGTGCCCTTCTGCT | 15.63 | 32 |
| 18655 | Coding | 332 | GTGTCTGTTTCTGAGGTG | 0.00 | 33 |
| 18656 | Coding | 334 | TGGTGTCTGTTTCTGAGG | 0.00 | 34 |
| 18657 | Coding | 345 | ACAGGTGCAGATGGTGTC | 0.00 | 35 |
| 18658 | Coding | 348 | TTCACAGGTGCAGATGGT | 0.00 | 36 |
| 18659 | Coding | 360 | GTGCCAGCCTTCTTCACA | 5.67 | 37 |
| 18660 | Coding | 364 | TACAGTGCCAGCCTTCTT | 7.80 | 38 |
| 18661 | Coding | 391 | GGACACAGCTCTCACAGG | 0.00 | 39 |
| 18662 | Coding | 395 | TGCAGGACACAGCTCTCA | 0.00 | 40 |
| 18663 | Coding | 401 | GAGCGGTGCAGGACACAG | 0.00 | 41 |
| 18664 | Coding | 416 | AAGCCGGGCGAGCATGAG | 0.00 | 42 |
| 18665 | Coding | 432 | AATCTGCTTGACCCCAAA | 5.59 | 43 |
| 18666 | Coding | 446 | GAAACCCCTGTAGCAATC | 0.10 | 44 |
| 18667 | Coding | 452 | GTATCAGAAACCCCTGTA | 0.00 | 45 |
| 18668 | Coding | 463 | GCTCGCAGATGGTATCAG | 0.00 | 46 |
| 18669 | Coding | 468 | GCAGGGCTCGCAGATGGT | 34.05 | 47 |
| 18670 | Coding | 471 | TGGGCAGGGCTCGCAGAT | 0.00 | 48 |
| 18671 | Coding | 474 | GACTGGGCAGGGCTCGCA | 2.71 | 49 |
| 18672 | Coding | 490 | CATTGGAGAAGAAGCCGA | 0.00 | 50 |
| 18673 | Coding | 497 | GATGACACATTGGAGAAG | 0.00 | 51 |
| 18674 | Coding | 500 | GCAGATGACACATTGGAG | 0.00 | 52 |
| 18675 | Coding | 506 | TCGAAAGCAGATGACACA | 0.00 | 53 |
| 18676 | Coding | 524 | GTCCAAGGGTGACATTTT | 8.01 | 54 |
| 18677 | Coding | 532 | CACAGCTTGTCCAAGGGT | 0.00 | 55 |
| 18678 | Coding | 539 | TTGGTCTCACAGCTTGTC | 0.00 | 56 |
| 18679 | Coding | 546 | CAGGTCTTTGGTCTCACA | 6.98 | 57 |
| 18680 | Coding | 558 | CTGTTGCACAACCAGGTC | 18.76 | 58 |
| 18681 | Coding | 570 | GTTTGTGCCTGCCTGTTG | 2.43 | 59 |
| 18682 | Coding | 575 | GTCTTGTTTGTGCCTGCC | 0.00 | 60 |
| 18683 | Coding | 590 | CCACAGACAACATCAGTC | 0.00 | 61 |
| 18684 | Coding | 597 | CTGGGGACCACAGACAAC | 0.00 | 62 |
| 18685 | Coding | 607 | TCAGCCGATCCTGGGGAC | 0.00 | 63 |
| 18686 | Coding | 621 | CACCACCAGGGCTCTCAG | 23.31 | 64 |
| 18687 | Coding | 626 | GGGATCACCACCAGGGCT | 0.00 | 65 |
| 18688 | Coding | 657 | GAGGATGGCAAACAGGAT | 0.00 | 66 |
| 18689 | Coding | 668 | ACCAGCACCAAGAGGATG | 0.00 | 67 |
| 18690 | Coding | 679 | TTTTGATAAAGACCAGCA | 0.00 | 68 |
| 18691 | Coding | 703 | TATTGGTTGGCTTCTTGG | 0.00 | 69 |
| 18692 | Coding | 729 | GGGTTCCTGCTTGGGGTG | 0.00 | 70 |
| 18693 | Coding | 750 | GTCGGGAAAATTGATCTC | 0.00 | 71 |
| 18694 | Coding | 754 | GATCGTCGGGAAAATTGA | 0.00 | 72 |

TABLE 2-continued

Inhibition of CD40 mRNA levels by phosphorothioate oligodeoxynucleotides

| ISIS# | TARGET REGION | TARGET SITE | SEQUENCE | % INHIB. | SEQ ID NO. |
|---|---|---|---|---|---|
| 18695 | Coding | 765 | GGAGCCAGGAAGATCGTC | 0.00 | 73 |
| 18696 | Coding | 766 | TGGAGCCAGGAAGATCGT | 0.00 | 74 |
| 18697 | Coding | 780 | TGGAGCAGCAGTGTTGGA | 0.00 | 75 |
| 18698 | Coding | 796 | GTAAAGTCTCCTGCACTG | 0.00 | 76 |
| 18699 | Coding | 806 | TGGCATCCATGTAAAGTC | 0.00 | 77 |
| 18700 | Coding | 810 | CGGTTGGCATCCATGTAA | 0.00 | 78 |
| 18701 | Coding | 834 | CTCTTTGCCATCCTCCTG | 4.38 | 79 |
| 18702 | Coding | 861 | CTGTCTCTCCTGCACTGA | 0.00 | 80 |
| 18703 | Stop | 873 | GGTGCAGCCTCACTGTCT | 0.00 | 81 |
| 18704 | 3' UTR | 910 | AACTGCCTGTTTGCCCAC | 33.89 | 82 |
| 18705 | 3' UTR | 954 | CTTCTGCCTGCACCCCTG | 0.00 | 83 |
| 18706 | 3' UTR | 976 | ACTGACTGGGCATAGCTC | 0.00 | 84 |

As shown in Table 2, SEQ ID NOs 1, 2, 7, 47 and 82 demonstrated at least 25% inhibition of CD40 expression in this assay and are therefore preferred.

Example 17

Antisense Inhibition of CD40 Expression by Phosphorothioate 2'-MOE Gapmer Oligonucleotides In accordance with the present invention, a second series of oligonucleotides targeted to human CD40 were synthesized. The oligonucleotides are shown in Table 3. Target sites are indicated by nucleotide numbers, as given in the sequence source reference (Stamenkovic et al., *EMBO J.*, 8, 1403 (1989); Genbank accession no. X60592), to which the oligonucleotide binds.

All compounds in Table 3 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings." The wings are composed of 2'-methoxyethyl (2'-MOE) nucleotides. The internucleoside (backbone) linkages are phosphorothioate (P=S) throughout the oligonucleotide. Cytidine residues in the 2'-MOE wings are 5-methylcytidines.

Data were obtained by real-time quantitative PCR as described in Example 14 and are averaged from three experiments. "ND" indicates a value was not determined.

TABLE 3

Inhibition of CD40 mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 19211 | 5' UTR | 18 | CCAGGCGGCAGGACCACT | 75.71 | 1 |
| 19212 | 5' UTR | 20 | GACCAGGCGGCAGGACCA | 77.23 | 2 |
| 19213 | 5' UTR | 26 | AGGTGAGACCAGGCGGCA | 80.82 | 3 |
| 19214 | AUG | 48 | CAGAGGCAGACGAACCAT | 23.68 | 4 |
| 19215 | Coding | 49 | GCAGAGGCAGACGAACCA | 45.97 | 5 |
| 19216 | Coding | 73 | GCAAGCAGCCCCAGAGGA | 65.80 | 6 |
| 19217 | Coding | 78 | GGTCAGCAAGCAGCCCCA | 74.73 | 7 |
| 19218 | Coding | 84 | GACAGCGGTCAGCAAGCA | 67.21 | 8 |
| 19219 | Coding | 88 | GATGGACAGCGGTCAGCA | 65.14 | 9 |
| 19220 | Coding | 92 | TCTGGATGGACAGCGGTC | 78.71 | 10 |
| 19221 | Coding | 98 | GGTGGTTCTGGATGGACA | 81.33 | 11 |
| 19222 | Coding | 101 | GTGGGTGGTTCTGGATGG | 57.79 | 12 |
| 19223 | Coding | 104 | GCAGTGGGTGGTTCTGGA | 73.70 | 13 |
| 19224 | Coding | 152 | CACAAAGAACAGCACTGA | 40.25 | 14 |
| 19225 | Coding | 156 | CTGGCACAAAGAACAGCA | 60.11 | 15 |
| 19226 | Coding | 162 | TCCTGGCTGGCACAAAGA | 10.18 | 16 |
| 19227 | Coding | 165 | CTGTCCTGGCTGGCACAA | 24.37 | 17 |
| 19228 | Coding | 176 | CTCACCAGTTTCTGTCCT | 22.30 | 18 |

TABLE 3-continued

Inhibition of CD40 mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 19229 | Coding | 179 | TCACTCACCAGTTTCTGT | 40.64 | 19 |
| 19230 | Coding | 185 | GTGCAGTCACTCACCAGT | 82.04 | 20 |
| 19231 | Coding | 190 | ACTCTGTGCAGTCACTCA | 37.59 | 21 |
| 19232 | Coding | 196 | CAGTGAACTCTGTGCAGT | 40.26 | 22 |
| 19233 | Coding | 205 | ATTCCGTTTCAGTGAACT | 56.03 | 23 |
| 19234 | Coding | 211 | GAAGGCATTCCGTTTCAG | 32.21 | 24 |
| 19235 | Coding | 222 | TTCACCGCAAGGAAGGCA | 61.03 | 25 |
| 19236 | Coding | 250 | CTCTGTTCCAGGTGTCTA | 62.19 | 26 |
| 19237 | Coding | 267 | CTGGTGGCAGTGTGTCTC | 70.32 | 27 |
| 19238 | Coding | 286 | TGGGGTCGCAGTATTTGT | 0.00 | 28 |
| 19239 | Coding | 289 | GGTTGGGGTCGCAGTATT | 19.40 | 29 |
| 19240 | Coding | 292 | CTAGGTTGGGGTCGCAGT | 36.32 | 30 |
| 19241 | Coding | 318 | GGTGCCCTTCTGCTGGAC | 78.91 | 31 |
| 19242 | Coding | 322 | CTGAGGTGCCCTTCTGCT | 69.84 | 32 |
| 19243 | Coding | 332 | GTGTCTGTTTCTGAGGTG | 63.32 | 33 |
| 19244 | Coding | 334 | TGGTGTCTGTTTCTGAGG | 42.83 | 34 |
| 19245 | Coding | 345 | ACAGGTGCAGATGGTGTC | 73.31 | 35 |
| 19246 | Coding | 348 | TTCACAGGTGCAGATGGT | 47.72 | 36 |
| 19247 | Coding | 360 | GTGCCAGCCTTCTTCACA | 61.32 | 37 |
| 19248 | Coding | 364 | TACAGTGCCAGCCTTCTT | 46.82 | 38 |
| 19249 | Coding | 391 | GGACACAGCTCTCACAGG | 0.00 | 39 |
| 19250 | Coding | 395 | TGCAGGACACAGCTCTCA | 52.05 | 40 |
| 19251 | Coding | 401 | GAGCGGTGCAGGACACAG | 50.15 | 41 |
| 19252 | Coding | 416 | AAGCCGGGCGAGCATGAG | 32.36 | 42 |
| 19253 | Coding | 432 | AATCTGCTTGACCCCAAA | 0.00 | 43 |
| 19254 | Coding | 446 | GAAACCCTGTAGCAATC | 0.00 | 44 |
| 19255 | Coding | 452 | GTATCAGAAACCCCTGTA | 36.13 | 45 |
| 19256 | Coding | 463 | GCTCGCAGATGGTATCAG | 64.65 | 46 |
| 19257 | Coding | 468 | GCAGGGCTCGCAGATGGT | 74.95 | 47 |
| 19258 | Coding | 471 | TGGGCAGGGCTCGCAGAT | 0.00 | 48 |
| 19259 | Coding | 474 | GACTGGGCAGGGCTCGCA | 82.00 | 49 |
| 19260 | Coding | 490 | CATTGGAGAAGAAGCCGA | 41.31 | 50 |
| 19261 | Coding | 497 | GATGACACATTGGAGAAG | 13.81 | 51 |
| 19262 | Coding | 500 | GCAGATGACACATTGGAG | 78.48 | 52 |
| 19263 | Coding | 506 | TCGAAAGCAGATGACACA | 59.28 | 53 |
| 19264 | Coding | 524 | GTCCAAGGGTGACATTT | 70.99 | 54 |
| 19265 | Coding | 532 | CACAGCTTGTCCAAGGGT | 0.00 | 55 |

TABLE 3-continued

Inhibition of CD40 mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 19266 | Coding | 539 | TTGGTCTCACAGCTTGTC | 45.92 | 56 |
| 19267 | Coding | 546 | CAGGTCTTTGGTCTCACA | 63.95 | 57 |
| 19268 | Coding | 558 | CTGTTGCACAACCAGGTC | 82.32 | 58 |
| 19269 | Coding | 570 | GTTTGTGCCTGCCTGTTG | 70.10 | 59 |
| 19270 | Coding | 575 | GTCTTGTTTGTGCCTGCC | 68.95 | 60 |
| 19271 | Coding | 590 | CCACAGACAACATCAGTC | 11.22 | 61 |
| 19272 | Coding | 597 | CTGGGGACCACAGACAAC | 9.04 | 62 |
| 19273 | Coding | 607 | TCAGCCGATCCTGGGGAC | 0.00 | 63 |
| 19274 | Coding | 621 | CACCACCAGGGCTCTCAG | 23.08 | 64 |
| 19275 | Coding | 626 | GGGATCACCACCAGGGCT | 57.94 | 65 |
| 19276 | Coding | 657 | GAGGATGGCAAACAGGAT | 49.14 | 66 |
| 19277 | Coding | 668 | ACCAGCACCAAGAGGATG | ND | 67 |
| 19278 | Coding | 679 | TTTTGATAAAGACCAGCA | 30.58 | 68 |
| 19279 | Coding | 703 | TATTGGTTGGCTTCTTGG | 49.26 | 69 |
| 19280 | Coding | 729 | GGGTTCCTGCTTGGGGTG | 13.95 | 70 |
| 19281 | Coding | 750 | GTCGGGAAAATTGATCTC | 54.78 | 71 |
| 19282 | Coding | 754 | GATCGTCGGGAAAATTGA | 0.00 | 72 |
| 19283 | Coding | 765 | GGAGCCAGGAAGATCGTC | 69.47 | 73 |
| 19284 | Coding | 766 | TGGAGCCAGGAAGATCGT | 54.48 | 74 |
| 19285 | Coding | 780 | TGGAGCAGCAGTGTTGGA | 15.17 | 75 |
| 19286 | Coding | 796 | GTAAAGTCTCCTGCACTG | 30.62 | 76 |
| 19287 | Coding | 806 | TGGCATCCATGTAAAGTC | 65.03 | 77 |
| 19288 | Coding | 810 | CGGTTGGCATCCATGTAA | 34.49 | 78 |
| 19289 | Coding | 834 | CTCTTTGCCATCCTCCTG | 41.84 | 79 |
| 19290 | Coding | 861 | CTGTCTCTCCTGCACTGA | 25.68 | 80 |
| 19291 | Coding | 873 | GGTGCAGCCTCACTGTCT | 76.27 | 81 |
| 19292 | 3' UTR | 910 | AACTGCCTGTTTGCCCAC | 63.34 | 82 |
| 19293 | 3' UTR | 954 | CTTCTGCCTGCACCCCTG | 0.00 | 83 |
| 19294 | 3' UTR | 976 | ACTGACTGGGCATAGCTC | 11.55 | 84 |

As shown in Table 3, SEQ ID NO: 1, 2, 3, 6, 7, 8, 9, 10, 11, 12, 13, 15, 20, 23, 25, 26, 27, 31, 32, 33, 35, 37, 40, 41, 46, 47, 49, 52, 53, 54, 57, 58, 59, 60, 65, 71, 73, 74, 77, 81 and 82 demonstrated at least 50% inhibition of CD40 expression in this experiment and are therefore preferred.

Example 18

Correlation of Quantitative Real-time PCR Measurements of RNA Levels with Northern Analysis of RNA Levels The reduction of CD40 mRNA levels by the oligonucleotide compounds in Tables 2 and 3 was also demonstrated by Northern blot analysis of CD40 mRNA from oligonucleotide treated cells, as described in Example 13. The RNA measurements made by Northern analysis were compared to the RNA measurements obtained using quantitative real-time PCR, using averaged data from three experiments in each case.

When the phosphorothioate oligodeoxynucleotides shown in Table 2 were tested by Northern blot analysis, SEQ ID Nos 1, 2, 3, 7, 25, 31, 32, 37, 43, 47, 58, 64 and 82 were determined to reduce CD40 mRNA levels by at least 75% and are therefore preferred. Of these, SEQ ID Nos 1, 64 and 82 reduced CD40 mRNA levels by at least 80%.

The correlation coefficient for the results of quantitative real-time PCR vs. Northern blot analysis for the phosphorothioate oligodeoxynucleotides was found to be 0.67.

When the phosphorothioate 2'-MOE chimeric oligonucleotides shown in Table 3 were tested by Northern blot analysis, SEQ ID Nos 1, 2, 3, 5, 7, 10, 20, 25, 26, 27, 31, 32, 33, 35, 37, 40, 46, 47, 49, 52, 54, 58, 59, 60, 73, 81 and 82 were determined to reduce CD40 mRNA levels by at least 90% and are therefore preferred. Of these, SEQ ID Nos 1, 2, 20, 31 and 58 reduced CD40 mRNA levels by at least 95%.

The correlation coefficient for quantitative real-time PCR vs Northern blot results for the phosphorothioate 2'-MOE chimeric oligonucleotides was 0.78.

Example 19

Oligonucleotide-Sensitive Sites of the CD40 Target Nucleic Acid

As the data presented in the preceding examples shows, several sequences were present in preferred compounds of two distinct oligonucleotide chemistries. Specifically, compounds having SEQ ID NOS: 1, 2, 7, 47 and 82 are preferred in both instances. These compounds are believed to define accessible sites of the target nucleic acid to various antisense compositions and are therefore preferred. For example, SEQ ID NOS: 1 and 2 overlap each other and both map to the 5-untranslated region (5'-UTR) of CD40. Accordingly, this region of CD40 is particularly preferred for modulation via sequence-based technologies. Similarly, SEQ ID NOS: 7 and 47 map to the open reading frame of CD40, whereas SEQ ID NO: 82 maps to the 3'-untranslated region (3'-UTR). Thus, the ORF and 3'-UTR of CD40 may be targeted by sequence-based technologies as well.

It has been shown, furthermore, that certain target sequences on the CD40 mRNA are particularly suitable to antisense targeting. The reverse complements of the active CD40 compounds, e.g., the sequence on the CD40 nucleic acid target to which the active antisense compounds are complementary, are easily determined by those skilled in the art and may be assembled to yield nucleotide sequences corresponding to favorable sites on the target nucleic acid. For example, when the antisense sequences shown in Tables 1-3 were mapped onto the CD40 mRNA sequence [Stamenkovic et al., *EMBO J.*, 8, 1403 (1989); GenBank accession number X60592], in some instances it was found in some cases that all the oligonucleotides targeted to a particular sequence region of CD40 (usually called a "footprint") were active. Therefore, this footprint region is particularly preferred for antisense targeting, and oligonucleotide sequences hybridizable to this footprint are preferred compounds of the invention. A library of this information is compiled and may be used by those skilled in the art in a variety of sequence-based technologies to study the molecular and biological functions of CD40 and to investigate or confirm its role in various diseases and disorders.

An example of such a compilation is shown in Table 4, in which the antisense sequences shown in Tables 1-3 are mapped onto the CD40 mRNA sequence [Stamenkovic et al., *EMBO J.*, 8, 1403 (1989); GenBank accession number X60592]. The antisense sequences (SEQ ID NO: 1, 2, 3, 6, 7, 8, 9, 10, 11, 12, 13, 15, 20, 23, 25, 26, 27, 31, 32, 33, 35, 37, 40, 41, 46, 47, 49, 52, 53, 54, 57, 58, 59, 60, 65, 71, 73, 74, 77, 81 and 82) which were determined by real-time quantitative PCR assay to be active as inhibitors of CD40 are shown in bold. Examples of "footprint" sequences on the CD40 mRNA sequence to which a series of active oligonucleotides bind are also shown in bold. These "footprint" sequences and antisense compounds binding to them (including those not shown herein) are preferred for targeting.

TABLE 4

CD40 Antisense Sequence Alignment

| SEQ ID NO: | 1 | 15 | 16 | 30 | 31 | 45 | 46 | 60 | 61 | 75 | 76 | 90 |
|---|---|---|---|---|---|---|---|---|---|---|---|---|
| 173 | ---------------- | ---------------- | ---------------- | ---------------- | ---------------- | ---------------- | ---------------- | ---------------- | ---------------- | ---------------- | ------------- | TGC |
| 172 | ---------------- | ---------------- | ---------------- | ---------------- | ---------------- | ---------------- | ---------------- | ---------------- | ---------------- | ---------------- | --------- | TGCTTGC |
| 171 | ---------------- | ---------------- | ---------------- | ---------------- | ---------------- | ---------------- | ---------------- | ---------------- | ---------------- | ---------------- | --- | TGGGGCTGCTTGC |
| 170 | ---------------- | ---------------- | ---------------- | ---------------- | ---------------- | ---------------- | ---------------- | ---------------- | ---------------- | ------------ | TCC | TCTGGGGCTGCTTGC |
| 169 | ---------------- | ---------------- | ---------------- | ---------------- | ---------------- | ---------------- | --- | TGGTTCGTCTGC | CTCTGC | --------- | ---------------- | ---------------- |
| 168 | ---------------- | ---------------- | ---------------- | ---------------- | ---------------- | ---------------- | -- | ATGGTTCGTCTGC | CTCTG | ---------- | ---------------- | ---------------- |
| 167 | ---------------- | ---------------- | ---------- | TGCCG | CCTGGTCTCACCT | -- | ---------------- | ---------------- | ---------------- | ---------------- | ---------------- | ---------------- |
| 166 | ---------------- | ---------------- | ---- | TGGTCCTGCCG | CCTGGTC | ------- | ---------------- | ---------------- | ---------------- | ---------------- | ---------------- | ---------------- |
| 165 | ---------------- | ---------------- | -- | AGTGGTCCTGCCG | CCTGG | --------- | ---------------- | ---------------- | ---------------- | ---------------- | ---------------- | ---------------- |
| X60592-CD40 | GCCTCGCTCGGGCGC | CCAGTGGTCCTGCCG | CCTGGTCTCACCTCG | CCATGGTTCGTGTGC | CTCTGCAGTGCGTCC | TCTGGGGCTGCTTGC |  |  |  |  |  |  |

TABLE 4-continued

CD40 Antisense Sequence Alignment

```
SEQ
ID NO:
           91              105 106            120 121             135 136            150 151            165 166            180
183        ----------------    ----------------    ----------------    ----------------    ----------------    -------------AC
182        ----------------    ----------------    ----------------    ----------------    ----------------    ----------AGGAC
181        ----------------    ----------------    ----------------    ----------------    ----------------    ----------T TGTGCCAGCCAGGAC
180        ----------------    ----------------    ----------------    ----------------    ----------------    -----------TCTT TGTGCCAG-------
179        ----------------    ----------------    ----------------    ----------------    ----------------    -----TGCTGTTCTT TGTG-----------
178        ----------------    ----------------    ----------------    ----------------    ----------------    -TCAGTGCTGTTCTT ---------------
177        -------------TC     CAGAACCACCCACTG     C---------------    ----------------    ----------------    ---------------
176        ----------CCATC     CAGAACCACCCAC--     ----------------    ----------------    ----------------    ---------------
175        -------TGTCCATC     CAGAACCACC-----     ----------------    ----------------    ----------------    ---------------
174        -GACCGCTGTCCATC     CAGA-----------     ----------------    ----------------    ----------------    ---------------
173        TGACCGCTGTCCATC     ---------------     ----------------    ----------------    ----------------    ---------------
172        TGACCGCTGTC----     ---------------     ----------------    ----------------    ----------------    ---------------
171        TGACC----------     ---------------     ----------------    ----------------    ----------------    ---------------
X60592-    TGACCGCTGTCCATC     CAGAACCACCCACTG     CATGCAGAGAAAAAC     AGTACCTAATAAACA     GTCAGTGCTGTTCTT     TGTGCCAGCCAGGAC
CD40

181             195 196            210 211             225 226            240 241            255 256            270
191        ----------------    ----------------    ----------------    ----------------    ----------------    -----------GAGA
190        ----------------    ----------------    ----------------    ----------------    ---------TAGACA     CCTGGAACAGAG---
189        ----------------    ----------------    -----------TGCC     TTCCTTGCGGTGAA-     ----------------    ---------------
188        ----------------    ----------------    CTGAAACGGAATGCC     TTC-------------    ----------------    ---------------
187        ----------------    -----------AGTTCA   CTGAAACGGAAT---     ----------------    ----------------    ---------------
186        ----------------    ACTGCACAGAGTTCA     CTG-------------    ----------------    ----------------    ---------------
185        ---------TGAGTG     ACTGCACACAGT---     ----------------    ----------------    ----------------    ---------------
184        ----ACTGGTGAGTG     ACTGCAC--------     ----------------    ----------------    ----------------    ---------------
183        AGAAACTGGTGAGTG     A--------------     ----------------    ----------------    ----------------    ---------------
182        AGAAACTGGTGAG--     ---------------     ----------------    ----------------    ----------------    ---------------
181        AG-------------     ---------------     ----------------    ----------------    ----------------    ---------------
X60592-    AGAAACTGGTGAGTG     ACTGCACAGAGTTCA     CTGAAACGGAATGCC     TTCCTTGCGGTGAAA     GCGAATTCTAGACA      CCTGGAACAGAGAGA
CD40

271             285 286            300 301             315 316            330 331            345 346            360
201        ----------------    ----------------    ----------------    ----------------    ----------------    ---------------T
200        ----------------    ----------------    ----------------    ----------------    ----------------    --ACCATCTGCACCT
199        ----------------    ----------------    ----------------    ----------------    ----------------    G ACACCATCTGCACCT
198        ----------------    ----------------    ----------------    ----------------    ---CCTCAGAAACAG     ACACCAA--------
197        ----------------    ----------------    ----------------    ----------------    -CACCTCAGAAACAG     ACAC-----------
196        ----------------    ----------------    ----------------    ------AGCAGAAGG     GCACCTCAG------     ---------------
195        ----------------    ----------------    ----------------    --GTCCAGCAGAAGG     GCACC----------     ---------------
194        ----------------    ------ACTGCGACC     CCAACCTAG------     ----------------    ----------------    ---------------
193        ----------------    ---AATACTGCGACC     CCAACC---------     ----------------    ----------------    ---------------
192        ----------------    ACAAATACTGCGACC     CCA------------     ----------------    ----------------    ---------------
191        CACACTGCCACCAG-     ---------------     ----------------    ----------------    ----------------    ---------------
X60592-    CACACTGCCACCAGC     ACAAATACTGCGACC     CCAACCTAGGGCTTC     GGGTCCAGCAGAAGG     GCACCTCAGAAACAG     ACACCATCTGCACCT
CD40

361             375 376            390 391             405 406            420 421            435 436            450
208        ----------------    ----------------    ----------------    ----------------    ----------------    ---------GATTG
207        ----------------    ----------------    ----------------    ----------------    -----------TTTG     GGGTCAAGCAGATT-
206        ----------------    ----------------    ----------------    ----------CTCAT     GCTCGCCCGGCTT--     ---------------
205        ----------------    ----------------    ----------CTGTG     TCCTGCACCGCTC--     ----------------    ---------------
204        ----------------    ----------------    ----TGAGAGCTGTG     TCCTGCA--------     ----------------    ---------------
203        ----------------    ----------------    CCTGTGAGAGCTGTG     TCC------------     ----------------    ---------------
202        ---AAGAAGGCTGGC     ACTGTA---------     ----------------    ----------------    ----------------    ---------------
201        GAGAAGAAGGCTGGC     AC-------------     ----------------    ----------------    ----------------    ---------------
200        GTGAA----------     ---------------     ----------------    ----------------    ----------------    ---------------
199        GT-------------     ---------------     ----------------    ----------------    ----------------    ---------------
X60592-    GTGAAGAAGGCTGGC     ACTGTACGAGTGAGG     CCTGTGAGAGCTGTG     TCCTGCACCGCTCAT     GCTCGCCCGGCTTTG     GGGTCAAGCAGATTG
CD40

451             465 466            480 481             495 496            510 511            525 526            540
220        ----------------    ----------------    ----------------    ----------------    ----------------    -------------GA
219        ----------------    ----------------    ----------------    ----------------    ----------------    ------ACCCTTGGA
218        ----------------    ----------------    ----------------    ----------------    ----------------    -AA AATGTCACCCTTGGA
217        ----------------    ----------------    ----------------    ----------TGTGT     CATCTGCTTTCGA--     ---------------
216        ----------------    ----------------    ----------------    ----CTCCAATGTGT     CATCTGC--------     ---------------
215        ----------------    ----------------    ----------------    -CTTCTCCAATGTGT     CATC-----------     ---------------
214        ----------------    ----------------    ----------------    TCGGCT TCTTCTCCAATG---     ----------------    ---------------
213        ----------------    ----------------    --------TGCGAGC     CCTGCCCAGTC----     ----------------    ---------------
212        ----------------    ----------------    ------ATCTGCGAGC    CCTGCCCA-------     ----------------    ---------------
211        ----------------    ----------------    --ACCATCTGCGAGC     CCTGC----------     ----------------    ---------------
210        ----------------    -------------CTG    ATACCATCTGCGAGC     ---------------     ----------------    ---------------
209        -TACAGGGGTTTCTG     ATAC-----------     ----------------    ----------------    ----------------    ---------------
```

TABLE 4-continued

CD40 Antisense Sequence Alignment

```
SEQ
ID NO:

208         CTACAGGGGTTTC-- ---------------- ---------------- ---------------- ---------------- ----------------
X60592-     CTACAGGGGTTTCTG ATACCATCTGCGAGC CCTGCCCAGTCGGCT TCTTCTCCAATGTGT CATCTGCTTTCGAAA AATGTCACCCTTGGA
CD40

541         555 556         570 571         585 586         600 601         615 616         630
229         ---------------- ---------------- ---------------- ---------------- ---------------- ----------AGCCC
228         ---------------- ---------------- ---------------- ---------------- ---------------- -----CTGAGAGCCC
227         ---------------- ---------------- ---------------- ---------------- ---------------- ------GTCCCCAGG ATCGGCTGA------
226         ---------------- ---------------- ---------------- ---------------- ----------GTTG TCTGTGGTCCCCAG- ----------------
225         ---------------- ---------------- ---------------- ---------------- ----GACTGATGTTG TCTGTGG-------- ----------------
224         ---------------- ---------------- ----GGCAGGCACAA ACAAGAC-------- ---------------- ----------------
223         ---------------- ---------------C AACAGGCAGGCACAA AC------------- ---------------- ----------------
222         ---------------- --GACCTGGTTGTGC AACAG---------- ---------------- ----------------
221         -----TGTGAGACCA AAGACCTG------- ---------------- ----------------
220         CAAGCTGTGAGACCA A--------------- ---------------- ----------------
219         CAAGCTGTG------- ---------------- ----------------
218         C--------------- ---------------- ----------------
X60592-     CAAGCTGTGAGACCA AAGACCTGGTTGTGC AACAGGCAGGCACAA ACAAGACTGATGTTG TCTGTGGTCCCCAGG ATCGGCTGAGAGCCC
CD40

631         645 646         660 661         675 676         690 691         705 706         720
233         ---------------- ---------------- ---------------- ---------------- ------------CCA AGAAGCCAACCAATA
232         ---------------- ---------------- ---------------- ---TGCTGGTCTTTA TCAAAA---------- ----------------
231         ---------------- ---------------- -------CATCCTCT TGGTGCTGGT----- ---------------- ----------------
230         ---------------- -----------ATCC TGTTTGCCATCCTC- ---------------- ----------------
229         TGGTGGTGATCCC-- ---------------- ---------------- ---------------- ----------------
228         TGGTGGTG------- ---------------- ---------------- ---------------- ----------------
X60592-     TGGTGGTGATCCCCA TCATCTTCGGGATCC TGTTTGCCATCCTCT TGGTGCTGGTCTTTA TCAAAAAGGTGGCCA AGAAGCCAACCAATA
CD40

721         735 736         750 751         765 766         780 781         795 796         810
242         ---------------- ---------------- ---------------- ---------------- ---------------- --------------T
241         ---------------- ---------------- ---------------- ---------------- ---------------- ---------GACTT
240         ---------------- ---------------- ---------------- ---------------- ---------------- CAGTGCAGGAGACTT
239         ---------------- ---------------- ---------------- --------------T CCAACACTGCTGCTC CA-------------
238         ---------------- ---------------- ---------------- ACGATCTTCCTGGCT CCA------------- ----------------
237         ---------------- ---------------- --------------G ACGATCTTCCTGGCT CC-------------- ----------------
236         ---------------- ---------------- ---TCAATTTTCCCG ACGATC---------- ---------------- ----------------
235         ---------------- ---------------G AGATCAATTTTCCCG AC------------- ---------------- ----------------
234         --------CACCCCA AGCAGGAACCC---- ---------------- ---------------- ----------------
X60592-     AGGCCCCCCACCCCA AGCAGGAACCCCAGG AGATCAATTTTCCCG ACGATCTTCCTGGCT CCAACACTGCTGCTC CAGTGCAGGAGACTT
CD40

811         825 826         840 841         855 856         870 871         885 886         900
245         ---------------- ---------------- ---------------- ---------------- --AGACAGTGAGGCT GCACC----------
244         ---------------- ---------------- ---------------- -----TCAGTGCAGG AGAGACAG------- ----------------
243         ---------------- --------CAGGAGG ATGGCAAAGAG---- ---------------- ---------------- ----------------
242         TACATGGATGCCAAC CG-------------- ---------------- ---------------- ----------------
241         TACATGGATGCCA-- ---------------- ---------------- ---------------- ----------------
240         TAC------------ ---------------- ---------------- ---------------- ----------------
X60592-     TACATGGATGCCAAC CGGTCACCCAGGAGG ATGGCAAAGAGAGTC GCATCTCAGTGCAGG AGAGACAGTGAGGCT GCACCCACCCAGGAG
CD40

901         915 916         930 931         945 946         960 961         975 976         990
248         ---------------- ---------------- ---------------- ---------------- --------CAGGGGT GCAGGCAGAAG----
247         ---------------- ---------------- ---------------- ---------------- --------CAGGGGT GCAGGCAGAAG---- ----------------
246         ---------GTGGGC AAACAGGCAGTT--- ---------------- ---------------- ----------------
X60592-     TGTGGCCACGTGGGC AAACAGGCAGTTGGC CAGAGAGCCTGGTGC TGCTGCTGCAGGGGT GCAGGCAGAAGCGGG GAGCTATGCCCAGTC
CD40

991         1004
248         AGT-----------
X60592-     AGTGCCAGCCCCTC
CD40
```

Example 20

PNA Synthesis

Peptide nucleic acids (PNAS) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262 and 6,395,474, herein incorporated by reference.

Method A

PNA oligomers are synthesized in 10 μmol scale on a 433A Applied Biosystems Peptide Synthesizer using commercially available t-butyloxycarbonyl/benzyloxycarbonyl (Boc/Cbz)-protected monomers (Applied Biosystems) and synthesis protocols based on previously published procedures. The coupling efficiency is monitored by qualitative Kaisertest.

Method B

PNA oligomers were synthesized manually using a LabMate 24 parallel synthesizer (Advanced Chemtech) as described for single compound synthesis (Christensen et al, 1995, Koch et al, 1997). Synthesis was performed on solid phase, in 10 μmol scale using a preloaded Boc-Lys(2-Cl-Z)-OH MBHA resin LL (NovaBiochem, 01-64-0006) and commercially available tert-butyloxycarbonyl/benzyloxycarbonyl (Boc/Cbz) protected PNA monomers (Perseptive Biosystems, GEN063010, GEN063011, GEN063012, GEN063013). The MBHA resin was downloaded by preactivition with HBTU (14 eq), N-methyl morpholine (14 eq) and Boc-Lysine (2-Cl-Z)-OH (7 eq) in NMP and loading subsequently determined using standard loading determination via Fmoc measurement (Nova Biochem Catalog, 2003). Completion of coupling was verified by randomized sampling and qualitative Kaiser test. An additional coupling step was included when Kaiser test was non-conclusive. PNAs were deprotected and cleaved in parallel using methods previously applied to single compound synthesis (Christensen et al, 1995; Koch et al, 1997). Purification was performed on a Gilson HPLC system (215 liquid handler, 155 UV/VIS and 321 pump), by reverse phase high performance liquid chromatography (RP-HPLC), using a DELTA PAK (C-18, 15 μm, 300 Å, 300×7.8 mm, 3 mL/min). A linear gradient from solvent A: 0.1% trifluoroacetic acid (Aldrich, T6,220-6) in water to B: 0.1% trifluoroacetic acid in acetonitrile (Burdick & Jackson, AH015-4) was used as the liquid phase. Purity was determined by analytical HPLC (0.1% trifluoroacetic acid in acetonitrile) and composition confirmed by mass spectrometry. A purity level of greater than 95% was generally accomplished. Samples were lyophilized on a FreezeZone 6 (LABCONCO, equipped with a chamber to accommodate racks).

Example 21

Cationic conjugated PNA

Method A

PNA-lysine conjugates were synthesized in 10 μmol scale in parallel on a LabMate 24 parallel synthesizer (Advanced Chemtech) using a solid support bound PNA that was synthesized as described above (Christensen et al, 1995, Koch et al, 1997). The quality of the PNA synthesis was checked prior to peptide conjugation by cleavage and QC of a fraction of the PNA from the support. Peptide synthesis was performed by standard solid-phase tert-butoxycarbonyl (Boc) strategy on support bound PNA, leading to lysine conjugation at the N-terminal end of the PNA. In addition to the N-terminal cationic conjugate each PNA also may contain one or more amino acids, as for example a further lysine unit, at the C-terminus due to the fact that synthesis is performed on Boc-Lys (Z-Cl-Z)OH MBHA resin. The PNA-peptide constructs were synthesized, deprotected and cleaved in parallel. Purification was performed by reversed phase high performance liquid chromatography (RP-HPLC). Purity and composition were determined/confirmed by electrospray ionization mass spectrometry. Synthesis on a 10 μmol scale typically yields >20 mg of PNA oligomer with a purity level of greater than 95%. Samples were lyophilized on a FreezeZone 6 (LABCONCO, equipped with a chamber to accommodate racks).

Method B

The PNA part of the conjugates is assembled using an automated 433 A peptide synthesizer (Applied Biosystems) and commercially available tert-butyloxycarbonyl/benzyloxycarbonyl (Boc/Cbz) protected PNA monomers (Applied Biosystems) according to the published procedures of L. Christensen, et al. (1995), *J. Pept. Sci.* 1, 175-183; and T. Koch, et al. (1997), *J. Pept. Res.* 49, 80-88, for PNA synthesis (Boc chemistry). The synthesis is performed in a 400 μmol scale on MBHA LL polystyrene resin (NovaBiochem), pre-loaded with Boc-Lys(2-Cl-Z)-OH (NovaBiochem) to about 0.1-0.2 mmol/g.

The synthesis of the peptide part of the conjugate is carried out by either Fmoc- or Boc-chemistry, according to standard procedures for solid phase peptide synthesis. For deprotection and cleavage one vol. of a solution of TFA/DMS/m-cresol (1:3:1) is mixed with one vol. of TFA/TFMSA (9:1) and added to the resin. After 1 h of shaking the resin is washed with TFA and one vol. of TFA/TFMSA/m-cresol (8:2:1) was added and the suspension is shaken for another 1.5-6 h. The filtrate is then added to a 10-fold volume of cold diethylether, mixed and centrifuged. The supernatant is removed and the pellet is resuspended in ether. This is repeated three times. The pellet is dried and re-dissolved in water or 0.1% TFA for HPLC purification.

Purification is performed on a Gilson HPLC system (215 liquid handler, 155 UV/VIS and 321 pump), by reverse phase high performance liquid chromatography (RP-HPLC), using a Zorbax (C-3, 5 μm, 300 Å, 250×7.8 mm, 4 mL/min). A linear gradient from solvent A: 0.1% heptafluorobutyric acid in water to B: acetonitrile is used as the liquid phase. Purity is determined by analytical HPLC and composition confirmed by electrospray mass spectrometry. Samples are lyophilized and stored at −20° C. prior to use.

PNA oligomeric conjugates incorporating D-lysine, L-dimethylysine, D-dimethylysine, L-histidine, D-histidine, L-ornithine, D-ornithine, L-homoarginine, D-homoarginine, L-norarginine, D-norarginine, L-homohomoarginine, D-homohomo-arginine, lysine peptoid, 2,4-diamino butyric acid, homolysine or beta-lysine are prepared in like manner using Boc blocked histidine, ornithine, arginine, D-lysine, diaminobutyric and arginine amino acids precursors except as outlined below in the remainder of this example. Other blocking groups can also be selected to protect the amino acid units during synthesis of the conjugate groups.

PNA-Peptoid Conjugates

Oligomers of N-substituted glycines, or "peptoids" are a class of unnatural peptide analogs that resist protease degradation. For the monomer synthesis N-Z-1.4 diaminobutane (5 g, 19.3 mmole) was dissolved in 200 ml dry pyridine and 20 ml DMSO were added. To this solution triethylamine (66.5 mmole, 9.24 ml) was added. Methylbromoacetate (0.871 ml, 9.5 mmole) was diluted in 50 ml dry DMF and added dropwise to the mixture over 3 h, which was then stirred for another 16 h. Di-tert-butyl dicarbonate (29 mmole, 6.33 g dissolved in 20 ml DCM) was added dropwise under stirring and was allowed to react overnight. The resulting compound was extracted with ethyl acetate and identified by TLC. After evaporating the solvents, the compound was saponified with LiOH (0.5 M, THF/MeOH/H$_2$O 1:1:1). The solution was acidified with HCl (3 M) and was extracted with DCM and identified by TLC, Proton NMR and LC-MS. The PNA-peptoid-conjugates were synthesized, deprotected, purified and characterized as described above.

PNA-Peptide Conjugates Containing L-Homo-Arginine and L-Bis Homo Arginine

Bis homoarginine is also known and described in this application as homohomoarginine. For the synthesis of L-homo-arginine- and L-bishomo-arginine-conjugated PNA, Boc-L-lysine(Fmoc)-OH and Boc-L-homo lysine(Fmoc)-OH were used as the initial building blocks and were converted postsynthetically into L-homo-arginine and L-bishomo arginine, respectively. The PNA-Peptide-conjugates were synthesized using Boc-chemistry as described above in this example. After synthesis the Fmoc-protecting groups of the peptide were removed with 20% Piperidine in DMF. The free Amino-groups of the peptide-carrier were guanidinylated by adding a solution of pyrazole carboxamidine-HCl (0.27 g) in 0.363 ml DIEA and 0.637 ml DMF to the peptide conjugate on the resin and reacting at 55° C. for 24 h. Subsequently, the PNA-Peptide conjugates were deprotected, purified and characterized as described above.

Disulfide-Containing Conjugates

The peptide part of the conjugate (H-(dK)$_8$-Cys-NH$_2$) was synthesized by solid phase synthesis on a Sieber Amide Resin (NovaBiochem) using standard peptide synthesis conditions (Fmoc chemistry). After acidic cleavage from the resin (TFA/m-cresol/triisopropylsilane/H$_2$O, 94:2.5:1:2.5) for 1 h at room temperature, the peptide was precipitated into ice-cold diethylether, the precipitate spun down and washed with ether and dried at 55° C. A solution containing 2,2-Dipyridyl-disulfide (300 μmol) in AcCN (1500 μL) was prepared. To a separate solution of 20% pyridine/H$_2$O (3000 μL) was added the peptide H-(dK)$_8$-Cys-NH$_2$ (61 μmol) followed by 1% TEA/H$_2$O to obtain a pH of roughly 8.7. The solution containing the peptide was immediately added to the dipyridyl-disulfide solution. The reaction mixture was allowed to stir for 18 h. The solvents were removed in vacuo and the desired peptide containing a pyridyldisulfide-activated thiol group was purified by RP-HPLC.

The PNA part of the conjugates were synthesized on a previously prepared Boc-PNA-K-MBHA polystyrene resin. Fmoc chemistry was utilized to install the ethylene oxide spacer (O) and the cysteine or penicillamine residue. The resulting thiol-containing compound was cleaved from the resin using the above-described Hi/Low TFMSA cleavage conditions and purified using RP-HPLC as described above. For conjugation, the activated peptide was dissolved in 10% pyridine/H$_2$O (10 mM, 1.5 mL) and the thiol-containing PNA was dissolved in 20% pyridine/H$_2$O (0.1 mM, 7.5 mL) and the pH was adjusted to 10 using 1% TEA/H$_2$O (2 mL). The two solutions were immediately combined while shaking. The pH of the combined solution was 8.2. The reaction was allowed to continue for 18 h. The solvents were removed in vacuo and the desired conjugates were purified by RP-HPLC as described above.

Example 22

Cell Culture, Harvest and Transfection

BCL$_1$ cells were obtained from the American Type Culture Collection and grown in normal growth medium (Dulbecco's modified Eagle medium, supplemented with 10% fetal bovine serum, and antibiotics). Cells were incubated in a humidified chamber at 37° C., containing 5% CO$_2$. Antisense agents were delivered to cells by electroporation (200 V, 13 W, 1000 mFa) using 0.4 cm gap width cuvettes and a BTX electroporator source. Cells were re-plated in normal growth medium and re-incubated for the indicated times prior to harvest.

Primary thioglycollate-elicited macrophages were isolated by peritoneal lavage from 6-8 week old female C57B1/6 mice that had been injected with 1 mL 3% thioglycollate broth 4 days previously. PNAs were delivered to unpurified peritoneal cells by a single 6 ms pulse, 90V, on a BTX square wave electroporator in 1 mm cuvettes. After electroporation, the cells were plated for 1 hour in serum-free RPMI 1640 (supplemented with 10 mM HEPES) at 37° C., 5% CO$_2$ to allow the macrophages to attach. Non-adherent cells were then washed away and the media was replaced with complete RPMI 1640 (10% FBS, 10 mM HEPES). Primary macrophages were activated by treatment with 100 ng/mL rIFN-g (R&D Systems) for 4 hours, followed by 10 μg/mL anti-CD40 antibody (clone 3/23, BD Pharmingen) for the indicated timepoints.

Example 23

Flow Cytometry Analysis

Cells were detached from culture plates with 0.25% trypsin. Trypsin was neutralized with an equal volume of normal growth medium and cells were pelleted. Cell pellets were resuspended in 200 μL staining buffer (phosphate buffered saline containing 2% bovine serum albumin and 0.2% NaN$_3$) containing 1 μg either FITC labeled isotype control antibody or FITC labeled anti-CD40 antibody (clone HM40-3, BD Biosciences). Cells were stained for one hour, washed once with staining buffer, and re-suspended in PBS. Where indicated, cells were resuspended in PBS containing 5 μg/mL propidium iodide to allow for gating only cells that excluded the dye. CD40 surface expression level was determined using a FACScan flow cytometer (Becton Dickinson).

Example 24

Toxicity Assay

Approximately 10$^4$ cells/well were seeded in 96-well plates for 24 h. Media was then replaced with 100 μl media containing increasing amounts of free oligonucleotide. After 24 h, MTS (Promega, Madison, Wis.) was added directly to the culture wells as indicated by the manufacturer and the plates were incubated at 37° C. for 2 h. Absorbance at 490 nm was measured and compared with that of mock-treated samples.

Example 25

Isolation of Total RNA and RT-PCR

Total RNA was isolated using an RNeasy Mini Kit (Qiagen). Two-step RT-PCR was performed using primers complementary to sequences of the CD40 gene (Genbank accession #M83312, incorporated herein as SEQ ID NO: 92). Reverse transcription was performed using a reverse primer (5'-TGATATAGAGAAACACCCCGAAAATGG-3'; SEQ ID NO: 93) complementary to sequence in exon 7. The resulting cDNA was subjected to 35 cycles of PCR using a forward primer consisting of a sequence span identical to that found in exon 5 of the gene (5'-GCCACTGAGACCACTGATAC-CGTCTGT-3'; SEQ ID NO: 94) as well as the reverse primer used for cDNA generation. The resulting PCR products were separated on a 1.6% agarose gel. PCR products were excised and the DNA purified. The resulting products were sequenced using primers used in PCR. Real-time quantitative RT-PCR was performed on total RNA from BCL$_1$ or primary macrophages using an ABI Prism® 7700. Primer and dual labeled probe sequences were as follows:

```
Mouse IL-12 p40:
forward  5'-GCCAGTACACCTGCCACAAA-3',                          SEQ ID No. 95
reverse  5'-GACCAAATTCCATTTTCCTTCTTG-3',                      SEQ ID No. 96
probe    5'-FAM-AGGCGAGACTCTGAGCCACTCACATCTG-TAMRA-3',        SEQ ID No. 97

Mouse CD18:
Forward  5'-CTGCATGTCCGGAGGAAATT-3'                           SEQ ID No. 98
Reverse  5'-AGCCATCGTCTGTGGCAAA-3'                            SEQ ID No. 99
Probe    5'-FAM-CTGGCGCAATGTCACGAGGCTG-TAMRA-3',              SEQ ID No. 100

Mouse CD40, Type 1:
Forward  5'-CACTGATACCGTCTGTCATCCCT-3'                        SEQ ID No. 101
Reverse  5'-AGTTCTTATCCTCACAGCTTGTCCA-3'                      SEQ ID No. 102
Probe    5'-FAM-AGTCGGCTTCTTCTCCAATCAGTCATCACTT-TAMRA-3'      SEQ ID No. 103

Mouse CD40, Type 2:
Forward  5'-CACTGATACCGTCTGTCATCCCT-3'                        SEQ ID No. 104
Reverse  5'-CCACATCCGGGACTTTAAACCTTGT-3'                      SEQ ID No. 105
Probe    5'-FAM-CCAGTCGGCTTCTTCTCCAATCAGTCA-TAMRA-3'          SEQ ID No. 106

Mouse CD40:
Forward  5'-TGTGTTACGTGCAGTGACAAACAG-3'                       SEQ ID No. 107
Reverse  5'-GCTTCCTGGCTGGCACAA-3'                             SEQ ID No. 108
Probe    5'-FAM-CCTCCACGATCGCCAGTGCTGTG-TAMRA-3'              SEQ ID No. 109

Mouse cyclophilin:
Forward  5'-TCGCCGCTTGCTGCA-3'                                SEQ ID No. 110
Reverse  5'-ATCGGCCGTGATGTCGA-3'                              SEQ ID No. 111
Probe    5'-FAM-CCATGGTCAACCCCACCGTGTTC-TAMRA-3'              SEQ ID No. 112
```

Example 26

Western Blot

Cells were harvested in RIPA buffer (phosphate buffered saline containing 1% NP40, 0.1% SDS, and 0.5% sodium deoxycholate). Total protein concentrations were determined by Lowry assay (BioRad) and equal quantities were precipitated with cold acetone by centrifugation. Protein pellets were vacuum dried and resuspended in load dye (Invitrogen) containing 5% mercaptoethanol. Samples were heated to 92° C. for 10 minutes prior to gel loading. Protein samples were separated on 10% PAGE Tris-glycine gels and transferred to PVDF membranes. Membranes were blocked with blocking solution (TBS-T containing 5% non-fat dry milk) and blotted with appropriate antibody. The polyclonal CD40 antibody was obtained from Calbiochem. G3PDH monoclonal antibody was obtained from Advanced Immunochemical, TRADD antibody was obtained from Cell Signalling, and HRP-conjugated secondary antibodies were obtained from Jackson Immunoresearch. Protein bands were visualized using ECL-Plus (Amersham-Pharmacia).

Example 27

ELISA assay

Levels of mouse IL-12 in the supernatants of activated macrophages were measured with mouse IL-12 p40+p70 ELISA kit (Biosource), according to the manufacturer's instructions.

Example 28

Identification of Specific PNA and MOE Inhibitors of CD40 Expression.

A panel of oligomers containing either MOE and PNA backbones was synthesized and are shown in Table 5.

TABLE 5

Sequences of Uniform 2'-MOEs and PNAs targeting the murine CD40 pre-mRNA

| ISIS No PNA | MOE | Sequence of PNA/MOE | Target Region | Target site | SEQ ID NO. |
|---|---|---|---|---|---|
| 208518 | 208342 | GCTAGTCACTGAGCA | 5'-UTR | 389 | 113 |
| 208519 | 208343 | CAAAGTCCCTGCTAG | 5'-UTR | 460 | 114 |
| 208520 | 208344 | AGCCACAAGTCACTC | 5'-UTR | 475 | 115 |
| 208521 | 208345 | AGACACCATCGCAG | Start codon | 529 | 116 |
| 208522 | 208346 | GCGAGATCAGAAGAG | 5'-UTR | 513 | 117 |
| 208523 | 208347 | CGCTGTCAACAAGCA | 3'-Exon 1 | 570 | 118 |
| 208524 | 208348 | CTGCCCTAGATGGAC | 5'-Exon 2 | 60 | 119 |
| 208525 | 208349 | CTGGCTGGCACAAAT | 3'-Exon 2 | 124 | 120 |
| 208526 | 208350 | TGGGTTCACAGTGTC | 3'-Exon 3 | 250 | 121 |
| 208527 | 208351 | CATCTCCATAACTCC | 3'-Exon 4 | 396 | 122 |
| 208528 | 208352 | CTTGTCCAGGGATAA | 3'-Exon 5 | 491 | 123 |
| 208529 | 208353 | CACAGATGACATTAG | 3'-Exon 6 | 553 | 124 |
| 208530 | 208354 | TGATATAGAGAAACA | 3'-Exon 7 | 640 | 125 |
| 208531 | 208355 | TCTTGACCACCTTTT | 5'- Exon 8 | 655 | 126 |
| 208532 | 208356 | CTCATTATCCTTTGG | 3'-Exon 9 | 672 | 127 |
| 208533 | 208357 | GGTTCAGACCAGG | Stop codon | 869 | 128 |
| 208534 | 208358 | AAACTTCAAAGGTCA | 3'-UTR | 914 | 129 |

TABLE 5-continued

Sequences of Uniform 2'-MOEs and PNAs targeting the murine CD40 pre-mRNA

| ISIS No PNA | MOE | Sequence of PNA/MOE | Target Region | Target site | SEQ ID NO. |
|---|---|---|---|---|---|
| 208535 | 208359 | TTTATTTAGCCAGTA | 3'-UTR | 1175 | 130 |
| 208536 | 208360 | AGCCCCACGCACTGG | Intron 3 | 805 | 131 |

Table 5 shows Peptide Nucleic Acid (PNA) and 2'-O-methoxyethyl phosphorothioate oligonucleotide (MOE) sequences, their corresponding ISIS numbers, and their placement on the murine CD40 genome (Genbank Accession No. M94129, provided herein as SEQ ID NO: 132). Sequences are provided in generic form. For PNAs, sequences read from the aminoterminal (H—) to the carboxamide (—NH$_2$). Lysine inserted at the carboxamide terminal for all sequences (hence for ISIS 208518, full sequences should read H-GCTAGTCACTGAGCA-Lys-NH$_2$; SEQ ID NO: 113). For MOEs, sequences read from 5' to 3'. Purity generally exceeded 95% as assessed by analytical HPLC (UV 260 nm).

These oligomers were designed to regions of the murine CD40 pre-mRNA that could potentially either alter splicing or inhibit translation, both of which are validated non-RNase dependent mechanisms (Sazani et al., Taylor et al., Baker et al. 1991, Chiang et al. 1991, Karras et al.). The MOE and PNA oligomers were delivered by electroporation into BCL$_1$ cells, a mouse B cell line that constitutively expresses high levels of CD40. Following a 48 hour incubation period, cells were harvested and analyzed for surface expression of CD40 by flow cytometry. The activities of the PNA oligomers were compared to those of the MOE oligomers of identical sequence and length. Isis 29848 (NNNNNNNNNNNNNNNNNNNN; SEQ ID NO: 133) and ISIS 117886 (TCTCACTCCTATCCCAGT; SEQ ID NO: 134; a 2'-MOE gapmer with phosphorothioate backbone, targeted to murine CD40. 2' MOE shown in bold) were included in each screen as negative and positive controls, respectively, for RNase H-mediated CD40 inhibition. The results are shown in Table 6 expressed as percent of control (no oligo treatment).

TABLE 6

Effect of PNA and Uniform 2' MOE Oligomers on CD40 expression

| MOE | CD40 Expression (% of control) | PNA | CD40 Expression (% of control) |
|---|---|---|---|
| no oligomer | 100 | no oligomer | 100 |
| 29848 | 89 | 29848 | 100 |
| 117886 | 32 | 117886 | 38 |
| 208342 | 90 | 208518 | 114 |
| 208343 | 88 | 208519 | 96 |
| 208344 | 86 | 208520 | 82 |
| 208345 | 64 | 208521 | 61 |
| 208346 | 79 | 208522 | 92 |
| 208347 | 40 | 208523 | 50 |
| 208348 | 48 | 208524 | 71 |
| 208349 | 61 | 208525 | 77 |
| 208350 | 90 | 208526 | 105 |
| 208360 | 75 | 208536 | 98 |
| 208351 | 90 | 208527 | 128 |
| 208352 | 50 | 208528 | 58 |

TABLE 6-continued

Effect of PNA and Uniform 2' MOE Oligomers on CD40 expression

| MOE | CD40 Expression (% of control) | PNA | CD40 Expression (% of control) |
|---|---|---|---|
| 208353 | 26 | 208529 | 34 |
| 208354 | 50 | 208530 | 49 |
| 208355 | 66 | 208531 | 86 |
| 208356 | 42 | 208532 | 62 |
| 208357 | 86 | 208533 | 78 |
| 208358 | 92 | 208534 | 116 |
| 208359 | 62 | 208535 | 103 |

Sequences (SEQ ID NO: 116, 117, 118, 119, 120, 123, 124, 125, 127, 128, 130, 131) of compounds showing over 20% inhibition of CD40 expression (levels of 80% or less in Table 6) are preferred.

There was a strong correlation between the activities of PNA and MOE oligomers designed to the same target sites, as demonstrated by both paired sample t-test and Spearman rank correlation (p<0.001, in both cases). These results demonstrate that the sequence dependence of CD40 inhibitory activity is similar for MOE and PNA based inhibitors. Inhibitors based on MOE and PNA backbone chemistry were found to be of equal efficacy as determined by the flow cytometry. A PNA targeted towards the 3' end of exon 6, ISIS 208529 (SEQ ID NO: 124), was found to be the most active sequence. The corresponding MOE sequence, ISIS 208353 was also the most active within the series of MOE compounds. To further assess the specificity of ISIS 208529, CD40 levels were measured by western blot from BCl$_1$ cells electroporated with either the parent PNA (ISIS 208529), a PNA containing a four base mismatch (ISIS 256644; CACTGATCAGATAAG; SEQ ID NO: 135), or one of two PNAs of unrelated sequences (ISIS 256645; ACTAGTGCTAGCGTC; SEQ ID NO:136, and ISIS 256646; CGTCATGATACCGAT; SEQ ID NO: 137). In each case, protein was harvested and analyzed 48 hours after electroporation. Using an antibody specific for the C-terminal region of the CD40 Protein, western blot analysis showed that none of the three mismatched PNAs affected CD40 expression, whereas the inhibition of CD40 expression by ISIS 208529 was confirmed.

Example 29

Mode of Action of the PNA Inhibitor ISIS 208529.

The target sequence for ISIS 208529 is located on the 3' end of exon 6 of the primary murine CD40 transcript, abutting the splice junction, and is therefore likely to affect splicing. The naturally occurring splice forms of murine CD40 have been previously described (Tone, M., Tone, Y., Fairchild, P. J., Wykes, M., and Waldmann, H. (2001) *Proc. Natl Acad. Sci. U.S.A.* 98, 1751-1756). The type 1 transcript, which retains exon 6, is the predominant form. Its translation product is the canonical membrane-bound, signaling-competent CD40 protein. The type 2 transcript is lower in abundance and does not contain exon 6. The omission of exon 6 causes a frame shift in codons contained in exons 7, 8, and 9, and leads to mistranslation of the sequence encoding for the transmembrane domain and truncation of the protein due to a now in-frame stop codon in exon 8. The presence of the type 2 transcript interferes with CD40 signaling. Tone et al., 2001. In order to verify the mechanism by which ISIS 208529 reduces the expression of cell surface CD40 expression, RT-PCR was performed on RNA isolated from both treated and untreated cells using primers seated in exons 5 and 7. A sequence specific, PNA mediated shift in the relative abundance of the two splice forms was observed upon treatment with ISIS 208529. No change in relative abundance in splice forms was observed in cells treated with the four base mismatched PNA, ISIS 256644. The identities of the splice forms were verified by sequencing of the two RT-PCR products.

Example 30

Evaluation of PNAs Targeting Sequences Surrounding the Binding Site for ISIS 208529.

Further optimization of inhibitor binding was performed by designing additional PNA oligomers targeted to sites adjacent to the ISIS 208529 binding site. The PNA oligomers were designed to bind to 15 nt spans of target RNA within a range of 10 nt upstream and downstream of the ISIS 208529 binding site on the primary transcript as shown in Table 7.

TABLE 7

Optimization of PNA oligomers target to CD40

| Isis # | Sequence | SEQ ID No. |
|---|---|---|
| 208529 | H-CACAGATGACATTAG-Lys-NH$_2$ | 124 |
| 256634 | H-ATTAGTCTGACTCGT-Lys-NH$_2$ | 138 |
| 256635 | H-ACATTAGTCTGACTC-Lys- | 139 |
| 256636 | H-TGACATTAGTCTGAC-Lys- | 140 |
| 256637 | H-GATGACATTAGTCTG-Lys- | 141 |
| 256638 | H-CAGATGACATTAGTC-Lys- | 142 |
| 256639 | H-CTGGACTCACCACAG-Lys- | 143 |
| 256640 | H-GGACTCACCACAGAT-Lys- | 144 |
| 256641 | H-ACTCACCACAGATGA-Lys- | 145 |
| 256642 | H-TCACCACAGATGACA-Lys- | 146 |
| 256643 | H-ACCACAGATGACATT-Lys- | 147 |
| 256644 | H-CACTGATCAGATAAG-Lys- | 135 |
| 256645 | H-ACTAGTGCTAGCGTC-Lys- | 136 |
| 256646 | H-CGTCATGATACCGAT-Lys- | 137 |
| 286422 | H-ACATTAG-Lys- | 148 |
| 286243 | H-GACATTAG-Lys- | 149 |
| 286244 | H-TGACATTAG-Lys- | 150 |
| 286245 | H-ATGACATTAG-Lys- | 151 |
| 286246 | H-GATGACATTAG-Lys- | 152 |
| 286247 | H-AGATGACATTAG-Lys- | 153 |
| 286248 | H-CAGATGACATTAG-Lys- | 154 |
| 286249 | H-ACAGATGACATTAG-Lys- | 155 |
| 298841 | H-CCACAGATGACATTAG-Lys- | 156 |
| 298842 | H-ACCACAGATGACATTAG-Lys- | 157 |
| 298843 | H-CACCACAGATGACATTAG-Lys- | 158 |
| 298844 | H-TCACCACAGATGACATTAG-Lys- | 159 |

TABLE 7-continued

Optimization of PNA oligomers target to CD40

| Isis # | Sequence | SEQ ID No. |
|---|---|---|
| 298845 | H-CTCACCACAGATGACATTAG-Lys- | 160 |

The sequences align as shown below.

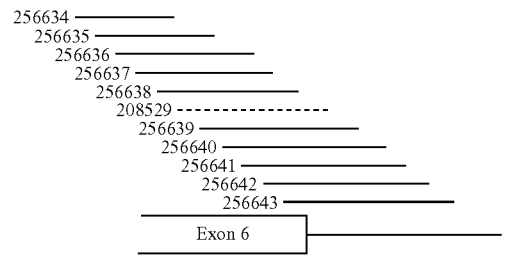

The activities of the resulting ten PNAs, as well as that of ISIS 208529, were evaluated in parallel by western blot. Eight of the ten PNAs (SEQ ID NO: 138, 139, 142, 143, 144, 145, 146, and 147) demonstrated a level of activity similar to that of ISIS 208529, and are therefore preferred. Two PNAs, ISIS 256636 and ISIS 256637 (SEQ ID NO: 140 and 141), positioned slightly upstream from the 3' exon 6 splice site, failed to inhibit CD40 expression. Examination of the primary sequences of the two inactive PNAs did not reveal any obvious features, such as a high guanosine content, that might promote the formation of undesirable secondary structure. Likewise, the RP-HPLC elution profiles for these two compounds did not indicate a tendency for self-aggregation. Furthermore, examination of the target RNA sequence did not reveal secondary structure that might limit target accessibility.

Example 31

The Effect of PNA Length on CD40 Inhibitory Activity.

The effect of PNA length on activity was assessed by systematic variation of length of the PNA inhibitor from 7 to 20 monomer units. For the initial examination of length effects, 13 PNAs were designed and synthesized (Table 3). The first set, consisting of PNAs of 7 to 14 units in length, were all targeted to portions of the binding site of ISIS 208529. Each of these compounds as well as the 15-mer parent, ISIS 208529, were electroporated into BCL$_1$ cells at a final concentration of 10 µM. Three days following delivery, the cells were harvested and analyzed by western blot for CD40. G3PDH protein levels were also measured to verify equal protein loading. While no apparent reduction in CD40 levels was observed in cells treated with compounds ranging from 7-11 units in length, inhibition of CD40 expression was observed with compounds ranging from 12-15 units in length. The efficacy of the PNA inhibitors was found to increase with increasing length, up to a PNA length of about 14 units, where efficacy reached a level similar to that displayed by the lead 15-mer PNA, ISIS 208529. Subsequently, a second set of PNAs was examined covering a range of 12 to 20 units in length. PNAs were electroporated into BCL$_1$ cells at various concentrations to determine their relative potencies. Compounds were evaluated for their ability to inhibit CD40 cell surface expression by flow cytometry. Potency was found to increase with increasing length, reaching a plateau at 14 unit length, beyond which no additional gain was detected upon increasing length. This observation suggests that the potency of ISIS 208529 is not limited by its length, and that potency cannot be improved by increasing the length of this PNA. At this target site, $EC_{50}$ values were in the range of 0.6 to 0.9 μM for all PNAs of 14 units or longer as is shown in Table 8 where EC50 values and 95% confidence intervals were determined by nonlinear regression analysis using a defined top and bottom of 400 and 100, respectively.

TABLE 8

Effect of length on PNA oligomer inhibitory activity

| Length | ISIS NO. | EC50 | 95% confidence interval |
|---|---|---|---|
| 12 | 286247 | 21.1 | 13.0 to 34.4 |
| 13 | 286248 | 1.85 | 1.59 to 2.16 |
| 14 | 286249 | 0.90 | 0.78 to 1.04 |
| 15 | 208529 | 0.87 | 0.75 to 1.00 |
| 16 | 298841 | 0.58 | 0.40 to 0.83 |
| 17 | 298842 | 0.79 | 0.50 to 1.23 |
| 18 | 298843 | 0.86 | 0.71 to 1.03 |
| 19 | 298844 | 0.57 | 0.44 to 0.74 |
| 20 | 298845 | 0.71 | 0.52 to 0.97 |

Example 32

Dose and Time Dependence of CD40 Inhibitory Activity by ISIS 208529.

The dose dependent reduction of cell surface CD40 protein upon treatment of $BCL_1$ cells with ISIS 208529 (SEQ ID NO: 124) was evaluated by flow cytometry and was further supported by verification of CD40 protein depletion by western blot. Specificity was verified by inclusion of a PNA containing a four base mismatch (ISIS 256644; SEQ ID NO: 135). ISIS 208529 showed an increasing dose response curve across a concentration range of 16, 8, 4, 2, 1, 0.5 and 0.25 μM range where as the mismatch compound did not. In order to assess the effect of ISIS 208529 over time, western blot analysis was applied to study the effect of a single dose (10 μM) of ISIS 208529 for eight days following electroporation. Maximal inhibition of CD40 expression was observed four days post treatment and persisted for at least five days. At day eight, the level of CD40 expression was back to values found for the no-treatment control. No change in CD40 expression levels was observed in cells treated with the four base mismatched PNA (ISIS 256644).

Example 33

Inhibitory Activity of ISIS 208529 on CD40 Dependent IL-12 Production in Primary Murine Macrophages.

The functional consequences of PNA-induced alternative splicing in primary murine macrophages were examined. Thioglycollate-elicited mouse peritoneal cells were electroporated with various doses of ISIS 208529 (SEQ ID NO: 124) or with the PNA containing a four base mismatch, ISIS 256644 (SEQ ID NO: 135). After electroporation, macrophages were selected by adherence to tissue culture plates and treated with IFN-α for 4 hours to induce CD40 cell surface expression, and then stimulated with an activating CD40 antibody for 24 hours. CD40 signaling in macrophages results in production of multiple cytokines, including IL-12. The level of IL-12 in the supernatant of PNA-treated macrophages after CD40 activation was examined by an ELISA assay. Electroporation of the macrophages with ISIS 208529 resulted in a dose-dependent reduction in IL-12 production. Delivery of 3 μM ISIS 208529 to macrophages by electroporation resulted in 75% inhibition of IL-12 production compared to macrophages electroporated with no PNA. A maximal inhibition of 85% relative to the untreated control was obtained with 10 μM ISIS 208529. Macrophages electroporated with the mismatch control PNA (ISIS 256644) showed no decrease in IL-12 production in response to PNA treatment. Examination of the level of CD40 protein by western blot showed a dose dependent reduction in CD40 protein following treatment with ISIS 208529, which correlated to the decrease in IL-12 production. No reduction in CD40 protein was found after treatment with the mismatch control ISIS 256644. Examination of the CD40 splice forms by quantitative RT-PCR showed a 70% decrease in the predominant type 1 splice form, and a 2-fold increase in the alternative type 2 splice form, at 3 μM ISIS 208529. The four base mismatch control, ISIS 256644, had no significant effect on the relative abundance of the CD40 splice forms, indicating that inhibitory activity was dependent on Watson-Crick complementarity.

Example 34

Effect of ISIS 208529 Peptide Conjugation on CD40 Cell Surface Expression in $BCL_1$ Cells and in Macrophages.

In order to obtain a PNA with potential to act without the use of a delivery vehicle, the active PNA, ISIS 208529 (SEQ ID NO: 124), was conjugated with eight lysines at the N-terminus to give ISIS 278647. In $BCL_1$ cells that were treated with ISIS 278647 at 10 μM, the relative abundance of the CD40 type 1 transcript was decreased and the abundance of the type 2 transcript was increased as determined by standard RT-PCR and real-time quantitative RT-PCR. ISIS 278647 caused an 85% decrease in the type 1 transcript and a greater than 3 fold increase in the type 2 transcript. Neither the unconjugated lead PNA (ISIS 208529) nor an eight lysine conjugated, four base mismatched PNA (ISIS 287294; SEQ ID NO: 135) had any effect on the relative abundance of either splice variant or on total CD40 transcript, relative to the untreated control. Analysis of the protein lysates by western blot, using an antibody that recognizes the C-terminal region of the canonical CD40 protein, showed that ISIS 278647 promotes CD40 protein depletion, whereas the unconjugated PNA, ISIS 208529, and the four base mismatched control, ISIS 287294, do not. These results demonstrate that redirection of splicing and loss of the CD40 protein encoded by the type 1 transcript variant is dependent on both PNA sequence and inclusion of the eight lysine carrier when no delivery vehicle is used.

The effect of lysine conjugation of ISIS 208529 (SEQ ID NO: 124) on CD40 expression, and on the relative abundance of the type 1 and type 2 transcripts, was also examined in primary murine macrophages. Adherent peritoneal macrophages were incubated in with various concentrations of unconjugated or conjugated PNA for 16 hours and CD40 expression then induced by IFN-α. The reduction of CD40 protein in the PNA treated cells was examined by western blot. No reduction in CD40 protein was observed after treatment with ISIS 208529, while a modest reduction in CD40 protein was observed in macrophages treated with a 4 lysine conjugated PNA of the same sequence (ISIS 278643; SEQ ID NO: 124). In contrast, treatment with the eight lysine conjugated CD40 PNA of the same sequence (ISIS 278647) resulted in a dramatic, dose-dependent decrease in CD40 protein. Treatment with ISIS 278647 at 10 μM resulted in reduction of CD40 protein to levels undetectable by western blot, indicating that the eight lysine conjugated PNA was readily taken up by the primary macrophages and that carrier conjugation did not prevent the PNA from binding to its target and from attenuating CD40 protein expression. Under similar conditions, an eight lysine conjugated four base mismatch control PNA (ISIS 287294; SEQ ID NO: 135) caused no reduction in CD40 protein, indicating that the observed reduction in CD40 protein is sequence specific. Analysis of the CD40 splice forms by quantitative RT-PCR demonstrated that the eight lysine conjugated CD40 PNA (ISIS 278647) caused a substantial reduction in CD40 type 1 mRNA with a concomitant 5-fold induction of the CD40 type 2 transcript. The eight lysine conjugated four base mismatch PNA (ISIS 287294) had no significant effect on the relative levels of the type 1 and type 2 splice forms.

Example 35

Inhibitory Activity of Further PNA Cationic Conjugate Compounds Against CD40

A series of PNA conjugate compounds of identical sequence to ISIS 208529, i.e., CACAGATGACATTAC; Seq ID NO. 124, were prepared and tested in BCL-1 cells using flow cytometry for free uptake at 10 μM (FACS). The following abbreviations are used to identify the components of each of the conjugates: (C)=C-terminal, (N)=N-terminal, aca=6-aminocaproic acid, aoc=aminooctanoic acid, βA=beta-alanine, βK=beta-lysine, aca=amino hexanoic acid, adc=amino dodecanoic acid, O=8-amino-3,6-dioxaoctanoic acid, Dab=L-2-4-diaminobutyric acid, Ci=L-citrulline, ab=4-aminobutyric acid, hR=L-homo arginine, hhR=L-homohomo arginine, norR=L-nor arginine, G=glycine, pK=lysine-peptoid, H=L-histidine, DhR=D-homo arginine, dR=d-arginine, inp=isonipecotic acid, amc=4-aminomethyl-cyclohexane carboxylic acid, dmK=L-dimethyl lysine, Pen=penicillamine, Ada=adamantane acetyl, Pam=palmityl, Ibu=(S)-(+)-ibuprofen, CHA=cholic acid, Chol=cholesteryl formyl, mm=mismatch PNA.

The compounds and test results are as are shown in Table 9.

TABLE 9

Additional PNA Cationic Conjugate Compounds of SEQ ID NO: 124

| Isis #-Lot# | N-terminal modification | C-terminal modification | notes | CD40 Protein (% UTC @ 10 μM) | $t_{1/2}$ [h] in 25% mouse serum | Est. $t_{1/2}$ [h] in 100% mouse serum |
|---|---|---|---|---|---|---|
| 208529-1 | | K | | 80, 98, 100 | stable | stable |
| 278640-1 | K | K | | 80 | n.d. | |
| 278641-1 | $K_2$ | K | | 90 | n.d. | |
| 278642-1 | $K_3$ | K | | 80 | n.d. | |
| 278643-1 | $K_4$ | K | | 100 | n.d. | |
| 278644-1 | $K_5$ | K | | 70 | n.d. | |
| 278645-1 | $K_6$ | K | | 50 | n.d. | |
| 278646-1 | $K_7$ | K | | 30 | n.d. | |
| 278647-1 | $K_8$ | K | | 20, 30, 35, 30, 15 | 5.7 | 1.4 |
| 287294-1 | $K_8$ | K | 4 mm | 100 | n.d. | |
| 287293-1 | $K_6$ | K | 4 mm | 100 | n.d. | |
| 284381-1 | | $K_2$ | | 95 | n.d. | |
| 279866-1 | | $K_4$ | | 85 | 6.5 | 1.6 |
| 284375-1 | | $K_8$ | | 40, 35, 35, 40, 35, 45, 73, 68 | 1 | 0.25 |
| 290075-1 | R | K | | 100 | n.d. | |
| 290076-1 | $R_2$ | K | | 90 | n.d. | |
| 290077-1 | $R_3$ | K | | 90 | n.d. | |
| 290078-1 | $R_4$ | K | | 80 | n.d. | |
| 290079-1 | $R_5$ | K | | 80 | n.d. | |
| 297780-1 | $R_6$ | K | | 75 | n.d. | |
| 290081-1 | $R_7$ | K | | 70 | n.d. | |
| 290082-2 | $R_8$ | K | | 60 | 3.2 | 0.8 |
| 301010-1 | D-$R_8$ | K | | 49 | n.d. | |
| 299870-1 | | $K_5RK_2$ (SEQ ID NO: 171) | | 48 | n.d. | |
| 299871-1 | | D($K_5RK_2$) (SEQ ID NO: 172) | | 53 | n.d. | |
| 284382-1 | $K_2$ | $K_2$ | | 85 | n.d. | |
| 279867-1 | $K_4$ | $K_4$ | | 75 | n.d. | |
| 284383-1 | Ada-O | $K_2$ | | 80 | n.d. | |
| 284384-1 | Ada-O-$K_2$ | $K_2$ | | 85 | n.d. | |
| 279975-1 | Ada-O | $K_4$ | | 95 | n.d. | |
| 279976-1 | Ada-O-$K_4$ | $K_4$ | | 75 | n.d. | |
| 284376-1 | Ada-O | $K_8$ | | 40 | n.d. | |
| 284385-1 | Pam-O | $K_2$ | | n/a tox. | n.d. | |
| 284386-1 | Pam-O-$K_2$ | $K_2$ | | n/a tox. | n.d. | |
| 283582-1 | Pam-O | $K_4$ | | 70 | n.d. | |
| 283583-1 | Pam-O-$K_4$ | $K_4$ | | 60 | n.d. | |
| 284377-1 | Pam-O | $K_8$ | | n/a tox. | n.d. | |
| 290061-1 | Ibu-O | $K_2$ | | 80 | n.d. | |
| 287086-1 | Ibu-O | $K_8$ | | 30 | 1 | 0.25 |
| 311573-1 | Ibu-O-$K_8$ | K | | n.d. | n.d. | |
| 290063-1 | CHA-O | $K_2$ | | 95 | n.d. | |
| 290064-1 | Chol-O- | $K_2$ | | n/a tox. | n.d. | |

TABLE 9-continued

Additional PNA Cationic Conjugate Compounds of SEQ ID NO: 124

| Isis #-Lot# | N-terminal modification | C-terminal modification | notes | CD40 Protein (% UTC @ 10 μM) | $t_{1/2}$ [h] in 25% mouse serum | Est. $t_{1/2}$ [h] in 100% mouse serum |
|---|---|---|---|---|---|---|
| 292097-1 | CHA-O-$K_8$ | K | | 55 | n.d. | |
| 292098-1 | Chol-O-$K_8$ | K | | n/a tox. | n.d. | |
| 298110-1 | Branch1-K | K | | 60 | n.d. | |
| 298111-1 | Branch3-K | K | | 85 | n.d. | |
| 298112-1 | Branch4-K | K | | 60 | n.d. | |
| 298113-1 | Branch5-K | K | | 75 | n.d. | |
| 298114-1 | Branch6-K | K | | 70 | n.d. | |
| 298116-1 | Branch2-K | K | | 40 | n.d. | |
| 303537-1 | RacaRRacaRRacaRR | K | | 23, 29 | 2 | 0.5 |
| 303540-1 | KacaKKacaKKacaKK | K | | 70 | n.d. | |
| 303538-1 | RacaRacaRacaRacaRacaR | K | | 40 | n.d. | |
| 309743-1 | dR.aca.dR.dR.aca.dR.dR.aca.dR.dR | K | | 35 | n.d. | |
| 303539-1 | KacaKacaKacaKacaKacaKacaK | K | | 61 | n.d. | |
| 291341-1 | KGKKGKGK | K | | 87 | n.d. | |
| 291342-1 | KaocKKaocKaocK | K | | 79 | n.d. | |
| 330890-1 | hR-O-hR-hR-O-hR-O-hR-hR | K | | 25 at 3 uM | 59 | 12 |
| 338896-1 | hR-O-R-hR-O-R-hR-O-R-hR | K | | 49 | 2 | 0.5 |
| 338897-1 | R-O-hR-R-O-hR-R-O-hR-R | K | | 54 | 4 | 1 |
| 315570-1 | RacaRRacaRRacaRR-PKKKRKV | K | | 25 | n.d. | |
| 315571-1 | RacaRRacaRRacaRR-KKVKPKR | K | | 41 | n.d. | |
| 315650-1 | PKKKRKV-RacaRRacaRRacaRR | K | | 44 | n.d. | |
| 315573-1 | KKVKPKR-RacaRRacaRRacaRR | K | | 31 | n.d. | |
| 309860-1 | R-βA-RR-βA-RRβA-RR | K | | 27 | n.d. | |
| 309883-1 | R-abu-RR-abu-RR-abu-RR | K | | 26 | n.d. | |
| 309861-1 | R-aoc-RR-aoc-RR-aoc-RR | K | | 25 | n.d. | |
| 309864-1 | R-aca-RR-aca-RR-aca-RR-aca | K | | 20 | n.d. | |
| 309862-1 | R-O-RR-O-RR-O-RR | K | | 24 | 2 | 0.5 |
| 309865-1 | RR-aca-RR-aca-RR | K | | 40 | n.d. | |
| 309866-1 | R-aca-RR-aca-RR | K | | 58 | n.d. | |
| 309884-1 | R-inp-RR-inp-RR-inp-RR | K | | 29 | n.d. | |
| 309885-1 | R-amc-RR-amc-RR-amc-RR | K | | 27 | n.d. | |
| 291350-2 | (βK)$_8$ | K | | 66 | n.d. | |
| 309843-1 | βK-βK-KKKK-βK-βK | K | | 52 | n.d. | |
| 309844-1 | (K-βK)$_4$ | K | | 62 | n.d. | |
| 309845-1 | KK-βK-KK-βK-KK | K | | 61 | n.d. | |
| 303536-1 | D-(Orn)$_8$ | K | | 67 | n.d. | |
| 303327-1 | | (Orn)$_8$ | | 64 | n.d. | |
| 301011-2 | (Orn)$_8$ | K | | 77 | >48 | >12 |
| 309143-1 | Orn-Orn-KKKK-Orn-Orn | K | | 52 | n.d. | |
| 309144-1 | (K-Orn)$_4$ | K | | 42 | n.d. | |
| 309145-1 | KK-Orn-KK-Orn-KK | K | | 34 | 19 | 4.75 |
| 311069-1 | KKKKK-Orn-KK | K | | 50 | n.d. | |
| 311070-1 | KK-Orn-KKKKK | K | | 53 | n.d. | |
| 287292-2 | (dK)$_8$ | K | | 54 | stable | >48 |
| 305390-1 | dKdK-KKKK-dKdK | K | | 60 | n.d. | |
| 305391-1 | K-dK-K-dK-K-dK-K-dK | K | | 69 | n.d. | |
| 305392-1 | KK-dK-KK-dK-KK | K | | 62 | stable | >48 |
| 311071-1 | KKKKK-dK-KK | K | | 61 | n.d. | |
| 311072-1 | KK-dK-KKKKK | K | | 59 | n.d. | |
| 305393-1 | RRKKKKKRR | K | | 65 | n.d. | |
| 305394-1 | KRKRKRKR | K | | 52 | n.d. | |
| 305395-1 | KKRKKRKK | K | | 43 | 2.5 | 0.6 |
| 308579-1 | (hK)$_8$ | K | | 31 | 18 | 4.5 |
| 308580-1 | hKhK-KKKK-hKhK | K | | 34 | n.d. | |

TABLE 9-continued

Additional PNA Cationic Conjugate Compounds of SEQ ID NO: 124

| Isis #-Lot# | N-terminal modification | C-terminal modification | notes | CD40 Protein (% UTC @ 10 μM) | $t_{1/2}$ [h] in 25% mouse serum | Est. $t_{1/2}$ [h] in 100% mouse serum |
|---|---|---|---|---|---|---|
| 308581-1 | K-hK-K-hK-K-hK-K-hK | K | | 32 | n.d. | |
| 308582-1 | KK-hK-KK-hK-KK | K | | 31 | 7.5 | 1.9 |
| 316409-1 | (Dab)$_8$ | K | | 77 | >48 | >12 |
| 316410-1 | (Dab)$_2$-K-(Dab)$_2$-K-(Dab)$_2$ | K | | 64 | n.d. | |
| 316411-1 | (Dab-K)$_4$ | K | | 52 | n.d. | |
| 316412-1 | KK-Dab-KK-Dab-KK | K | | 38 | 40 | 10 |
| 316427-1 | (K-ab)$_8$ | K | | 47 | n.d. | |
| 316428-1 | (K-(K-ab))$_4$ | K | | 41 | n.d. | |
| 316429-1 | KK-(K-ab)-KK-(K-ab)-KK | K | | 39 | n.d. | |
| 316430-1 | (K-ab)$_2$-K-(K-ab)$_2$-K-(K-ab)$_2$ | K | | 55 | n.d. | |
| 325598-1 | (dmK)$_8$ | K | | 71 | stable | |
| 325599-1 | (K-dmK)$_4$ | K | | 53 | n.d. | |
| 325600-1 | KK-dmK-KK-dmK-KK | K | | 41 | 23 | 5.8 |
| 325601-1 | (dmK)$_2$-K-(dmK)$_2$-K-(dmK)$_2$ | K | | 63 | n.d. | |
| 326744-1 | (hR)$_8$ | K | | 30, 20 | 15.4 | 3.9 |
| | (hhR)$_8$ | K | | n/a | stable | stable |
| 333677-1 | (K-hR)$_4$ | K | | 44 | n.d. | |
| 333678-1 | KK-hR-KK-hR-KK | K | | 36 | n.d. | |
| 338894-1 | (DhR)$_8$ | K | | n/a tox. | n.d. | |
| 338895-1 | RR-DhR-RR-DhR-RR | K | | 67 | 23.6 | 5.9 |
| 326746-1 | (norR)$_8$ | K | | 90 at 3 uM | >48 | >12 |
| 333674-1 | G(pK)$_8$ | K | | 56 | >48 | >12 |
| 333675-1 | (K-pK)$_4$ | K | | 70 | n.d. | |
| 333676-1 | KK-pK-KK-pK-KK | K | | 60 | 29 | 7.25 |
| 332593-1 | (H)$_8$ | K | | 64 | 44.5 | 11 |
| 332672-1 | (KH)$_4$ | K | | 73 | n.d. | |
| 332673-1 | KKHKKHKK | K | | 52 | 5.7 | 1.4 |
| 332674-1 | KKGKKGKK | K | | 59 | n.d. | |
| 313685-1 | K$_7$-Ci | K | | 65 | n.d. | |
| 313686-1 | K$_6$-Ci-K | K | | 59 | n.d. | |
| 313687-1 | K$_5$-Ci-K$_2$ | K | | 53 | n.d. | |
| 313688-1 | K$_4$-Ci-K$_3$ | K | | 52 | n.d. | |
| 313689-1 | K$_3$-C-K$_4$ | K | | 57 | n.d. | |
| 313690-1 | K$_2$-Ci-K$_5$ | K | | 55 | n.d. | |
| 313691-1 | K-Ci-K$_6$ | K | | 57 | n.d. | |
| 313692-1 | Ci-K$_7$ | K | | 52 | n.d. | |
| 313693-1 | KK-Ci-KK-Ci-KK | K | | 65, 67 | n.d. | |
| 310755-1 | K$_8$-βA | K | | 43 | n.d. | |
| 310756-1 | K$_8$-aca | K | | 48 | n.d. | |
| 310757-1 | K$_8$-aoc | K | | 54 | n.d. | |
| 310758-1 | K$_8$-adc | K | | 68 | n.d. | |
| 291335-2 | K$_8$-aoc-aoc | K | | 62 | n.d. | |
| 310753-1 | K$_8$-O | K | | 44 | n.d. | |
| 310754-1 | K$_8$-O-O | K | | 46 | n.d. | |
| 330775-1 | (dK)$_8$-FRGO | K | | 46 | 2.8 | 0.7 |
| 330776-1 | (dK)$_8$-dF-dRGO | K | | 54 | n.d. | |
| 330777-1 | (dK)$_8$-ALALGO | K | | 37 | 8.7 | 2.2 |
| 330778-1 | (dK)$_8$-dA-dLdAdLGO | K | | 36 | n.d. | |
| 335296-1 | (dK)$_8$-WEHDLO | K | | 59 | >48 | .12 |
| 335299-1 | (dK)$_8$-dW-dE-dH-dD-dL-O | K | | 64 | n.d. | |
| 335297-1 | (dK)$_8$-D-E-V-D-L-O | K | | 90 | >48 | >12 |
| 335300-1 | (dK)$_8$-dD-dE-dV-dD-dL-O | K | | 89 | n.d. | |
| 330781-1 | (dK)$_8$-G-F-L-G-O | K | | 38 | >48 | >12 |
| 330782-1 | (dK)$_8$-G-dF-dL-G-O | K | | 39 | n.d. | |
| 339746-1 | dK$_8$-Cys-disulfide-Cys-O | K | | 41 | 17 | 4.25 |
| 339747-1 | dK$_8$-Cys-disulfide-Pen-O | K | | 35 | 30 | 7.5 |

The Branch conjugates have the following structures:
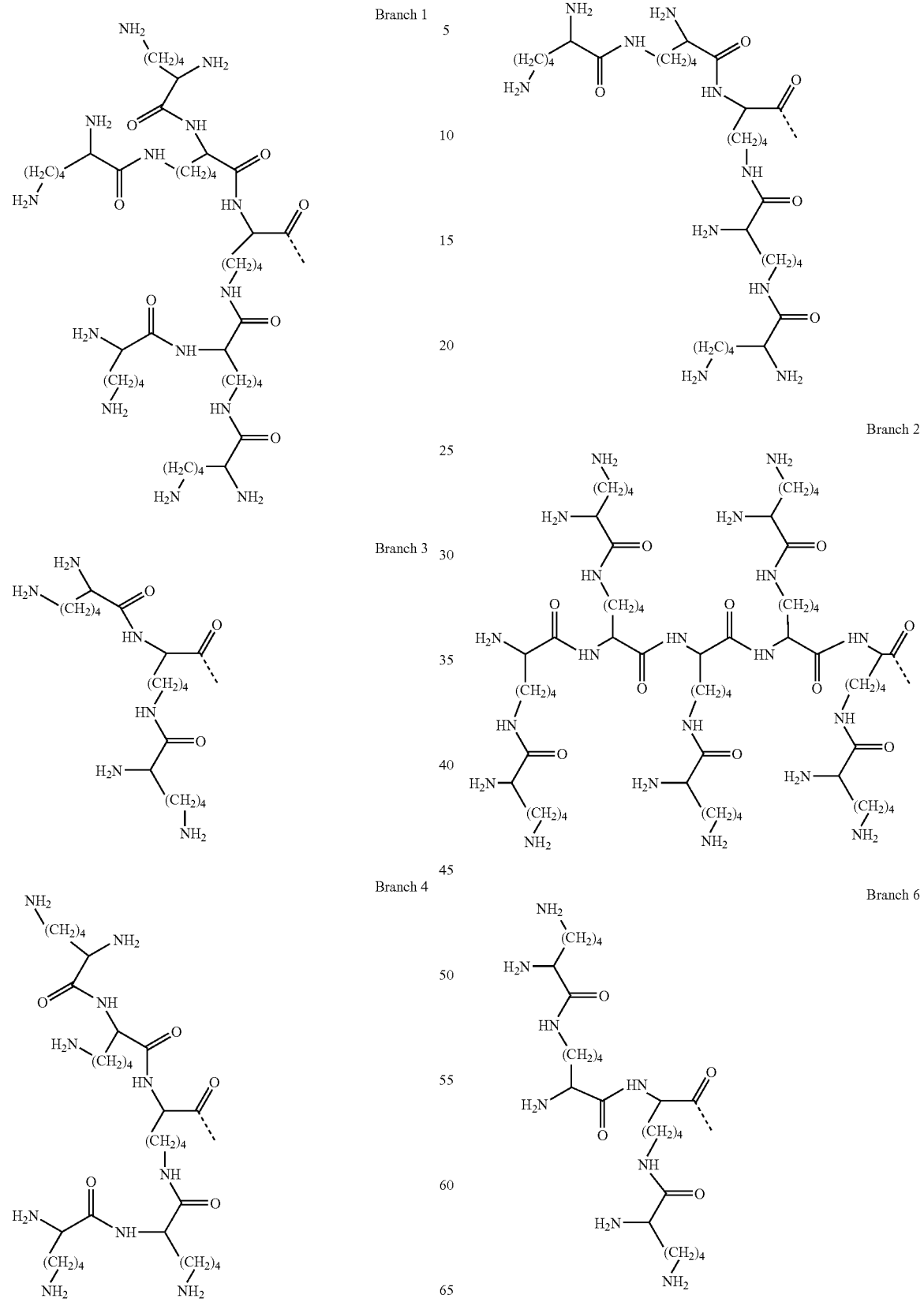

Example 36

Design of Phenotypic Assays for the Use of CD40 Inhibitors

Once CD40 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of CD40 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with CD40 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the CD40 inhibitors. Hallmark genes, or those genes suspected to be associated with a specific disease state, condition, or phenotype, are measured in both treated and untreated cells.

What is claimed is:

1. An antisense compound 12 to 30 nucleobases in length comprising an at least 8 consecutive nucleobase portion complementary to an equal length portion within nucleobases 73 to 121 of a nucleic acid molecule encoding CD40 (SEQ ID NO: 85), wherein said compound is at least 90% complementary to SEQ ID NO: 85 as measured over the entirety of said antisense compound.

2. The antisense compound of claim 1 comprising an oligonucleotide.

3. The antisense compound of claim 2 comprising a DNA oligonucleotide.

4. The antisense compound of claim 2 comprising an RNA oligonucleotide.

5. The antisense compound of claim 2 comprising a chimeric oligonucleotide.

6. The antisense compound of claim 1 having at least one modified internucleoside linkage, sugar moiety, or nucleobase.

7. The antisense compound of claim 1 having at least one 2'-O-methoxyethyl sugar moiety.

8. The antisense compound of claim 1 having at least one phosphorothioate internucleoside linkage.

9. The antisense compound of claim 1 wherein at least one cytosine is a 5-methylcytosine.

10. A method of inhibiting the expression of CD40 in a cell or tissue comprising contacting a cell or tissue selected from the group consisting of B-cells, macrophages, dendritic cells, thymic epithelial cells, Langerhans cells, vascular smooth muscle cells, endothelial cells, epithelial tumors, hematopoietic tumors, and tumor-infiltrating endothelial cells, with the antisense compound of claim 1 so that expression of CD40 is inhibited.

11. The antisense compound of claim 1 which is a peptide-nucleic acid antisense compound.

12. The antisense compound of claim 11, wherein the peptide-nucleic acid antisense compound has at least one cationic moiety conjugated thereto.

13. The antisense compound of claim 1, wherein said compound is at least 95% complementary to SEQ ID NO: 85 as measured over the entirety of said antisense compound.

14. The antisense compound of claim 1, wherein said compound is 100% complementary SEQ ID NO: 85 as measured over the entirety of said antisense compound.

15. An antisense compound 12 to 30 nucleobases in length, wherein said compound comprises at least a 8 contiguous nucleobase portion of a sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

16. The compound of claim 15, consisting of a single-stranded modified oligonueleotide.

17. The compound of claim 16, wherein the nucleobase sequence of the modified oligonucleotide is 100% complementary to SEQ ID NO: 85 as measured over the entirety of said antisense compound.

18. The compound of claim 16, wherein at least one internucleoside linkage is a modified internucleoside linkage.

19. The compound of claim 18, wherein each internucleoside linkage is a phosphorothioate internueleoside linkage.

20. The compound of claim 16, wherein at least one nucleoside comprises a modified sugar.

21. The compound of claim 20, wherein at least one modified sugar is a bicyclic sugar.

22. The compound of claim 20, wherein at least one modified sugar comprises a 2'-O-methoxyethyl or a 4'-$(CH_2)_n$-O-2' bridge, wherein n is 1 or 2.

23. The compound of claim 16, wherein at least one nucleoside comprises a modified nucleobase.

24. The compound of claim 23, wherein the modified nucleobase is a 5-methylcytosine.

25. The compound of claim 1, wherein the antisense compound comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

26. The compound of claim 25, wherein the antisense compound comprises:
   a gap segment consisting often linked deoxynucleosides;
   a 5' wing segment consisting of four linked nucleosides;
   a 3' wing segment consisting of four linked nucleosides;
   wherein the gap segment is positioned between the 5' wing segment and the 3' wing segment, wherein each nucleoside of each wing segment comprises a 2'-O-methoxyethyl sugar; wherein each cytosine in said antisense compound is a 5-methylcytosine, and wherein each internucleoside linkage of said antisense compound is a phosphorothioate linkage.

27. The compound of claim 26, wherein the antisense compound consists of 18 linked nucleosides.

28. A composition comprising the antisense compound of claim 1 or a salt thereof and a pharmaceutically acceptable carrier or diluent.

29. The composition of claim 28, consisting of a single-stranded oligonucleotide.

30. The composition of claim 28, wherein the antisense compound consists of 18 linked nucleosides.

31. A compound comprising an oligonucleotide consisting of 12 to 30 linked nucleosides having a nucleobase sequence comprising an at least 8 consecutive nucleobase portion complementary to an equal length portion within nucleobases 59-138 of SEQ ID NO: 85, wherein said compound is at least 90% complementary to SEQ ID NO: 85 as measured over the entirety of said oligonucleotide.

32. The compound of claim 15, wherein the antisense compound is 18 nucleobases in length.

33. A compound comprising an oligonucleotide consisting of 12 to 25 linked nucleosides having a nucleobase sequence complementary to an equal length portion within nucleobases 63 to 100 of a nucleic acid molecule encoding CD40 having SEQ ID NO: 85, wherein said compound is 100% complementary to SEQ ID NO: 85 as measured over the entirety of said antisense compound.

34. The compound of claim 33, comprising a DNA oligonucleotide.

35. The compound of claim 33, comprising a RNA oligonucleotide.

36. The compound of claim 33, comprising a chimeric oligonucleotide.

37. The compound of claim 33, consisting of a single-stranded modified oligonucleotide.

38. The compound of claim 37, wherein at least one internucleoside linkage is a modified internucleoside linkage.

39. The compound of claim 38, wherein each internucleoside linkage is a phosphorothioate internucleoside linkage.

40. The compound of claim 37, wherein at least one nucleoside comprises a modified sugar.

41. The compound of claim 37, wherein at least one modified sugar comprises a 2'-O-methoxyethyl.

42. The compound of claim 37, wherein at least one nucleoside comprises a modified nucleobase.

43. The compound of claim 42, wherein the modified nucleobase is a 5-methylcytosine.

44. The compound of claim 33, wherein the oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

45. The compound of claim 44, wherein the oligonucleotide comprises:
a gap segment consisting of ten linked deoxynucleosides;
a 5' wing segment consisting of four linked nucleosides;
a 3' wing segment consisting of four linked nucleosides;
wherein the gap segment is positioned between the 5' wing segment and the 3' wing segment, wherein each nucleoside of each wing segment comprises a 2'-O-methoxyethyl sugar;
wherein each cytosine in said antisense compound is a 5-methylcytosine, and wherein each internucleoside linkage of said antisense compound is a phosphorothioate linkage.

46. The compound of claim 45, wherein the compound consists of 18 linked nucleosides.

* * * * *